US010208293B2

(12) United States Patent
Hansen et al.

(10) Patent No.: US 10,208,293 B2
(45) Date of Patent: Feb. 19, 2019

(54) COMPOSITIONS AND METHODS FOR THE BIOSYNTHESIS OF VANILLAN OR VANILLIN BETA-D-GLUCOSIDE

(75) Inventors: Joergen Hansen, Frederiksberg (DK); Esben Halkjaer Hansen, Frederiksberg (DK); Honey Polur, Durham, NC (US); Joseph M. Sheridan, Royston (GB); Jonathan R. Heal, Attenborough (GB); William D. O. Hamilton, Royston (GB)

(73) Assignees: International Flavors & Fragrances Inc., New York, NY (US); Evolva SA, Reinach (CH)

( * ) Notice: Subject to any disclaimer, the term of this patent is extended or adjusted under 35 U.S.C. 154(b) by 1156 days.

(21) Appl. No.: 14/236,991

(22) PCT Filed: Aug. 7, 2012

(86) PCT No.: PCT/US2012/049842
§ 371 (c)(1), (2), (4) Date: Apr. 7, 2014

(87) PCT Pub. No.: WO2013/022881
PCT Pub. Date: Feb. 14, 2013

(65) Prior Publication Data

US 2014/0245496 A1 Aug. 28, 2014

Related U.S. Application Data

(60) Provisional application No. 61/521,090, filed on Aug. 8, 2011, provisional application No. 61/522,096, filed on Aug. 10, 2011.

(51) Int. Cl.

| | |
|---|---|
| *C07K 14/395* | (2006.01) |
| *C12N 15/52* | (2006.01) |
| *C12N 15/82* | (2006.01) |
| *C12N 9/04* | (2006.01) |
| *C12N 9/10* | (2006.01) |
| *C12N 9/88* | (2006.01) |
| *C12P 7/24* | (2006.01) |
| *C12P 19/46* | (2006.01) |
| *A23L 33/105* | (2016.01) |

(52) U.S. Cl.
CPC .......... *C12N 9/0006* (2013.01); *A23L 33/105* (2016.08); *C12N 9/1011* (2013.01); *C12N 9/88* (2013.01); *C12P 7/24* (2013.01); *C12P 19/46* (2013.01); *C12Y 201/01006* (2013.01); *C12Y 402/01118* (2013.01); *C07K 14/395* (2013.01); *C12N 15/8221* (2013.01); *C12Y 101/01025* (2013.01)

(58) Field of Classification Search
CPC .... C12Y 101/01025; C12Y 402/01118; C12Y 201/01006; C12N 9/1011; C12N 9/88; C12P 7/24; C12P 19/46
See application file for complete search history.

(56) References Cited

U.S. PATENT DOCUMENTS

| | | | | |
|---|---|---|---|---|
| 6,372,461 B1 * | 4/2002 | Frost | C12N 9/0008 435/156 |
| 2007/0231864 A1 | 10/2007 | Havkin-Frenkel et al. | 435/69.1 |

FOREIGN PATENT DOCUMENTS

| | | |
|---|---|---|
| WO | PCT/US2012/049842 | 11/2012 |
| WO | PCT/US2012/049842 | 2/2014 |

OTHER PUBLICATIONS

Hansen, Esben H., et al. "De novo biosynthesis of vanillin in fission yeast (*Schizosaccharomyces pombe*) and baker's yeast (*Saccharomyces cerevisiae*)." Applied and environmental microbiology 75.9 (2009): 2765-2774.*

Lamb, H. K., et al. "Comparative analysis of the QUTR transcription repressor protein and the three C-terminal domains of the pentafunctional AROM enzyme." Biochemical Journal 313.Pt 3 (1996): 941.*

Borneman, Anthony R., et al. "Whole-genome comparison reveals novel genetic elements that characterize the genome of industrial strains of *Saccharomyces cerevisiae*." PLoS Genet 7.2 (2011): e1001287.*

Dawling, Sheila, et al. "Catechol-O-methyltransferase (COMT)-mediated metabolism of catechol estrogens." Cancer research 61.18 (2001): 6716-6722.*

Michel, Gurvan, et al. "Structures of Shikimate Dehydrogenase AroE and Its Paralog YdiB a Common Structural Framework for Different Activities." Journal of Biological Chemistry 278.21 (2003): 19463-19472.*

Friedberg, Iddo. "Automated protein function prediction-the genomic challenge." Briefings in bioinformatics 7.3 (2006): 225-242.*

Ng, Pauline C., and Steven Henikoff. "Predicting deleterious amino acid substitutions." Genome research 11.5 (2001): 863-874. (Year: 2001).*

Duncan, K., R. M. Edwards, and J. R. Coggins. "The pentafunctional arom enzyme of *Saccharomyces cerevisiae* is a mosaic of monofunctional domains." Biochemical journal 246.2 (1987): 375-386. (Year: 1987).*

Hansen, Esben H., et al. "De novo biosynthesis of vanillin in fission yeast (*Schizosaccharomyces pombe*) and baker's yeast (*Saccharomyces cerevisiae*)." Applied and environmental microbiology 75.9 (2009): 2765-2774 (Year: 2009).*

(Continued)

*Primary Examiner* — Lee A Visone
*Assistant Examiner* — Weihua Fan
(74) *Attorney, Agent, or Firm* — Licata & Tyrrell P.C.

(57) ABSTRACT

Recombinant microorganisms, plants, and plant cells are disclosed that have been engineered to express a mutant AROM polypeptide and/or mutant catechol-O-methyltransferase polypeptide alone or in combination with one or more vanillin biosynthetic enzymes or UDP-glycosyltransferases (UGTs). Such microorganisms, plants, or plant cells can produce vanillin or vanillin beta-D-glucoside.

2 Claims, 5 Drawing Sheets

Specification includes a Sequence Listing.

(56) References Cited

OTHER PUBLICATIONS

Lamb, H. K., et al. "Comparative analysis of the QUTR transcription repressor protein and the three C-terminal domains of the pentafunctional AROM enzyme." Biochemical Journal 313.Pt 3 (1996): 941. (Year: 1996).*
Dawling, Sheila, et al. "Catechol-O-methyltransferase (COMT)-mediated metabolism of catechol estrogens." Cancer research 61.18 (2001): 6716-6722. (Year: 2001).*
Friedberg, Iddo. "Automated protein function prediction—the genomic challenge." Briefings in bioinformatics 7.3 (2006): 225-242. (Year: 2006).*
Michel, Gurvan, et al. "Structures of Shikimate Dehydrogenase AroE and Its Paralog YdiB a Common Structural Framework for Different Activities." Journal of Biological Chemistry 278.21 (2003): 19463-19472. (Year: 2003).*
Duncan, K., R. M. Edwards, and J. R. Coggins. "The pentafunctional arom enzyme of *Saccharomyces cerevisiae* is a mosaic of monofunctional donnains." Biochemical journal 246.2 (1987): 375-386. (Year: 1987).*
Duncan et al. "The Pentafunctional Arom Enzyme of *Saccharomyces cerevisiae* is a Mosaic of Monofunctional Domains" Biochemical Journal 1987 246(3):375-386.
Hansen et al. "De Novo Biosynthesis of Vanillin in Fission Yeast (*Schizosaccharomyces pombe*) and Baker's Yeast (*Saccharomyces cerevisiae*)" Applied and Environmental Microbiology 2009 75(9):2765-2774.
Ramachandra Rao, S. and Ravishankar, G. A. "Vanilla Flavour: Production by Conventional and Biotechnological Routes" Journal of the Science of Food and Agriculture 2000 80:289-304.
Reenilä, I. and Rauhala, P. "Simultaneous Analysis of Catechol-O-Methyl Transferase Activity, S-Adenosylhomocysteine and Adenosine" Biomedical Chromatography 2010 24(3):294-300.
Walton, et al. "Vanillin" Phytochemistry 2003 63:505-515.
Genbank Accession No. EAW07456 GI:119397025 "Genomic Islands in the Pathogenic Filamentous Fungus *Aspergillus fumigatus*" Apr. 18, 2008.
Uniprot.E7NFR1_YEASO [online] Jun. 28, 2011 Available on the internet: URL: http://www.uniprot.org/uniprot/E7NFR1.txt?version=4 Especially p. 2-3.
Uniprot P21964. COMT_Human [online] Apr. 5, 2011 Available on the internet: URL: http://www.uniprot.org/uniprot/P21964.txt?version=135 Especially p. 7-8.
Iwaki et al. "Vanillin Inhibits Translation and Induces Messenger Ribonucleoprotein (mRNP) Granule Formation in *Saccharomyces cerevisiae*: Application and Validation of High-Content, Image-Based Profiling" PLoS One Apr. 24, 2013 8(4):e61748 1-10.
Li, T. and Rosazza, J.P.N. "Biocatalytic Synthesis of Vanillin" Applied and Environmental Microbiology 2000 684-687.
Liu, Z.L. "Molecular Mechanisms of Yeast Tolerance and in situ Detoxification of Lignocellulose Hydrolysates" 2011 90:809-825.
International Search Report and Written Opinion dated Dec. 22, 2014 from PCT/US2014/046315.
Genbank:EGA59386 "Aro1p [*Saccharomyces cerevisiae* FostersB]" Feb. 11, 2011.
Notification of Office Action dated Feb. 17, 2015 from Chinese Application No. 201280048260.5.
Extended European Search Report dated Mar. 23, 2015 from EPO Application No. 12822242.9.
Geneseq Database:XP002737041 "Aspergillus Fumigatus AR01 Protein" Nov. 2, 2006.
UniProt Database:XP002737042 "SubName: Full-Membrane bound catechol-0-methyltransferse" Mar. 3, 2009.
Li, K. and Frost, J.W. "Synthesis of Vanillin from Glucose" Journal of the American Chemical Society 1998 120 (40) :10545-10546.

* cited by examiner

COMPOSITIONS AND METHODS FOR THE BIOSYNTHESIS OF VANILLAN OR VANILLIN BETA-D-GLUCOSIDE

The application is the national stage under 35 U.S.C. § 371 of PCT International Application No. PCT/US2012/049842, filed Aug. 7, 2012, which claims the benefit of priority of U.S. Provisional Application Nos. 61/521,090, filed Aug. 8, 2011 and 61/522,096, filed Aug. 10, 2011, the contents of which are incorporated herein by reference in their entirety.

BACKGROUND OF THE INVENTION

Vanillin is one of the world's most important flavor compounds with a global market of 180 million dollars. Natural vanillin is derived from the cured seed pods of the vanilla orchid (*Vanilla planifolia*), but most of the world's vanillin is synthesized from petrochemicals or wood pulp lignins. Production of natural vanillin from the vanilla pod is a laborious and slow process, which requires hand pollination of the flowers and a 1-6 month curing process of the harvested green vanilla pods (Ramachandra & Ravishankar (2000) *J. Sci. Food Agric.* 80:289-304). Production of 1 kilogram (kg) of vanillin requires approximately 500 kg of vanilla pods, corresponding to pollination of approximately 40,000 flowers. Today only about 0.25% (40 tons out of 16,000) of vanillin sold annually originates from vanilla pods, while most of the remainder is synthesized chemically from lignin or fossil hydrocarbons, in particular guaiacol. Synthetically produced vanillin is sold for approximately $15 per kg, compared to prices of $1200-4000 per kg for natural vanillin (Walton, et al. (2003) *Phytochemistry* 63:505-515).

SUMMARY OF THE INVENTION

This invention provides a method for producing vanillin and/or vanillin beta-D-glucoside. The method of the invention involves the steps of (a) providing a recombinant host capable of producing vanillin, wherein said recombinant host harbors a heterologous nucleic acid encoding a mutant Arom Multifunctional Enzyme (AROM) polypeptide and/or a mutant Catechol-O-Methyl Transferase (COMT) polypeptide; (b) cultivating said recombinant host for a time sufficient for said recombinant host to produce vanillin and/or vanillin glucoside; and (c) isolating vanillin and/or vanillin glucoside from said recombinant host or from the cultivation supernatant, thereby producing vanillin and/or vanillin beta-D-glucoside.

In one embodiment, a mutant AROM polypeptide is provided, wherein said mutant has decreased shikimate dehydrogenase activity relative to a corresponding AROM polypeptide that lacks the mutation. In accordance with this embodiment, the mutant AROM polypeptide can have one or more mutations in domain 5, a deletion of at least portion of domain 5, or lack domain 5.

In another embodiment, the mutant AROM polypeptide is a fusion polypeptide that includes (i) an AROM polypeptide described herein, e.g., an AROM polypeptide comprising a deletion of at least a portion of domain 5 or an AROM polypeptide lacking domain 5; and (ii) a polypeptide having 3-dehydroshikimate dehydratase (3DSD) activity.

In a further embodiment, a mutant COMT polypeptide is provided, wherein said mutant has one or more improved properties. In particular, the invention provides mutant COMT polypeptides that preferentially catalyze methylation at the meta position of protocatechuic acid, and/or protocatechuic aldehyde, and/or protocatechuic alcohol rather than at the para position.

Any of the polypeptides described herein further can include a purification tag, a chloroplast transit peptide, a mitochondrial transit peptide, an amyloplast peptide, signal peptide, or a secretion tag at the N or C-terminus of the polypeptide.

In some embodiments, the host can be a microorganism, e.g., a yeast such as *Saccharomyces cerevisiae, Schizosaccharomyces pombe* or *Escherichia coli*. Alternatively, the host can be a plant or plant cell (e.g, a *Physcomitrella* or tobacco plant or plant cell).

Any of the hosts described herein further can include a gene encoding an aromatic carboxylic acid reductase (ACAR); a 3-dehydroshikimate dehydratase (3DSD); a uridine 5'-diphosphoglucosyl transferase (UGT); a phosphopantetheine transferase (PPTase); a wild-type AROM; and/or a wild type O-methyltransferase (OMT).

An isolated nucleic acid encoding a mutant COMT polypeptide or mutant AROM polypeptide is also provided.

DETAILED DESCRIPTION OF THE INVENTION

Figure 1:
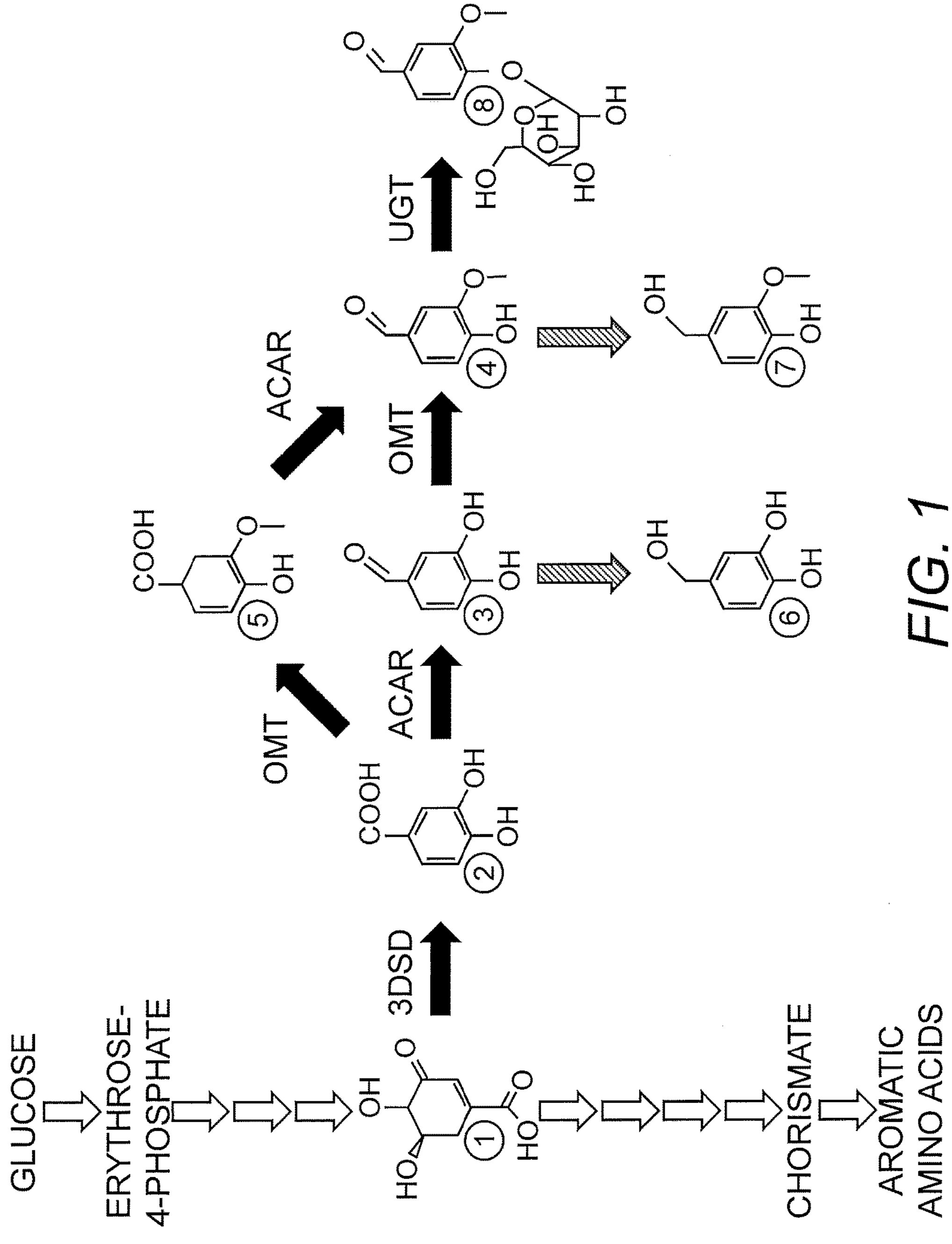
FIG. 1 is a schematic of de novo biosynthesis of vanillin (4) and outline of the different vanillin catabolites and metabolic side products, i.e., dehydroshikimic acid (1), protocatechuic acid (2), protocatechuic aldehyde (3), vanillic acid (5), protocatechuic alcohol (6), vanillyl alcohol (7), and vanillin β-D-glucoside (8), found in an organism expressing 3DSD, ACAR, OMT, and UGT and a phophopantheteine transferase (PPTase). Open arrows show primary metabolic reactions in yeast; black arrows show enzyme reactions introduced by metabolic engineering; diagonally striped arrows show undesired inherent yeast metabolic reactions.

This invention is based on the discovery that mutant AROM polypeptides can be used to increase 3-dehydroshikimate (3-DHS) accumulation in recombinant hosts. 3-DHS is a precursor for vanillin biosynthesis, and if more intracellular 3-DHS is available, more protocatechuic acid can be made in the first committed step of the vanillin biosynthetic pathway. See FIG. 1. AROM is a penta-functional enzyme complex encoded in yeast by the ARO1 gene. The gene is 4764 bp long and encodes a corresponding polypeptide 1588 amino acids in length. AROM performs five consecutive enzymatic conversions, i.e., converting DAHP (3-deoxy-D-arabino-heptulosonic acid-7-phosphate) into 3-DHQ (3-dehydroquinate), which is converted to 3-DHS (3-dehydroshikimic acid), which is converted to shikimate, which is converted to shikimate-3-P (shikimate 3-phosphate), which is converted into EPSP (5-enolpyruvylskimate 3-phosphate), all en route to cellular biosynthesis of the aromatic amino acids tyrosine, tryptophan and phenylalanine (see FIG. 2).

The five catalytic functions of AROM reside on five distinct domains of the ARO1-encoded polypeptide. The functional domains of the AROM polypeptide are in a different order than the order with which they, are needed in the five-step conversion of DAHP to EPSP (see FIG. 2). Thus, while domain 1 corresponds with catalytic activity 1, domain 2 corresponds with catalytic activity 5, domain 3 corresponds with catalytic activity 4, domain 4 corresponds with catalytic activity 2, and finally domain 5 corresponds with catalytic activity 3 (see FIG. 1).

Recombinant hosts containing domain 5 variants of the AROM polypeptide (e.g., an AROM polypeptide having one or more mutations within domain 5 or an AROM polypeptide in which a portion of domain 5 is deleted) can have increased levels of 3-DHS in comparison to a corresponding host expressing a wild-type AROM polypeptide. Such hosts also can have increased protocatechuic acid production.

Alternatively, or in addition to, mutant COMT polypeptides can be used to improve biosynthesis of vanillin beta-D-glucoside. For example, mutant COMT polypeptides described herein can have one or more of the following properties: increased turnover; preferential methylation at the meta (3') position, rather than at the para (4') position such that production of vanillin is favored over isovanillin; or better specificity for the vanillin pathway substrates, protocatechuic acid and protocatechuic aldehyde.

Accordingly, the invention provides mutant AROM and mutant COMT polypeptides and nucleic acids encoding such polypeptides and use of the same in the biosynthesis of vanillin and/or vanillin glucoside. The method includes the steps of providing a recombinant host capable of producing vanillin in the presence of a carbon source, wherein said recombinant host harbors a heterologous nucleic acid encoding a mutant COMT polypeptide and/or mutant AROM polypeptide; cultivating said recombinant host in the presence of the carbon source; and purifying vanillin and/or vanillin glucoside from said recombinant host or from the cultivation supernatant.

Recombinant hosts described herein can be used in methods to produce vanillin or vanillin glucoside. For example, if the recombinant host is a microorganism, the method can include growing the recombinant microorganism in a culture medium under conditions in which vanillin and/or vanillin glucoside biosynthesis genes are expressed. The recombinant microorganism may be grown in a batch, fed batch or continuous process or combinations thereof. Typically, the recombinant microorganism is grown in a fermentor at a defined temperature(s) in the presence of a suitable nutrient source, e.g., a carbon source, for a desired period of time to produce a desired amount of vanillin and/or vanillin glucoside.

Carbon sources of use in the instant method include any molecule that can be metabolized by the recombinant host cell to facilitate growth and/or production of the vanillin and/or vanillin glucoside. Examples of suitable carbon sources include, but are not limited to, sucrose (e.g., as found in molasses), fructose, xylose, ethanol, glycerol, glucose, cellulose, starch, cellobiose or other glucose containing polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

In one embodiment, the microorganism of this method harbors a nucleic acid encoding mutant AROM polypeptide and optionally a wild-type COMT polypeptide. In another embodiment, the microorganism of this method harbors a nucleic acid encoding mutant COMT, polypeptide and optionally a wild-type AROM polypeptide. In yet another embodiment, the microorganism of this method harbors a nucleic acid encoding mutant AROM polypeptide and optionally a mutant COMT polypeptide. Depending on the particular microorganism used in the method, other recombinant genes encoding a 3DSD, ACAR, UGT, or PPTase may also be present and expressed. Thus, the recombinant host may, in one embodiment, be a microorganism harboring one or more heterologous nucleic acids encoding 3DSD, ACAR, UGT or PPTase or a functional homologue of any of the aforementioned sharing at least 80%, such as at least 90%, for example at least 95% sequence identity therewith. Levels of products, substrates and intermediates, e.g., dehydroshikimic acid, protocatechuic acid, protocatechuic aldehyde, vanillin, and vanillin beta-D-glucoside can be determined by extracting samples from culture media for analysis according to published methods.

After the recombinant microorganism has been grown in culture for the desired period of time, vanillin and/or vanillin beta-D-glucoside can then be recovered from the culture using various techniques known in the art, e.g., isolation and purification by extraction, vacuum distillation and multi-stage re-crystallization from aqueous solutions and ultrafiltration (Böddeker, et al. (1997) *J. Membrane Sci.* 137:155-158; Borges da Silva, et al. (2009) *Chem. Eng. Des.* 87:1276-1292). Two-phase extraction processes, employing either sulphydryl compounds, such as dithiothreitol, dithioerythritol, glutathione, or L-cysteine (U.S. Pat. No. 5,128,253), or alkaline KOH solutions (WO 94/13614), have been used in the recovery of vanillin as well as for its separation from other aromatic substances. Vanillin adsorption and pervaporation from bioconverted media using polyether-polyamide copolymer membranes has also been described (Boddeker, et al. (1997) supra; Zucchi, et al. (1998) *J. Microbiol. Biotechnol.* 8:719-722). Macroporous adsorption resins with crosslinked-polystyrene framework have also been used to recover dissolved vanillin from aqueous solutions (Zhang, et al. (2008) *Eur. Food Res. Technol.* 226:377-383). Ultrafiltration and membrane contactor (MC) techniques have also been evaluated to recover vanillin (Zabkova, et al. (2007) *J. Membr. Sci.* 301:221-237; Scuibba, et al. (2009) *Desalination* 241:357-364). Alternatively, conventional techniques such as percolation or supercritical carbon dioxide extraction and reverse osmosis for concentration could be used. If the recombinant host is a plant or plant cells, vanillin or vanillin glucoside can be extracted from the plant tissue using various techniques known in the art.

In some embodiments, vanillin or vanillin beta-D-glucoside can be produced using whole cells that are fed raw materials that contain precursor molecules. The raw materials may be fed during cell growth or after cell growth. The whole cells may be in suspension or immobilized. The whole cells may be in fermentation broth or in a reaction buffer. In some embodiments a permeabilizing agent may be required for efficient transfer of substrate into the cells.

In some embodiments, the vanillin or vanillin beta-D-glucoside is isolated and purified to homogeneity (e.g., at least 90%, 92%, 94%, 96%, or 98% pure). In other embodiments, the vanillin or vanillin beta-D-glucoside is isolated as an extract from a recombinant host. In this respect, vanillin or vanillin beta-D-glucoside may be isolated, but not necessarily purified to homogeneity. Desirably, the amount of vanillin or vanillin beta-D-glucoside produced can be from about 1 mg/l to about 20,000 mg/L or higher. For example about 1 to about 100 mg/L, about 30 to about 100 mg/L, about 50 to about 200 mg/L, about 100 to about 500 mg/L, about 100 to about 1,000 mg/L, about 250 to about 5,000 mg/L, about 1,000 to about 15,000 mg/L, or about 2,000 to about 10,000 mg/L of vanillin or vanillin beta-D-glucoside can be produced. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce vanillin and/or vanillin glucoside.

Extracts of isolated, and optionally purified, vanillin or vanillin beta-D-glucoside find use in flavoring consumables such as food products, dietary supplements, nutraceuticals, pharmaceutical compositions, dental hygienic compositions, and cosmetic products.

The phrase "food product," as used herein, includes, but is not limited to, fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, cakes, cookies, confectionaries such as candies, gums, fruit flavored drops, and chocolates, chewing gum, mints, creams, icing, ice cream, pies and breads, beverages such as coffee, tea, carbonated soft drinks, such as COKE and PEPSI, non-carbonated soft drinks, juices and other fruit drinks, sports drinks such as GATORADE, coffee, teas, iced teas, cola, alcoholic beverages, such as beers, wines and liquors, and KOOL-AID.

Food products also include condiments such as herbs, spices and seasonings, flavor enhancers. A food product also includes prepared packaged products, such as dietetic sweeteners, liquid sweeteners, granulated flavor mixes which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like. Food products also include diet or low-calorie food and beverages containing little or no sucrose. Other examples of food products envisioned in accordance with the present invention are described below and throughout the specification.

In another embodiment, the food products are fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, cakes, cookies, confectionaries such as candies, gums, fruit flavored drops, and chocolates, creams, icing, ice cream, pies and breads.

In another embodiment, the consumable is a pharmaceutical composition. Preferred compositions are pharmaceutical compositions containing vanillin and/or vanillin beta-D-glucoside and one or more pharmaceutically acceptable excipients. These pharmaceutical compositions can be used to formulate pharmaceutical drugs containing one or more active agents that exert a biological effect. As such, the pharmaceutical composition preferably further include one or more active agents that exert a biological effect. Such active agents include pharmaceutical and biological agents that have an activity. Such active agents are well known in the art. See, e.g., The Physician's Desk Reference. Such compositions can be prepared according to procedures known in the art, for example, as described in Remington's Pharmaceutical Sciences, Mack Publishing Co., Easton, Pa., USA. In one embodiment, such an active agent includes bronchodilators, anorexiants, antihistamines, nutritional supplements, laxatives, analgesics, anesthetics, antacids, H2-receptor antagonists, anticholinergics, antidiarrheals, demulcents, antitussives, antinauseants, antimicrobials, antibacterials, antifungals, antivirals, expectorants, anti-inflammatory agents, antipyretics, and mixtures thereof. In one embodiment, the active agent is an antipyretics or analgesics, e.g., ibuprofen, acetaminophen, or aspirin; laxatives, e.g., phenolphthalein dioctyl sodium sulfosuccinate; appetite depressants, e.g., amphetamines, phenylpropanolamine, phenylpropanolamine hydrochloride, or caffeine; antacidics, e.g., calcium carbonate; antiasthmatics, e.g., theophylline; antidiuretics, e.g., diphenoxylate hydrochloride; agents active against flatulence, e.g., simethecon; migraine agents, e.g., ergotaminetartrate; psychopharmacological agents, e.g., haloperidol; spasmolytics or sedatives, e.g., phenobarbitol; antihyperkinetics, e.g., methyldopa or methylphenidate; tranquilizers, e.g., benzodiazepines, hydroxinmeprobramates or phenothiazines; antihistaminics, e.g., astemizol, chloropheniramine maleate, pyridamine maleate, doxlamine succinate, bromopheniramine maleate, phenyltoloxamine citrate, chlorocyclizine hydrochloride, pheniramine maleate, and phenindamine tartrate; decongestants, e.g., phenylpropanolamine hydrochloride, phenylephrine hydrochloride, pseudoephedrine hydrochloride, pseudoephedrine sulfate, phenylpropanolamine bitartrate, and ephedrine; beta-receptor blockers, e.g., propanolol; agents for alcohol withdrawal, e.g., disulfuram; antitussives, e.g., benzocaine, dextromethorphan, dextromethorphan hydrobromide, noscapine, carbetapentane citrate, and chlophedianol hydrochloride; fluorine supplements, e.g., sodium fluoride; local antibiotics, e.g., tetracycline or cleocine; corticosteroid supplements, e.g., prednisone or prednisolone; agents against goiter formation, e.g., colchicine or allopurinol; antiepileptics, e.g., phenyloine sodium; agents against dehydration, e.g., electrolyte supplements; antiseptics, e.g., cetylpyridinium chloride; NSAIDs, e.g., acetaminophen, ibuprofen, naproxen, or salts thereof; gastrointestinal active agents, e.g., loperamide and famotidine; various alkaloids, e.g., codeine phosphate, codeine sulfate, or morphine; supplements for trace elements, e.g., sodium chloride, zinc chloride, calcium carbonate, magnesium oxide, and other alkali metal salts and alkali earth metal salts; vitamins; ion-exchange resins, e.g., cholestyramine; cholesterol-depressant and lipid-lowering substances; antiarrhythmics, e.g., N-acetylprocainamide; and expectorants, e.g., guaifenesin.

Active substances which have a particularly unpleasant taste include antibacterial agents such as ciprofloxacin, ofloxacin, and pefloxacin; antiepileptics such as zonisamide; macrolide antibiotics such as erythromycin; beta-lactam antibiotics such as penicillins and cephalosporins; psychotropic active substances such as chlorpromazine; active substances such as sulpyrine; and agents active against ulcers, such as cimetidine.

The pharmaceutical compositions of this invention are administered to a subject in any form suitable to achieve their intended purpose. Preferably, however, the composition is one which can be administered buccally or orally. Alternatively, the pharmaceutical composition can be an oral or nasal spray. The subject is any animal, such as a human, although the invention is not intended to be so limited. Other suitable animals include canines, felines, dogs, cats, livestock, horses, cattle, sheep, and the like. A veterinary composition, as used herein, refers to a pharmaceutical composition that suitable for non-human animals. Such veterinary compositions are known in the art.

In another embodiment, the pharmaceutical composition is a liquid dosage form for oral administration, including pharmaceutically acceptable emulsions, solutions, suspensions, syrups, and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The pharmaceutical composition of the present invention can be in the form of a chewable tablet. Chewable tablets are known in the art. See, e.g., U.S. Pat. Nos. 4,684,534 and 6,060,078, each of which is incorporated by reference in its entirety. Any kind of medicament can be contained in the chewable tablet, preferably a medicament of bitter taste, natural plant extracts or other organic compounds. More preferably, vitamins such as vitamin A, vitamin B, vitamin B1, vitamin B2, vitamin B6, vitamin C, vitamin E and vitamin K; natural plant extracts such as Sohgunjung-tang extracts, Sipchundaebo-tang extracts and Eleutherococcus senticosus extracts; organic compounds such as dimenhydrinate, meclazine, acetaminophen, aspirin, phenylpropanolamine, and cetylpyridinium chloride; or gastrointestinal agents such as dried aluminum hydroxide gel, domperidone, soluble azulene, L-glutamine and hydrotalcite can be contained in the core.

The pharmaceutical composition of the present invention can be an orally disintegrating composition. Orally disintegrating tablets are known in the art. See, e.g., U.S. Pat. Nos. 6,368,625 and 6,316,029, each of which is hereby incorporated by reference in its entirety.

The pharmaceutical composition of the present invention can be a solid dosage form, including vanillin or vanillin beta-D-glucoside and a water and/or saliva activated effervescent granule, such as one having a controllable rate of effervescence. The effervescent composition can further comprise a pharmaceutically active compound. Effervescent pharmaceutical compositions are known in the art. See, e.g., U.S. Pat. No. 6,649,186, which is incorporated by reference in its entirety. The effervescent composition can be used in pharmaceutical, veterinary, horticultural, household, food, culinary, pesticidal, agricultural, cosmetic, herbicidal, industrial, cleansing, confectionery and flavoring applications. Formulations incorporating the effervescent composition containing vanillin or vanillin beta-D-glucoside can further include one or more additional adjuvants and/or active ingredients which can be chosen from those known in the art, including flavors, diluents, colors, binders, filler, surfactant, disintegrant, stabilizer, compaction vehicles, and non-effervescent disintegrants.

The pharmaceutical composition can be a film-shaped or wafer-shaped pharmaceutical composition. Such a film-shaped or wafer-shaped pharmaceutical composition can be configured, for example, as quickly disintegrating administration forms, e.g., administration forms disintegrating within a period of 1 second up to 3 minutes, or as slowly disintegrating administration forms, e.g., administration forms disintegrating within a period of 3 to 15 minutes. The indicated disintegration times can be set to the above-mentioned ranges by using, for example, matrix-forming polymers which have different disintegrating, or solubility, characteristics. Thus, by mixing the corresponding polymer components, the disintegration time can be adjusted. In addition, disintegrants are known which “draw” water into the matrix and cause the matrix to burst open from within. As a consequence, certain embodiments of the invention include such disintegrants for the purpose of adjusting the disintegration time.

Suitable are polymers for use in the film-shaped or wafer-shaped pharmaceutical composition include cellulose derivatives, polyvinyl alcohol (e.g. MOWIOL), polyacrylates, polyvinyl pyrrolidone, cellulose ethers, such as ethyl cellulose, as well as polyvinyl alcohol, polyurethane, polymethacrylates, polymethyl methacrylates and derivatives and copolymerizates of the aforementioned polymers.

In certain embodiments, the total thickness of the film-shaped or wafer-shaped pharmaceutical composition according to the invention is preferably 5 μm up to 10 mm, preferably 30 μm to 2 mm, and with particular preference 0.1 mm to 1 mm. The pharmaceutical preparations can be round, oval, elliptic, triangular, quadrangular or polygonal shape, but they can also have any rounded shape.

The pharmaceutical composition of the present invention can be in the form of an aerosol. The aerosol composition can further include a pharmaceutically active agent. Aerosol compositions are known in the art. See, e.g., U.S. Pat. No. 5,011,678, which is hereby incorporated by reference in its entirety. As a nonlimiting example, an aerosol composition according to the present invention can include a medically effective amount of a pharmaceutically active substance, vanillin or vanillin beta-D-glucoside and a biocompatible propellant, such as a (hydro/fluoro)carbon propellant.

In one embodiment of the present invention, the pharmaceutical composition is a nutritional composition. Examples of nutritional compositions having an undesirable taste include, but are not necessarily limited to, enteral nutrition products for treatment of nutritional deficit, trauma, surgery, Crohn's disease, renal disease, hypertension, obesity and the like, to promote athletic performance, muscle enhancement or general well being or inborn errors of metabolism such as phenylketonuria. In particular, such nutritional formulations can contain one or more amino acids which have a bitter or metallic taste or aftertaste. Such amino acids include, but are not limited to, an essential amino acids such as an L isomer of leucine, isoleucine, histidine, lysine, methionine, phenylalanine, threonine, tryptophan, tyrosine or valine.

In one embodiment, the consumable of the present invention is a dental hygienic composition containing vanillin and/or vanillin beta-D-glucoside. Dental hygienic compositions are known in the art and include, but are not necessarily limited to, toothpaste, mouthwash, plaque rinse, dental floss, dental pain relievers (such as ANBESOL), and the like.

In another embodiment, the consumable of the present invention is a cosmetic product containing vanillin and/or vanillin beta-D-glucoside. For example, but not by way of limitation, the cosmetic product can be a face cream, lipstick, lip gloss, and the like. Other suitable compositions of the invention include lip balm, such as CHAPSTICK or BURT'S BEESWAX Lip Balm, further containing vanillin and/or vanillin beta-D-glucoside.

Arom Multifunctional Enzyme (AROM) Polypeptides

Non-limiting examples of AROM polypeptides include the *Saccharomyces cerevisiae* polypeptide having the amino acid sequence set forth in SEQ ID NO:4 (GENBANK Accession No. X06077); a *Schizosaccharomyces pombe* polypeptide (GENBANK Accession No. NP_594681.1); a *Schizosaccharomyces japonicas* polypeptide (GENBANK Accession No. XP_002171624); a *Neurospora crassa* polypeptide (GENBANK Accession No. XP_956000); and a *Yarrowia lipolytica* polypeptide (GENBANK Accession No. XP_505337).

The term "AROM polypeptide" as used herein refers to any amino acid sequence that is at least 80 percent (e.g., at least 85, 90, 95, 96, 97, 98, 99, or 100 percent) identical to the sequence set forth in SEQ ID NO:4, and possesses at least four of the five enzymatic activities of the *S. cerevisiae* AROM polypeptide, i.e., 3-dehydroquinate dehydratase activity, 3-dehydroquinate synthase activity, 3-phosphoshikimate 1-carboxyvinyltransferase activity, shikimate 3-dehydrogenase (NADP+) activity, and shikimate kinase activity.

Figure 2:
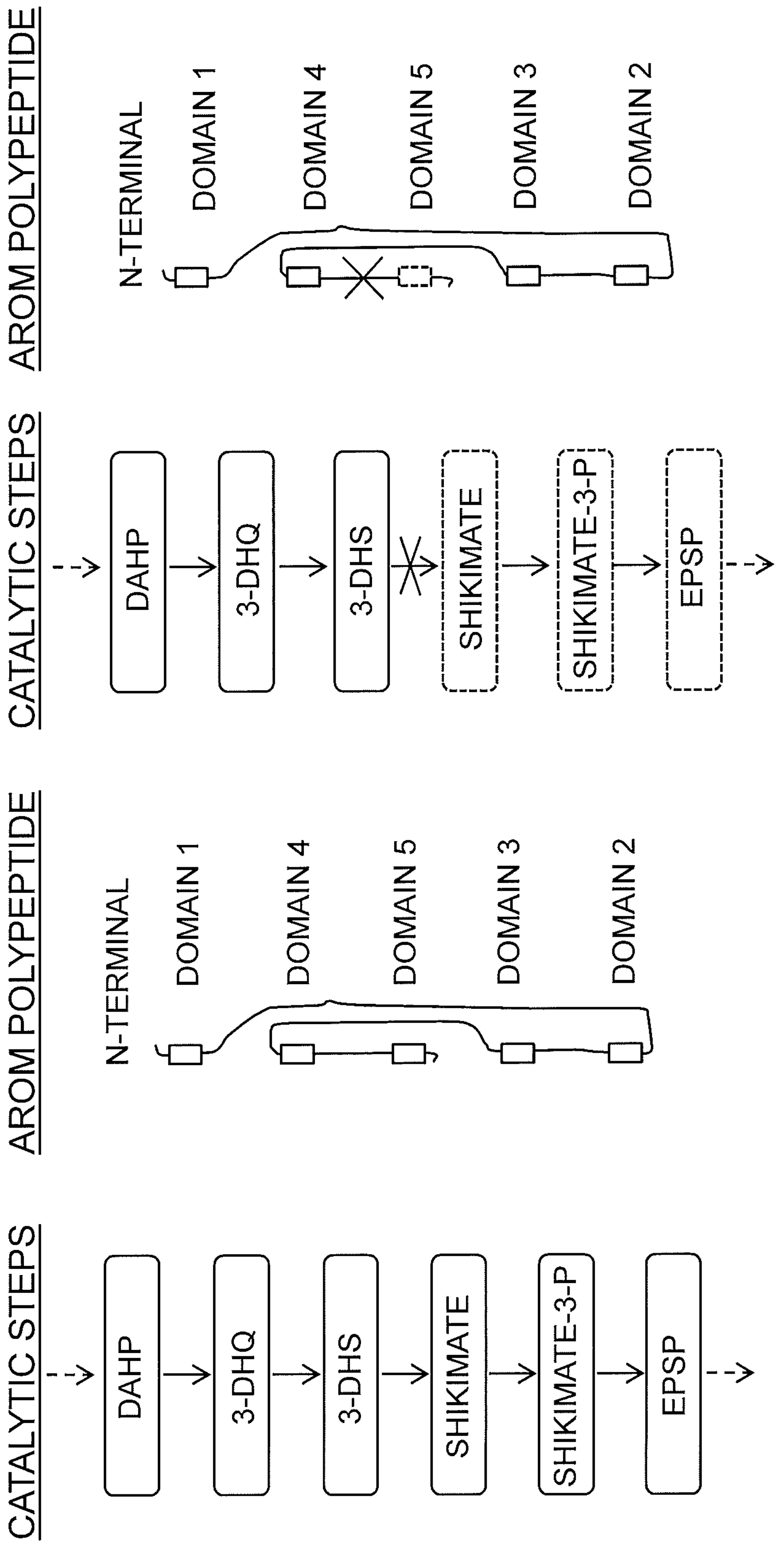
FIG. 2 is a schematic depiction of the cellular biosynthesis of the aromatic amino acids tyrosine, tryptophan and phenylalanine using a wild-type AROM polypeptide (left) and a mutant AROM polypeptide lacking domain 5 (right).

According to one embodiment of this invention, the AROM polypeptide is a mutant AROM polypeptide with decreased shikimate dehydrogenase activity. When expressed in a recombinant host, the mutant AROM polypeptide redirects metabolic flux from aromatic amino acid production to vanillin precursor production (FIG. 2). Decreased shikimate dehydrogenase activity can be inferred from the accumulation of dehydroshikimic acid in a recombinant host expressing a mutant AROM polypeptide, using LC-MS.

The mutant AROM polypeptide described herein can have one or more modifications in domain 5 (e.g., a substitution of one or more amino acids, a deletion of one or more amino acids, insertions of one or more amino acids, or combinations of substitutions, deletions, and insertions). For example, a mutant AROM polypeptide can have a deletion in at least a portion of domain 5 (e.g., a deletion of the entire domain 5, i.e., amino acids 1305 to 1588 of the amino acid sequence in SEQ ID NO:4, or can have one or more amino acid substitutions in domain 5, such that the mutant AROM polypeptide has decreased shikimate dehydrogenase activity. An exemplary mutant AROM polypeptide lacking domain 5 is provided in SEQ ID NO:2. Exemplary mutant AROM polypeptides with at least one amino acid substitution in domain 5 include the AROM polypeptides A1533P, P1500K, R1458W, V1349G, T1366G, I1387H, W1571V, T1392K, K1370L and A1441P as set forth in SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 and SEQ ID NO:24, respectively.

Amino acid substitutions that are particularly useful can be found at, for example, one or more positions aligning with position 1349, 1366, 1370, 1387, 1392, 1441, 1458, 1500, 1533, or 1571 of the amino acid sequence set forth in SEQ ID NO:4. For example, a modified AROM polypeptide can have a substitution at a position aligning with position 1370 or at position 1392 of the amino acid sequence set forth in SEQ ID NO:4.

For example, a modified AROM polypeptide can have one or more of the following: an amino acid other than valine (e.g., a glycine) at a position aligning with position 1349 of the amino acid sequence set forth in SEQ ID NO:4; an amino acid other than threonine (e.g., a glycine) at a position aligning with position 1366 of the amino acid sequence set forth in SEQ ID NO:4; an amino acid other than lysine (e.g., leucine) at a position aligning with position 1370 of the amino acid sequence set forth in SEQ ID NO:4; an amino acid other than isoleucine (e.g., histidine) at a position aligning with position 1387 of the amino acid sequence set forth in SEQ ID NO:4; an amino acid other than threonine (e.g., lysine) at a position aligning with position 1392 of the amino acid sequence set forth in SEQ ID NO:4; an amino acid other than alanine (e.g., proline) at a position aligning with position 1441 of the amino acid sequence set forth in SEQ ID NO:4; an amino acid other than arginine (e.g., tryptophan) at a position aligning with position 1458 of the amino acid sequence set forth in SEQ ID NO:4; an amino acid other than proline (e.g., lysine) at a position aligning with position 1500 of the amino acid sequence set forth in SEQ ID NO:4; an amino acid other than alanine (e.g., proline) at a position aligning with position 1533 of the amino acid sequence set forth in SEQ ID NO:4; or an amino acid other than tryptophan (e.g., valine) at a position aligning with position 1571 of the amino acid sequence set forth in SEQ ID NO:4.

In some embodiments, a modified AROM polypeptide is fused to a polypeptide catalyzing the first committed step of vanillin biosynthesis, 3-dehydroshikimate dehydratase (3DSD). A polypeptide having 3DSD activity and that is suitable for use in a fusion polypeptide includes the 3DSD polypeptide from *Podospora pauciseta, Ustilago maydis, Rhodoicoccus jostii, Acinetobacter* sp., *Aspergillus niger* or *Neurospora crassa*. See, GENBANK Accession Nos. CAD60599), XP_001905369.1, XP_761560.1, ABG93191.1, AAC37159.1, and XM_001392464.

For example, a modified AROM polypeptide lacking domain 5 can be fused to a polypeptide having 3DSD activity (e.g., a *Podospora pauciseta* 3DSD). SEQ ID NO:26 sets forth the amino acid sequence of such a protein and SEQ ID NO:27 sets forth the nucleic acid sequence encoding the protein.

Catechol-O-Methyl Transferase (COMT) Polypeptides

The COMT polypeptide according to the invention may, in certain embodiments be a caffeoyl-O-methyltransferase. In other embodiments, the COMT polypeptide is preferably a catechol-O-methyltransferase. More preferably, a COMT polypeptide of the invention is a mutant (COMT) polypeptide having improved meta hydroxyl methylation of protocatechuic aldehyde, protocatechuic acid and/or protocatechuic alcohol relative to that of the *Homo sapiens* COMT having the amino acid sequence set forth in SEQ ID NO:27.

Figure 3A:
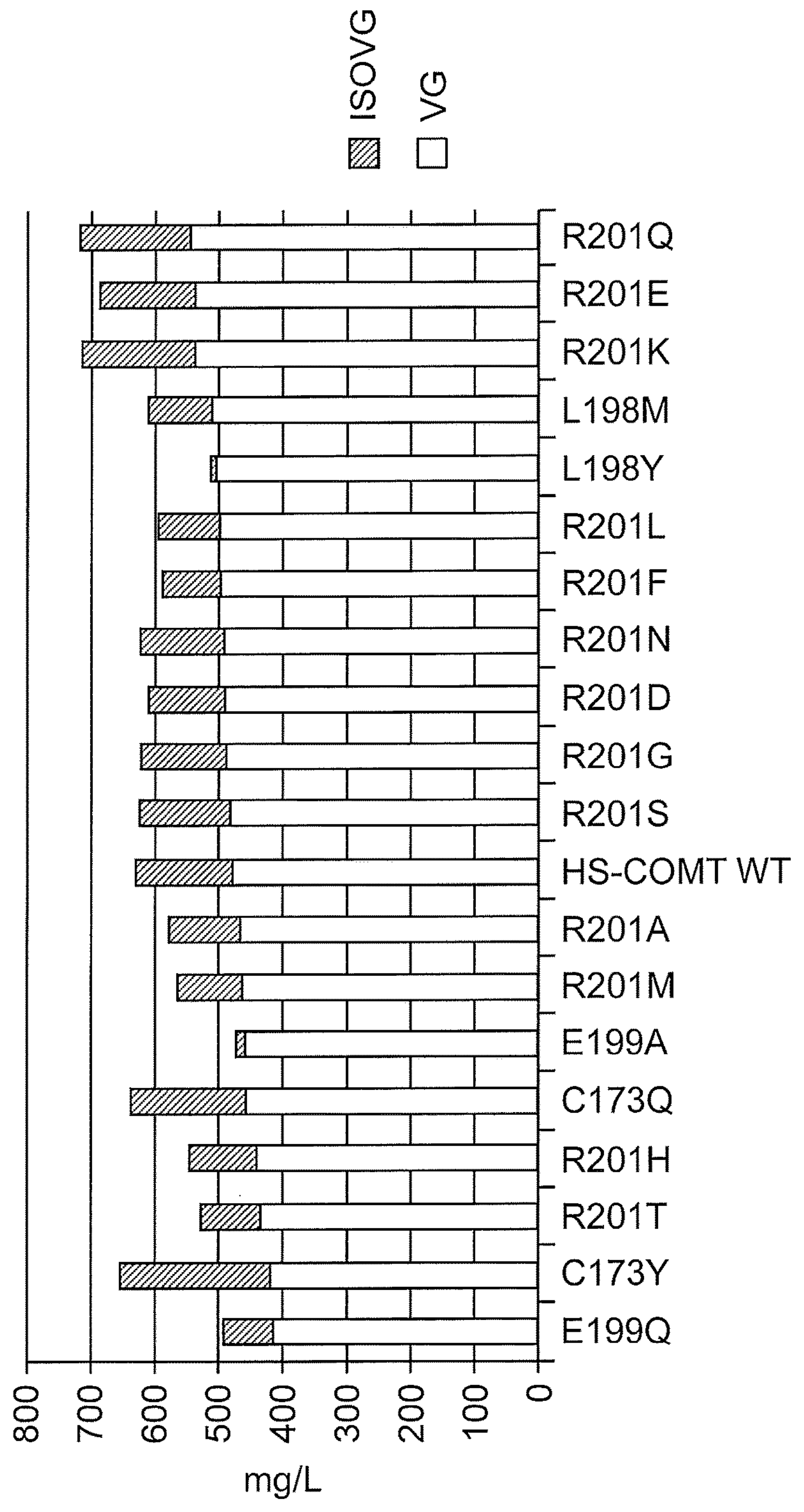
FIG. 3A shows production of vanillin (VG) and iso-vanillin (IsoVg) in yeast strain expressing various mutant COMT polypeptides.
Figure 3B:
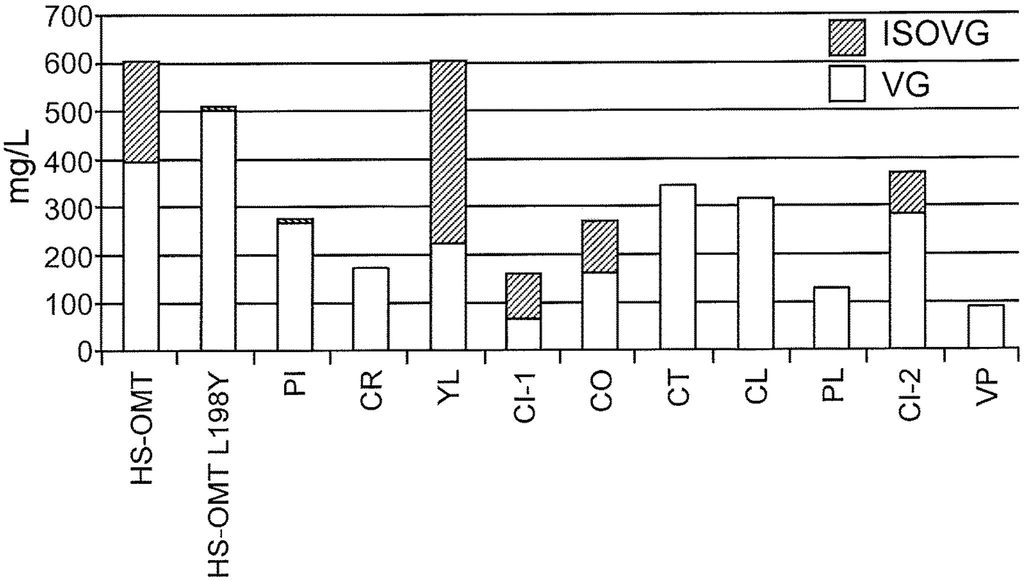
FIG. 3B and FIG. 3C show production of vanillin (VG) and iso-vanillin (IsoVg) by COMT polypeptides isolated from various sources as compared to human OMT (Hs-OMT) and the human L198Y OMT mutant (HS-OMT L198Y). *Phytophthera infestans* (PI), *Catharanthus roseus* (CR), *Yarrowia lipolytica* (YL), *Ciona intestinalis* GENBANK Accession Nos. XP_002121420 and XP_002131313 (CI-1 and CI-2), *Capsasproa owczarzaki* (CO), *Chaetomium therophilum* (CT), *Clavispora lusitaniae* (CL), *Paracoccidioides* sp. 'lutzii' Pb01 (PL), *Vanilla planifolia* (VP), *Coffea Arabica* (CA), *Rattus norvegicus* (RN), *Mus musculus* (MM), *Crenarchaeote* (CREN), *Mycobacterium vanbaleeni* (MV), or *Schizosaccharomyces pombe* (SP).
Figure 3C:
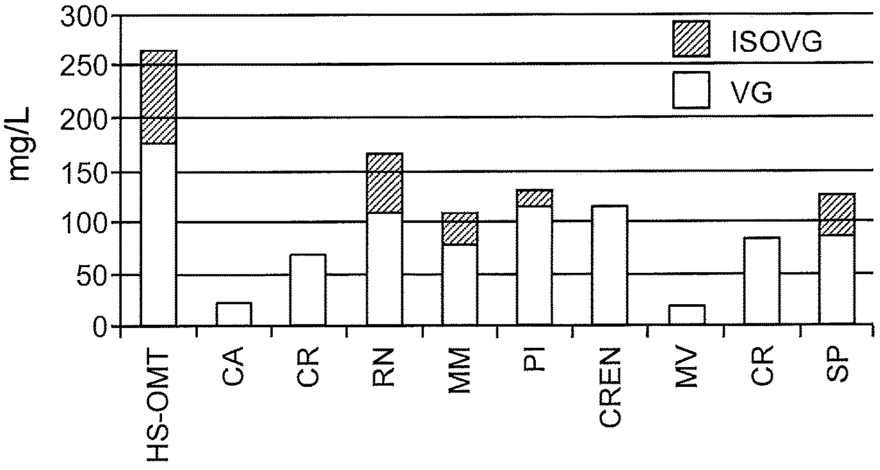

Non-limiting examples of COMT polypeptides that can be mutated in accordance with this invention include COMT polypeptides in the family classified under EC number 2.1.1.6, such as the *Homo sapiens* (Hs) polypeptide having the amino acid sequence set forth in SEQ ID NO:27 (see, also, GENBANK Accession No. NM_000754); an *Arabidopsis thaliana* polypeptide having the amino acid sequence set forth in SEQ ID NO:53 (GENBANK Accession No. AY062837); or a *Fragaria×ananassa* (strawberry) polypeptide having the amino acid sequence set forth in SEQ ID NO:54 (GENBANK Accession No. AF220491). Human COMT polypeptide exists as several variants and the COMT polypeptide may be any of these variants, however in a preferred embodiment the human COMT polypeptide is SEQ ID NO:27 or SEQ ID NO:55. Other suitable mammalian COMT polypeptides of use in this invention include, but are not limited to, those isolated from *Pan troglodytes* (GENBANK Accession No. XP 514984), *Macaca mulatta* (GENBANK Accession No. AFJ70145), *Equus caballus* (GENBANK Accession No. NP_001075303), *Canis lupus familiaris* (GENBANK Accession No. AAR20324), *Cricetulus griseus* (GENBANK Accession No. EGV97595), *Sus scrofa* (GENBANK Accession No. NP_001182259), and *Bos taurus* (GENBANK Accession No. NP_001095787). Other exemplary COMT polypeptides from plant and microorganism sources include, but are not limited to, those isolated from *Rosa chinensis* (GENBANK Accession No. CAD29457), *Prunus dulcis* (GENBANK Accession No. CAA58218), *Gossypium hirsutism* (GENBANK Accession No. ACT32028), *Jatropha curcas* (GENBANK Accession No. ACT87981), *Eucalyptus camaldulensis* (ADB82906), *Candida orthopsilosis* (GENBANK Accession No. CCG25047), *Pichia stipitis* (GENBANK Accession No. ABN67921), and *Spathaspora passalidarum* (GENBANK Accession No. EGW29958). In certain embodiments, the COMT polypeptide of the invention is obtained from *Phytophthera infestans* (GENBANK Accession No. XP_002899214), *Catharanthus roseus* (GENBANK Accession No. EGS21863), *Yarrowia lipolytica* (GENBANK Accession No. XP_500451), *Ciona intestinalis* (GENBANK Accession No. XP_002121420 or XP_002131313), *Capsasproa owczarzaki* (GENBANK Accession No. EFW46044), *Chaetomium therophilum* (GENBANK Accession No. EGS21863), *Clavispora lusitaniae* (GENBANK Accession No. XP_002899214), *Paracoccidioides* sp. 'lutzii' Pb01 (GENBANK Accession No. XP_002793380), *Vanilla planifolia* (SEQ ID NO:56), *Coffea Arabica* (GENBANK Accession No. AAN03726), *Rattus norvegicus* (GENBANK Accession No. NP_036663), *Mus musculus* (GENBANK Accession No. NP_031770), *Crenarchaeote* (GENBANK Accession No. ABZ07345), *Mycobacterium vanbaleeni* (GENBANK Accession No. ABM14078), or *Schizosaccharomyces pombe* (GENBANK Accession No. NP_001018770, which has been shown to exhibit the desired COMT activity (FIGS. 3B and 3C).

The term "COMT polypeptide" as used herein refers to any amino acid sequence that is at least 80 percent (e.g., at least 85, 90, 95, 96, 97, 98, 99, or 100 percent) identical to the Hs COMT sequence set forth in SEQ ID NO:27 and possesses the catechol-O-methyltransferase enzymatic activities of the wild-type Hs COMT polypeptide.

In one embodiment, the term "mutant COMT polypeptide," as used herein, refers to any polypeptide having an amino acid sequence which is at least 80 percent, such as at least 85 percent, for example at least 90 percent, such as at least 95 percent, for example at least 96 percent, such as at least 97 percent, for example at least 98 percent, such as at least 99 percent identical to the Hs COMT sequence set forth in SEQ ID NO:27 and is capable of catalyzing methylation of the —OH group at the meta position of protocatechuic acid and/or protocatechuic aldehyde, wherein the amino acid sequence of said mutant COMT polypeptide differs from SEQ ID NO:27 by at least one amino acid. In addition, the amino acid sequence of the mutant COMT polypeptide should differ from SEQ ID NO:53, SEQ ID NO:54 and SEQ ID NO:55 by at least one amino acid. It is preferred that the mutant COMT polypeptide differs by at least one amino acid from any sequence of any wild type COMT polypeptide.

In another embodiment of the invention, the term "mutant COMT polypeptide" refers to a polypeptide having an amino acid sequence, which is at least 80 percent, such as at least 85 percent, for example at least 90 percent, such as at least 95 percent, for example at least 96 percent, such as at least 97 percent, for example at least 98 percent, such as at least 99 percent identical to either SEQ ID NO:53 or SEQ ID NO:54 and is capable of catalyzing methylation of the —OH group at the meta position of protocatechuic acid and/or protocatechuic aldehyde, wherein the amino acid sequence of said mutant COMT polypeptide differs from each of SEQ ID NO:53 and SEQ ID NO:54 by at least one amino acid.

The mutant COMT polypeptides described herein can have one or more mutations (e.g., a substitution of one or more amino acids, a deletion of one or more amino acids, insertions of one or more amino acids, or combinations of substitutions, deletions, and insertions) in, for example, the substrate binding site. For example, a mutant COMT polypeptide can have one or more amino acid substitutions in the substrate binding site of human COMT.

In certain embodiments, a "mutant COMT polypeptide" of the invention differs from SEQ ID NO:27, SEQ ID NO:53, SEQ ID NO:54 or SEQ ID NO:55 by only one or two amino acid residues, wherein the differences between said mutant and wild-type proteins are in the substrate bind site.

As described herein, mutant COMT polypeptides can be used to improve biosynthesis of vanillin glucoside. For example, mutant COMT polypeptides can have one or more of the following properties: increased turnover; preferential methylation at the meta (3') position, rather than at the para (4') position such that production of vanillin is favored over isovanillin; or better specificity for the vanillin pathway substrates, protocatechuic acid and protocatechuic aldehyde. Mutant COMT polypeptides can be characterized in vitro using methylation assays or characterized in vivo in a recombinant host based on production of vanillic acid, vanillin, or vanillin glucoside.

The structures of iso-vanillin, vanillin, iso-vanillic acid and vanillic acid are as follows.

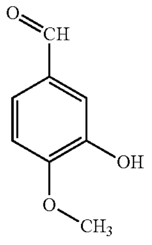

Iso-vanillin

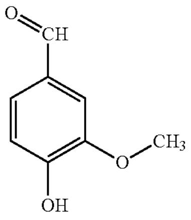

Vanillin

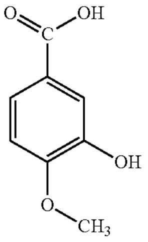

Iso-vanillic acid

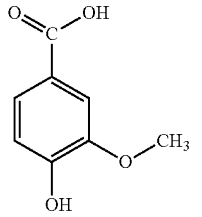

Vanillic acid

The wild-type Hs COMT lacks regioselective O-methylation of protocatechuic aldehyde and protocatechuic acid, indicating that the binding site of Hs COMT does not bind these substrates in an orientation that allows the desired regioselective methylation. Without being bound to a particular mechanism, the active site of Hs COMT is composed of the co-enzyme S-adenosyl methionine (SAM), which serves as the methyl donor, and the catechol substrate, which contains the hydroxyl to be methylated coordinated to $Mg^{2+}$ and proximal to Lys144. The O-methylation proceeds via an SN2 mechanism, where Lys144 serves as a catalytic base that deprotonates the proximal hydroxyl to form the oxyanion that attacks a methyl group from the sulfonium of SAM. See, for example, Zheng & Bruice (1997) *J. Am. Chem. Soc.* 119(35):8137-8145; Kuhn & Kollman (2000) *J. Am. Chem. Soc.* 122(11):2586-2596; Roca, et al. (2003) *J. Am. Chem. Soc.* 125(25):7726-37.

In one embodiment of the invention the invention provides a mutant COMT polypeptide, which is capable of catalyzing methylation of an —OH group of protocatechuic acid, wherein said methylation results in generation of at least 4 times more vanillic acid compared to iso-vanillic acid, preferably at least 5 times more vanillic acid compared to iso-vanillic acid, such as at least 10 times more vanillic acid compared to iso-vanillic acid, for example at least 15 times more vanillic acid compared to iso-vanillic acid, such as at least 20 times more vanillic acid compared to iso-vanillic acid, for example at least 25 times more vanillic acid compared to iso-vanillic acid, such as at least 30 times more vanillic acid compared to iso-vanillic acid; and which has an amino sequence which differs from SEQ ID NO:27 by at least one amino acid.

In addition to above mentioned properties, it is furthermore preferred that a mutant COMT polypeptide is capable of catalyzing methylation of an —OH group of protocatechuic aldehyde, wherein said methylation results in generation of at least 4, 5, 10, 15, 20, 25, or 30 times more vanillin compared to iso-vanillin; and/or is capable of catalyzing methylation of an —OH group of protocatechuic alcohol, wherein said methylation results in generation of at least 4, 5, 10, 15, 20, 25, or 30 times more vanillyl alcohol compared to iso-vanillyl alcohol.

To determine whether a given mutant COMT polypeptide is capable of catalyzing methylation of an —OH group of protocatechuic acid, wherein said methylation results in generation of at least X times more vanillic acid compared to iso-vanillic acid, an in vitro assay can be conducted. In such an assay, protocatechuic acid is incubated with a mutant COMT polypeptide in the presence of a methyl donor and subsequently the level of generated iso-vanillic acid and vanillic acid is determined. Said methyl donor may for example be S-adenosylmethionine. More preferably, this may be determined by generating a recombinant host harboring a heterologous nucleic acid encoding the mutant COMT polypeptide to be tested, wherein said recombinant host furthermore is capable of producing protocatechuic acid. After cultivation of the recombinant host, the level of generated iso-vanillic acid and vanillic acid may be determined. In relation to this method it is preferred that said heterologous nucleic acid encoding the mutant COMT polypeptide to be tested is operably linked to a regulatory region allowing expression in said recombinant host. Furthermore, it is preferred that the recombinant host expresses at least one 3DSD and at least one ACAR, which preferably may be one of the 3DSD's and ACAR's described herein. In embodiments where the recombinant host expresses an ACAR capable of catalyzing conversion of vanillic acid to vanillin, then the method may also include determining the level of generated vanillin and iso-vanillin. The recombinant host may also express at least one UGT capable of catalyzing glucosylation of vanillin and isovanillin, in which case the levels of vanillin-glucoside and iso-vanillin-glucoside may be determined instead of the levels of vanillin and iso-vanillin, respectively. Alternatively, this may be determined by generating a recombinant host harboring a heterologous nucleic acid encoding the mutant COMT polypeptide to be tested, and feeding protocatechuic acid to said recombinant host, followed by determining the level of generated iso-vanillic acid and vanillic acid.

Similarly, an in vitro assay or a recombinant host cell can be used to determine whether a mutant COMT polypeptide is capable of catalyzing methylation of an —OH group of protocatechuic aldehyde, wherein said methylation results in generation of at least X times more vanillin compared to iso-vanillin. However, in this assay, protecatechuic aldehyde is used as starting material and the level of vanillin and iso-vanillin is determined.

Likewise, an in vitro assay or a recombinant host cell can be used to determine whether a given mutant COMT polypeptide is capable of catalyzing methylation of an —OH group of protocatechuic alcohol, wherein said methylation results in generation of at least X times more vanillyl alcohol compared to iso-vanillyl alcohol. However, in this assay, protecatechuic alcohol is used as starting material and the level of vanillyl alcohol and iso-vanillyl alcohol is determined.

The level of isovanillin and vanillin may be determined by any suitable method useful for detecting these compounds, wherein said method can distinguish between iso-vanillin and vanillin. Such methods include for example HPLC. Similarly, the level of iso-vanillic acid, vanillic acid, iso-vanillyl alcohol and vanillyl alcohol may be determined using any suitable method useful for detecting these compounds, wherein said method can distinguish between iso-vanillin and vanillin. Such methods include for example HPLC.

For substrates of the dimensions of protocatechuic aldehyde and protocatechuic acid, the boundary of the substrate binding site of Hs COMT was found to be formed by the following hydrophobic residues: Trp38, Met40, Cys173, Pro174, Trp143, and Leu198. An additional hydrophilic residue that may influence binding is Arg201. The hydroxyl of the catechol that is not methylated hydrogen bonds with Glu199.

In accordance with this mechanism, for meta-position methylation of protocatechuic aldehyde and protocatechuic acid to occur, these substrates must be bound in an orientation that places the meta hydroxyl so that it is coordinated to $Mg^{2+}$ and proximal to Lys144, whereas the para hydroxyl is proximal to Glu199. The observed lack of this desired regioselectivity in wild-type Hs COMT suggests that this binding orientation does not preferentially occur. One or more amino acids can be substituted for the binding site residues of Hs COMT to allow a binding orientation of the substrates that promotes the desired meta O-methylation of protocatechuic aldehyde and protocatechuic acid.

Therefore, this invention also includes a method for identifying COMT polypeptides with improved substrate specificity. In particular, such a method provides computational methodology for identifying residue mutations that confer improved meta O-methylation by a COMT polypeptide. The method includes several distinct steps. In particular, one method of identifying optimum mutations includes the steps of (a) selecting a protein structure of a COMT polypeptide; (b) docking substrates protocatechuic acid and protocatechuic aldehyde to the protein structure of the COMT polypeptide determined in (a) to deduce the different conformations which promote regioselective meta or para O-methylation; (c) identifying binding site mutations proximal to protocatechuic acid and protocatechuic aldehyde substrates; (d) performing in silico mutational analysis on each residue identified in (c); (e) ranking candidate residue mutations for each position from (d) based on predicted conformations of substrate of meta or para O-methylation; and (f) selecting best scoring mutations for each candidate residue identified in (c).

As discussed above, the COMT polypeptide can be in the COMT family classified under EC number 2.1.1.6, catechol O-methyl transferase. As such, one skilled in the art would appreciate that, in addition to Hs COMT, the method can be applied to any species of COMT within this classification, wherein such proteins will have similar binding site residues. In some embodiments, the method is applied to the *Arabidopsis* or strawberry COMT (SEQ ID NO:54 and SEQ ID NO:54, respectively). While each of the method steps are described in more detail with respect to Hs COMT, it will be appreciated that similar method steps can be performed with other COMT polypeptides.

In step (a), a COMT protein structure is selected. Protein structures of Hs COMT are publically available from the Protein Data Bank and can be assessed for utility based upon resolution, inclusion of mutations, and other sequence variations that may been introduced to afford crystallization. Other factors that can be considered in choosing a structure include whether or not the structure includes a substrate bound to the protein, or the nature of the substrate bound to the protein. Crystal structure code 3BWM (RCSB Protein Data Bank) is a particularly useful structure for Hs COMT, and was used in the methods described herein. One skilled in the art would appreciate that other Hs COMT crystal structure can be used as inputs to modeling procedures.

In step (b), the substrates of interest, e.g., protocatechuic acid and protocatechuic aldehyde, are docked to the protein structure. Docking is a term denoting a computational approach implemented in a variety of algorithms of predicting a likely conformation of a selected small molecule in a protein binding site. The technique typically calculates a binding score to provide the basis to evaluate the goodness of fit and predicted binding energy of interaction. The docking program used to derive the substrate conformations used in the current procedure is ProtoScreen (Haydon, et al. (2008) *Science* 321:1673-1675). The method creates binding scores according to the ProtoScore algorithm (Bhurruth-Alcor, et al. (2011) *Org. Biomol. Chem.* 9:1169-1188). One skilled in the art will appreciate that other docking programs may be used in this method step to identify suitable binding conformations of protocatechuic acid and protocatechuic aldehyde substrates in Hs COMT (or other COMT family member).

In step (c), mutational analysis is performed. This can include several substeps such as (i) identifying a first residue to be mutated; (ii) identifying a residue to mutate to from list of suitable amino acids; (iii) for each residue in (ii), searching a rotamer library for conformational candidates; (iv) mutating the residue from (i) with each of the new residue side chain rotamer selections from (iii); (v) minimizing protein complex conformation; (vi) scoring each rotamer candidate in (iv) with various calculations of mutant-substrate, mutant-protein, mutant-solvent and substrate-solvent energies with different conformations of protocatechuic acid or aldehyde allowing for energy comparisons between where the substrate is being modified either at the meta or the para position; and (vii) ranking rotamer selections from (iii) and then highest scoring amino acid mutants from (ii).

In substep (i), each of the residues to be mutated are analyzed in turn.

In substep (ii), a residue to mutate is chosen from a deterministic list of available amino acids. By default this list is the standard 20 amino acids found in nature, but could include other non-natural amino acids.

In substep (iii), all rotamers are identified in a rotamer library that matches the mutant amino acid identity. A rotamer library is a precomputed set of preferred conformations of standard amino acid side chains in a useable 3D format. Such libraries are commonly used in protein structural analysis work, and are included in most commercially available molecular modeling packages. The set of rotamers that match the identity of the mutating residue are selected for substep (iv).

In substep (iv), the selected protein residue is swapped for each of the rotamers identified in (iii). This involves manipulating the computational representation of the protein residue atoms such that the starting residue side chain atoms are deleted before the incoming selected rotamer from (iii) are connected to the alpha carbon position using vector mathematics. This method is repeated for each candidate rotamer to arrive at a list of 3D representations of the protein each varying only by differing rotamer conformations at a single residue position.

In substep (v), the protein-substrate complexes derived in (iv) are subject to forcefield minimizations. In a particularly useful embodiment, this forcefield is AMBER99 with AM1-BCC charges applied to the substrate. In another aspect of the method, a Born solvation term is used. The protein backbone can be tethered using wall constraints, while side chains remain unconstrained. This has the effect of reducing overall protein motion but allowing the effect of the individual residue mutation on neighboring residues to be explored. One skilled in the art will appreciate that various commercially available molecular modeling packages are capable of performing these tasks.

In substep (vi), the resulting protein-complex conformations are subject to energetic calculations to determine the viability of the individual mutant conformations. This includes individually calculating the wild-type residue interaction energy with the substrate, protein environment and solvent and then performing the same calculations with the mutated residue conformation. The calculations are determined for both (meta and para reacting) conformations of the substrate. This method step thus identifies mutations which have favorable binding energies for the substrate in the meta reacting pose compared to the para activating pose. The energies are calculated using forcefield based terms. In one embodiment, the forcefield is AMBER99 and the interaction energy between an amino acid and the protein-substrate environment is described by equation 1.

$$E_{non-bonded} = E_{van-der-Waals} + E_{electrostatic} \quad \text{(Equation 1)}$$

where $$E_{van-der-Waals} = \sum_{\substack{nonbonded\\pairs}} \left( \frac{A_{ik}}{r_{ik}^{12}} - \frac{C_{ik}}{r_{ik}^{6}} \right)$$

$$E_{electrostatic} = \sum_{\substack{nonbonded\\pairs}} \frac{q_i q_k}{D r_{ik}}$$

One skilled in the art will appreciate that other similar equations can be implemented to derive interaction energies suitable for this differential energetic analysis of different substrate-mutated amino acid poses.

In substep (vii), mutant amino acids are selected based upon favorable binding energies of substrate bound in the meta reacting predicted pose compared to the para reacting predicted pose. These calculations thus determines which amino acid mutations are likely to promote meta regioselective O-methylation.

In step (iv), step (iii) is repeated until a list of energy values is outputted for each of the binding site residues to be mutated.

In step (v), the list of energy values derived from step (iv) is ranked by the differential in energy between each mutation with where the substrate is in the meta reacting position compared to the para reacting position. The entries at the top of this list represent where mutations favor meta O-methylation over para O-methylation.

In step (vi), a limited number of such candidates from step (v) are selected based on the energy values. Mutations are not selected where (1) mutations are energetically unfavorable or (2) where mutations are not predicted to alter regioselectivity.

As described herein, application of the method described above to Hs COMT resulted in the identification of a set of mutations that are designed to improve enzyme regioselectivity O-methylation. The mutations can be used independently or in combination.

In the membrane bound isoform of Hs COMT, the equivalent residue numbers are those of soluble Hs COMT plus fifty. Therefore residues described or replaced in soluble Hs COMT are also inferred to be described or replaced at the residue number plus fifty in membrane bound Hs COMT.

In one embodiment, the invention provides a mutant COMT polypeptide, which (1) has an amino acid sequence sharing at least percent, such as at least 85 percent, for example at least 90 percent, such as at least 95 percent, for example at least 96 percent, such as at least 97 percent, for example at least 98 percent, such as at least 99 percent sequence identity with SEQ ID NO:27 determined over the entire length of SEQ ID NO:27; and (2) has at least one amino acid substitution at a position aligning with positions 198 to 199 of SEQ ID NO:27, which may be any of the amino acid substitutions described herein below; and (3) is capable of catalyzing methylation of an —OH group of protocatechuic acid, wherein said methylation results in generation of at least 4, 5, 10, 15, 20, 25 or 30 times more vanillic acid compared to iso-vanillic acid. In addition these characteristics, said mutant COMT polypeptide may also be capable of catalyzing methylation of an —OH group of protocatechuic aldehyde, wherein said methylation results in generation of at least 4, 5, 10, 15, 20, 25 or 30 times more vanillin compared to iso-vanillin; and/or be capable of catalyzing methylation of an —OH group of protocatechuic alcohol, wherein said methylation results in generation of at least 4, 5, 10, 15, 20, 25, or 30 times more vanillyl alcohol compared to iso-vanillyl alcohol.

Thus, the mutant COMT polypeptide may in one preferred embodiment have an amino acid substitution at the position aligning with position 198 of SEQ ID NO:27. Accordingly, the mutant COMT polypeptide may be a mutant COMT polypeptide with the characteristics outlined above, wherein said substitution is a substitution of the leucine at the position aligning with position 198 of SEQ ID NO:27 with another amino acid having a lower hydropathy index. For example, the mutant COMT polypeptide may be a mutant COMT polypeptide with characteristics as outlined above, wherein said substitution is a substitution of the leucine at the position aligning with position 198 of SEQ ID NO:27 with another amino acid having a hydropathy index lower than 2. Thus, the mutant COMT polypeptide may be a mutant COMT polypeptide with characteristics as outlined above, wherein said substitution is a substitution of the leucine at the position aligning with position 198 of SEQ ID NO:27 with an Ala, Arg, Asn, Asp, Cys, Glu, Gln, Gly, His, Lys, Met, Phe, Pro, Ser, Thr, Trp or Tyr, for example Ala, Arg, Asn, Asp, Glu, Gln, Gly, His, Lys, Met, Pro, Ser, Thr, Trp or Tyr. However, preferably said substitution is a substitution of the leucine at the position aligning with position 198 of SEQ ID NO:27 with tyrosine. Substitution of the leucine aligning with position 198 of SEQ ID NO:27 with methionine increased regioselectivity of meta>para O-methylation for protocatechuic aldehyde.

In another preferred embodiment, the mutant COMT polypeptide may have an amino acid substitution at the position aligning with position 199 of SEQ ID NO:27. Accordingly, the mutant COMT polypeptide may be a mutant COMT polypeptide with characteristics as outlined above, wherein said substitution is a substitution of the glutamic acid at the position aligning with position 199 of SEQ ID NO:27 with another amino acid, which has either a neutral or positive side-chain charge at pH 7.4. Thus, the mutant COMT polypeptide may be a mutant COMT polypeptide with characteristics as outlined above, wherein said substitution is a substitution of the glutamic acid at the position aligning with position 199 of SEQ ID NO:27 with Ala, Arg, Asn, Cys, Gln, Gly, His, Ile, Leu, Lys, Met, Phe, Pro, Ser, Thr, Trp, Tyr or Val. However, preferably said substitution is a substitution of the glutamic acid at the position aligning with position 199 of SEQ ID NO:27 with an alanine or glutamine. Substitution of the glutamic acid aligning with position 199 of SEQ ID NO:27 with alanine or glutamine increased regioselectivity of meta>para O-methylation for protocatechuic aldehyde.

For example, a mutant COMT polypeptide can have one or more of the following mutations: a substitution of a tryptophan, tyrosine, phenylalanine, glutamic acid, or arginine for the leucine at a position aligning with position 198 of the amino acid sequence set forth in SEQ ID NO:27; a substitution of an arginine, lysine, or alanine for methionine at a position aligning with position 40 of the amino acid sequence set forth in SEQ ID NO:27; a substitution of a tyrosine, lysine, histidine, or arginine for the tryptophan at a position aligning with position 143 of the amino acid sequence set forth in SEQ ID NO:27; a substitution of an isoleucine, arginine, or tyrosine for the proline at a position aligning with position 174 of the amino acid sequence set forth in SEQ ID NO:27; a substitution of an arginine or lysine for tryptophan at a position aligning with position 38 of the amino acid sequence set forth in SEQ ID NO:27; a substitution of a phenylalanine, tyrosine, glutamic acid, tryptophan, or methionine for cysteine at a position aligning with position 173 of the amino acid sequence set forth in SEQ ID NO:27; and/or a substitution of a serine, glutamic acid, or aspartic acid for arginine at a position aligning with position 201 of the amino acid sequence set forth in SEQ ID NO:27.

In one embodiment, a mutant COMT polypeptide contains substitution of tryptophan for leucine at a position aligning with position 198. This mutation may increase regioselectivity of meta>para O-methylation for protocatechuic acid. Modeling of the protein binding site of a COMT polypeptide containing a L198W mutation, indicates that a steric clash can occur between the mutated residue and the substrate. This steric clash does not occur in the meta reacting conformation as the carboxylic acid of the substrate is distal to this residue.

In another embodiment of the invention, the mutant COMT polypeptide is a polypeptide of SEQ ID NO:27, wherein the amino acid at position 198 has been substituted with an amino acid having a lower hydropathy index than leucine. For example, the mutant COMT polypeptide may be a polypeptide of SEQ ID NO:27, wherein the leucine at the position 198 has been substituted with an amino acid having a hydropathy index lower than 2. Thus, the mutant COMT polypeptide may be a polypeptide of SEQ ID NO:1, wherein the leucine at position 198 has been substituted with an Ala, Arg, Asn, Asp, Glu, Gln, Gly, His, Lys, Met, Pro, Ser, Thr, Trp or Tyr, preferably Met or Tyr.

In another preferred embodiment, the mutant COMT polypeptide may be a polypeptide of SEQ ID NO:27, wherein the amino acid at position 199 has been substituted with another amino acid, which has either a neutral or positive side-chain charge at pH 7.4. Thus, the mutant COMT polypeptide may be a polypeptide of SEQ ID NO:27 where the glutamic acid at the position 199 has been substituted with Ala, Arg, Asn, Cys, Gln, Gly, His, Ile, Leu, Lys, Met, Phe, Pro, Ser, Thr, Trp, Tyr or Val, preferably Ala or Gln.

In some embodiments, a mutant COMT polypeptide has two or more mutations. For example, 2, 3, 4, 5, 6, or 7 of the residues in the substrate binding site can be mutated. For example, in one embodiment, a mutant COMT polypeptide can have a substitution of an arginine or lysine for methionine at a position aligning with position 40 of the amino acid sequence of SEQ ID NO:27; a substitution of a tyrosine or histidine for tryptophan at a position aligning with position 143 of the amino acid sequence of SEQ ID NO:27; a substitution of an isoleucine for proline at a position aligning with position 174 of the amino acid sequence of SEQ ID NO:27, and a substitution of an arginine or lysine for tryptophan at position 38. A mutant COMT polypeptide also can have a substitution of lysine or arginine for tryptophan at a position aligning with position 143 of the amino acid sequence of SEQ ID NO:27 and a substitution of an arginine or tyrosine for proline at position 174 of SEQ ID NO:27. A mutant COMT polypeptide also can have a substitution of a phenylalanine, tyrosine, glutamic acid, tryptophan, or methionine for cysteine at a position aligning with position 173 of the amino acid sequence set forth in SEQ ID NO:27, a substitution of an alanine for methionine at a position aligning with position 40 of the amino acid sequence set forth in SEQ ID NO:27, and a substitution of a serine, glutamic acid, or aspartic acid for the arginine at a position aligning with position 201 of the amino acid sequence set forth in SEQ ID NO:27. It is also possible that the mutant COMT polypeptide has a substitution of the leucine at a position aligning with position 198 of SEQ ID NO:27 as well as a substitution of the glutamic acid at a position aligning with position 199 of SEQ ID NO:27. Said substitutions may be any of the substitutions described in this section above, It is also possible that the mutant COMT polypeptide has a substitution of the leucine at a position aligning with position 198 of SEQ ID NO:27 as well as a substitution of the arginine at a position aligning with position 201 of SEQ ID NO:27. Said substitutions may be any of the substitutions described in this section above.

Percent Identity

The sequence identities given herein are preferably sequence identity over the entire length of the reference sequence. Accordingly, sequence identity to the amino acid sequence provided as SEQ ID NO:4 or SEQ ID NO:27 herein is sequence identity over the entire length of SEQ ID NO:4 or SEQ ID NO:27, respectively.

Percent identity can be determined as follows. A reference sequence (e.g., a nucleic acid sequence or an amino acid sequence set forth in SEQ ID NO:4 or SEQ ID NO:27) is aligned to one or more candidate sequences using the computer program ClustalW (version 1.83, default parameters), which allows alignments of nucleic acid or polypeptide sequences to be carried out across their entire length (global alignment). Chema et al. (2003) *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pair-wise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pair-wise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences.

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Amino Acid Substitutions

Amino acid substitutions can be conservative or non-conservative. Conservative amino acid substitutions replace an amino acid with an amino acid of the same class, whereas non-conservative amino acid substitutions replace an amino acid with an amino acid of a different class. Examples of conservative substitutions include amino acid substitutions within the following groups: (1) glycine and alanine; (2) valine, isoleucine, and leucine; (3) aspartic acid and glutamic acid; (4) asparagine, glutamine, serine, and threonine; (5) lysine, histidine, and arginine; and (6) phenylalanine and tyrosine.

Non-conservative amino acid substitutions may replace an amino acid of one class with an amino acid of a different class. Non-conservative substitutions can make a substantial change in the charge or hydrophobicity of the gene product. Non-conservative amino acid substitutions also can make a substantial change in the bulk of the residue side chain, e.g., substituting an alanine residue for an isoleucine residue. Examples of non-conservative substitutions include the substitution of a basic amino acid for a non-polar amino acid or a polar amino acid for an acidic amino acid. One of ordinary skill in the art will appreciate that similar amino acids can be substituted for the mutants described herein.

Nucleic Acids

This document also provides isolated nucleic acids encoding the mutant AROM and COMT polypeptides. An "isolated nucleic acid" refers to a nucleic acid that is separated from other nucleic acid molecules that are present in a genome, including nucleic acids that normally flank one or both sides of the nucleic acid in a genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Nucleic acids encoding AROM or COMT polypeptides can be modified using common molecular cloning techniques (e.g., site-directed mutagenesis) to generate mutations at particular positions of the encoded polypeptide (e.g., positions aligning with position 1349, 1366, 1370, 1387, 1392, 1441, 1458, 1500, 1533, or 1571 of the AROM amino acid sequence set forth in SEQ ID NO:4; or positions aligning with position 38, 40, 143, 173, 174, 198, or 201 of the soluble form of the human COMT amino acid sequence set forth in SEQ ID NO:27). Nucleic acid molecules can include a single nucleotide mutation or more than one mutation, or more than one type of mutation. Polymerase chain reaction (PCR) and nucleic acid hybridization techniques can be used to identify nucleic acids encoding AROM polypeptides having altered amino acid sequences.

In some embodiments, a nucleic acid molecule encoding a mutant polypeptide of this invention can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the AROM or COMT polypeptide such that the encoded tag is located at either the carboxyl or amino terminus of the AROM or COMT polypeptide. Non-limiting examples of encoded tags include green fluorescent protein (GFP), glutathione S transferase (GST), HIS tag, and FLAG tag (Kodak, New Haven, Conn.). Other examples of tags include a chloroplast transit peptide, a mitochondrial transit peptide, an amyloplast peptide, signal peptide, or a secretion tag.

Polypeptides (mutant or wild-type) of this invention can be produced using any method. For example, polypeptides can be produced by chemical synthesis. Alternatively, polypeptides described herein can be produced by standard recombinant technology using heterologous expression vectors encoding polypeptides. Expression vectors can be introduced into host cells (e.g., by transformation or transfection) for expression of the encoded polypeptide, which then can be purified. Expression systems that can be used for small or large scale production of polypeptides include, without limitation, microorganisms such as bacteria (e.g., *E. coli* and *B. subtilis*) transformed with recombinant bacteriophage DNA, plasmid DNA, or cosmid DNA expression vectors containing the nucleic acid molecules described herein, and yeast (e.g., *S. cerevisiae* or *S. pombe*) transformed with recombinant yeast expression vectors containing the nucleic acid molecules described herein. Useful expression systems also include insect cell systems infected with recombinant virus expression vectors (e.g., baculovirus) containing the nucleic acid molecules described herein, and plant cell systems infected with recombinant virus expression vectors (e.g., tobacco mosaic virus) or transformed with recombinant plasmid expression vectors (e.g., Ti plasmid) containing the nucleic acid molecules described herein. Polypeptides of this invention also can be produced using mammalian expression system harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids described herein. Polypeptides of this invention can have an N-terminal or C-terminal tag as discussed above.

Recombinant Hosts

This invention also features recombinant hosts. As used herein, the term recombinant host is intended to refer to a host, the genome of which has been augmented by at least one incorporated DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. However, autonomous or replicative plasmids or vectors can also be used within the scope of this invention. Moreover, the present invention can be practiced using a low copy number, e.g., a single copy, or high copy number (as exemplified herein) plasmid or vector.

Generally, the introduced DNA is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

A recombinant gene encoding a polypeptide described herein includes the coding sequence for that polypeptide, operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. The term "heterologous nucleic acid" as used herein, refers to a nucleic acid introduced into a recombinant host, wherein said nucleic acid is not naturally present in said host. Thus, if the recombinant host is a microorganism, the coding sequence can be from other prokaryotic or eukaryotic microorganisms, from plants or from animals. n some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically includes at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes, for example one or more heterologous nucleic acids, can be combined in a recombinant nucleic acid construct in "modules" useful for a discrete aspect of vanillin and/or vanillin glucoside production. Combining a plurality of genes or heterologous nucleic acids in a module, facilitates the use of the module in a variety of species. For example, a vanillin gene cluster can be combined such that each coding sequence is operably linked to a separate regulatory region, to form a vanillin module for production in eukaryotic organisms. Alternatively, the module can express a polycistronic message for production of vanillin and/or vanillin glucoside in prokaryotic hosts such as species of *Rodobacter, E. coli, Bacillus* or *Lactobacillus*. In addition to genes useful for vanillin or vanillin glucoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

Recombinant hosts described herein express mutant AROM polypeptides and/or mutant COMT polypeptides. Thus, in one aspect, the present invention relates to a recombinant host harboring a heterologous nucleic acid encoding a mutant AROM polypeptide and/or a mutant COMT polypeptide, which may be any of the mutant polypeptides described herein. In particular, the invention relates to a recombinant host harboring a heterologous nucleic acid encoding said mutant AROM polypeptide and/or mutant COMT polypeptide, wherein said nucleic acid is operably linked to a regulatory region allowing expression in said recombinant host.

Such hosts further can include additional genes or biosynthetic modules to produce vanillin or vanillin glucoside, improve efficiency with which energy and carbon sources are converted to vanillin and its glucoside, and/or to enhance productivity from the cell culture or plant. Such additional biosynthetic modules can include one or more of a gene encoding a 3DSD polypeptide, a gene encoding a phosphopantetheinyl transferase (PPTase), and a gene encoding a UGT polypeptide. See FIG. 1. These genes may be endogenous genes or recombinant genes. In addition, when the host cell harbors a heterologous nucleic acid encoding a mutant AROM polypeptide, the host cell may further include a wild-type OMT gene. Likewise, when the host cell harbors a heterologous nucleic acid encoding a mutant COMT polypeptide, the host cell may further include a wild-type AROM gene. Alternatively, the host cell may harbor heterologous nucleic acids encoding a mutant COMT polypeptide and a mutant AROM polypeptide, as described herein. In addition, the host can further express a Vanillyl Alcohol Oxidase (VAO) enzyme.

Suitable 3DSD polypeptides are known. A 3DSD polypeptide according to the present invention may be any enzyme with 3-dehydroshikimate dehydratase activity. Preferably, the 3DSD polypeptide is an enzyme capable of catalyzing conversion of 3-dehydro-shikimate to protocatechuate and $H_2O$. A 3DSD polypeptide according to the present invention is preferably an enzyme classified under EC 4.2.1.118. For example, a suitable polypeptide having 3DSD activity includes the 3DSD polypeptide made by *Podospora pauciseta, Ustilago maydis, Rhodoicoccus jostii, Acinetobacter* sp., *Aspergillus niger* or *Neurospora crassa*. See, GENBANK Accession Nos. CAD60599, XP_001905369.1, XP_761560.1, ABG93191.1, AAC37159.1, and XM_001392464. Thus, the recombinant host may include a heterologous nucleic acid encoding the 3DSD polypeptide of *Podospora anserina, Ustilago maydis, Rhodoicoccus jostii, Acinetobacter* sp., *Aspergillus niger* or *Neurospora crassa* or a functional homologue of any of the aforementioned sharing at least 80%, such as at least 85%, for example at least 90%, such as at least 95%, for example at least 98% sequence identity therewith.

As discussed herein, suitable wild-type OMT polypeptides are known. For example, a suitable wild-type OMT polypeptide includes the OMT made by *H. sapiens, A. thaliana*, or *Fragaria×ananassa* (see, GENBANK Accession Nos. NM_000754, AY062837; and AF220491), as well as OMT polypeptides isolated from a variety of other mammals, plants or microorganisms.

Likewise, suitable wild-type AROM polypeptides are known. For example, suitable wild-type AROM polypeptides include AROM made by *S. cerevisiae, S. pombe, S. japonicas, N. crassa*, and *Y. lipolytica*. See GENBANK Accession Nos. X06077, NP_594681.1, XP_002171624 and XP_956000.

Suitable ACAR polypeptides are known. An ACAR polypeptide according to the present invention may be any enzyme having aromatic carboxylic acid reductase activity. Preferably, the ACAR polypeptide is an enzyme capable of catalyzing conversion protocatechuic acid to protocatechuic aldehyde and/or conversion of vanillic acid to vanillin. An ACAR polypeptide according to the present invention is preferably an enzyme classified under EC 1.2.1.30. For example a suitable ACAR polypeptide is made by *Nocardia* sp. See, e.g., GENBANK Accession No. AY495697. Thus, the recombinant host may include a heterologous nucleic acid encoding the ACAR polypeptide of *Nocardia* sp. or a functional homologue thereof sharing at least 80%, such as at least 85%, for example at least 90%, such as at least 95%, for example at least 98% sequence identity therewith.

Suitable PPTase polypeptides are known. A PPTase polypeptide according to the present invention may be any enzyme capable of catalyzing phosphopantetheinylation. Preferably, the PPTase polypeptide is an enzyme capable of catalyzing phosphopantetheinylation of ACAR. For example, a suitable PPTase polypeptide is made by *E. coli, Corynebacterium glutamicum*, or *Nocardia farcinica*. See GENBANK Accession Nos. NP_601186, BAA35224, and YP_120266. Thus, the recombinant host may include a heterologous nucleic acid encoding the PPTase polypeptide of *E. coli, C. glutamicum*, or *N. farcinica* or a functional homologue of any of the aforementioned sharing at least 80%, such as at least 85%, for example at least 90%, such as at least 95%, for example at least 98% sequence identity therewith.

Glucosylation of vanillin is particularly useful. Vanillin-β-D-glucoside is the storage form of vanillin found in the vanilla pod. It is non-toxic to most organisms, including yeast, and has a higher solubility in water, as compared to vanillin. In addition, the formation of vanillin-β-D-glucoside most likely directs the biosynthesis toward vanillin production. UGT72E2 (Hansen, et al. (2009) *Appl. Environ. Microbiol.* 75:2765-27740) exhibited high substrate specificity toward vanillin. In concordance with this observation, its expression in the vanillin producing *S. cerevisiae* strain resulted in almost all vanillin being converted into vanillin-β-D-glucoside. The ability to turn vanillin into vanillin-β-D-glucoside in vivo is important, because microbial production of non-glucosylated vanillin beyond the 0.5-1 g/liter scale would be hampered by the toxicity of free vanillin. Glucosylation serves to circumvent the inhibitory effect.

Accordingly, the recombinant host of this invention also expresses a UGT polypeptide. A UGT polypeptide may be any UDP-Glucose:Aglycon-Glucosyltransferase. Preferably the UGT polypeptides can catalyze the glucosylation of vanillin (i.e., to produce vanillin beta-D-glucoside). Thus, the UGT polypeptide may be a Family 1 glycosyltransferease. Preferred UGT polypeptides according to the invention are classified under EC 2.4.1. Suitable UGT polypeptides include the UGT71C2, UGT72B1, UGT72E2, UGT84A2, UGT89B1, UGT85B1, and arbutin synthase polypeptides. See, e.g., GENBANK Accession Nos. AC0005496, NM_116337, and NM_126067. The *A. thaliana* UGT72E2 is particularly useful (see, e.g., Hansen, et al. (2009) supra). Thus, the recombinant host may include a heterologous nucleic acid encoding the UGT71C2, UGT72B1, UGT72E2, UGT84A2, UGT89B1, UGT85B1, or arbutin synthase or a functional homologue of any of the aforementioned sharing at least 80%, such as at least 85%, for example at least 90%, such as at least 95%, for example at least 98% sequence identity therewith. Other useful UGTs are described in WO 01/40491.

As a further embodiment of this invention, a VAO enzyme (EC 1.1.3.38) can also be expressed by host cells to oxidize any formed vanillyl alcohol into vanillin. VAO enzymes are known in the art and include, but are not limited to enzymes from filamentous fungi such as *Fusarium monilifomis*

(GENBANK Accession No. AFJ11909) and *Penicillium simplicissium* (GENBANK Accession No. P56216; Benen, et al. (1998) *J. Biol. Chem.* 273:7865-72) and bacteria such as Modestobacter marinus (GENBANK Accession No. YP_006366868), *Rhodococcus jostii* (GENBANK Accession No. YP_703243.1) and *R. opacus* (GENBANK Accession No. EHI39392).

In some cases, it is desirable to inhibit one or more functions of an endogenous polypeptide in order to divert metabolic intermediates toward vanillin or vanillin glucoside biosynthesis. For example, pyruvate decarboxylase (PDC1) and/or glutamate dehydrogenase activity can be reduced. In such cases, a nucleic acid that inhibits expression of the polypeptide or gene product may be included in a recombinant construct that is transformed into the strain. Alternatively, mutagenesis can be used to generate mutants in genes for which it is desired to inhibit function.

A number of prokaryotes and eukaryotes are suitable for use in constructing the recombinant microorganisms described herein, e.g., gram-negative bacteria, gram-positive bacteria, yeast or other fungi. A species and strain selected for use as a vanillin or vanillin glucoside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species may be suitable. For example, suitable species may be in a genus *Agaricus, Aspergillus, Bacillus, Candida, Corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces Yarrowia* and *Lactobacillus*. Exemplary species from such genera include *Lentinus tigrinus, Laetiporus sulphureus, Phanerochaete chrysosporium, Pichia pastoris, Physcomitrella patens, Rhodoturula glutinis* 32, *Rhodoturula mucilaginosa, Phaffia rhodozyma* UBV-AX, *Xanthophyllomyces dendrorhous, Fusarium fujikuroi/Gibberella fujikuroi, Candida utilis* and *Yarrowia lipolytica*. In some embodiments, a microorganism can be an Ascomycete such as *Gibberella fujikuroi, Kluyveromyces lactis, Schizosaccharomyces pombe, Aspergillus niger*, or *Saccharomyces cerevisiae*. In some embodiments, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of vanillin beta-D-glucoside.

Specific non-limiting examples of useful recombinant hosts are described in WO 01/40491, as well as in Hansen et al. (2009) *Appl. Environ. Microbiol.* 75:2765-2774 and Brochado, et al. (2010) *Microbial Cell Factories* 9:84, wherein the recombinant host according to this invention contains a heterologous nucleic acid encoding a mutant COMT polypeptide and/or mutant AROM polypeptide instead of the OMT genes described in WO 01/40491.

One preferred recombinant host to use with the present invention is *S. cerevisiae*, which may be recombinantly engineered as described herein. *S. cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms. The VG4 strain of *S. cerevisiae* (Brochado, et al. (2010) *Microb. Cell Fact.* 9:84) is particularly useful. VG4 has the genotype of pdc1Δgdh1Δ↑GDH2.

*Aspergillus* species such as *A. oryzae, A. niger* and *A. sojae* are widely used microorganisms in food production, and can also be used as the recombinant microorganism platform. Thus, the recombinant host may be *Aspergillus* spp. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of food ingredients such as vanillin and vanillin glucoside.

*E. coli*, another widely used platform organism in synthetic biology, can also be used as the recombinant microorganism platform. Thus, the recombinant host may be *E. coli*. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Rhodobacter* can be used as the recombinant microorganism platform. Thus, the recombinant host may be *Rhodobacter* spp. Similar to *E. coli*, there are libraries of mutants available as well as suitable plasmid vectors, allowing for rational design of various modules to enhance product yield. Methods similar to those described above for *E. coli* can be used to make recombinant *Rhodobacter* microorganisms.

*Physcomitrella* mosses, when grown in suspension culture, have characteristics similar to yeast or other fungal cultures. This genera is becoming an important type of cell for production of plant secondary metabolites, which can be difficult to produce in other types of cells. Thus, the recombinant host may be a *Physcomitrella* spp.

In some embodiments, the nucleic acids and polypeptides described herein are introduced into plants or plant cells to increase overall vanillin or vanillin glucoside production. Thus, a recombinant host can be a plant or a plant cell that includes at least one heterologous nucleic acid described herein. A plant or plant cell can be transformed by having a heterologous nucleic acid integrated into its genome, i.e., can be stably transformed. Stably transformed cells typically retain the introduced nucleic acid with each cell division. A plant or plant cell can also be transiently transformed such that the heterologous nucleic acid is not integrated into its genome. Transiently transformed cells typically lose all or some portion of the introduced nucleic acid with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a heterologous nucleic acid, for example a recombinant nucleic acid construct into other lines, to transfer a heterologous nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation; see U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art.

A population of transgenic plants can be screened and/or selected for those members of the population that have a trait or phenotype, conferred by expression of the transgene. For example, a population of progeny of a single transformation event can be screened for those plants having a desired level of expression of a polypeptide or nucleic acid described herein. Physical and biochemical methods can be used to identify expression levels. These include Southern analysis or PCR amplification for detection of a polynucleotide; northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, western blots, immunoprecipitation, and enzyme-linked immunoassays to detect polypeptides. Other techniques such as in situ hybridization, enzyme staining, and immunostaining also can be used to detect the presence or expression of polypeptides and/or nucleic acids. Methods for performing all of the referenced techniques are known.

As an alternative, a population of plants with independent transformation events can be screened for those plants having a desired trait, such as production of vanillin glucoside. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in vanillin or vanillin beta-D-glucoside level relative to a control plant that lacks the transgene.

Functional Homologs

Functional homologs of the polypeptides described above are also suitable for use in producing vanillin or vanillin glucoside in a recombinant host. Thus, the recombinant host may include one or more heterologous nucleic acid(s) encoding functional homologs of the polypeptides described above and/or a heterologous nucleic acid encoding a mutant COMT or AROM polypeptide as described herein. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional AROM and/or COMT polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of AROM or COMT polypeptides, 3DSD, ACAR, PPTase, or UGT polypeptides. Sequence analysis can involve BLAST, Reciprocal BLAST, or PSI-BLAST analysis of nonredundant databases using an AROM or COMT, 3DSD, ACAR, a PPTase, or UGT amino acid sequence as the reference sequence. Amino acid sequence is, in some instances, deduced from the nucleotide sequence. Those polypeptides in the database that have greater than 40% sequence identity are candidates for further evaluation for suitability as vanillin or vanillin glucoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in AROM or COMT polypeptides or vanillin biosynthesis polypeptides, e.g., conserved functional domains.

Conserved regions can be identified by locating a region within the primary amino acid sequence of a polypeptide that is a repeated sequence, forms some secondary structure (e.g., helices and beta sheets), establishes positively or negatively charged domains, or represents a protein motif or domain. See, e.g., the Pfam database describing consensus sequences for a variety of protein motifs and domains. The information included at the Pfam database is described in Sonnhammer, et al. (1998) *Nucl. Acids Res.* 26:320-322; Sonnhammer et al. (1997) *Proteins* 28:405-420; and Bateman et al. (1999) *Nucl. Acids Res.* 27:260-262. Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity. Sequence identity can be determined as set forth above.

The invention will be further described in the following examples, which do not limit the scope of the invention described in the claims.

Example 1: Yeast Reporter Strain for Producing Vanillin Glucoside from Glucose A genetically stable yeast strain producing vanillin glucoside from glucose was created as described in Brochado, et al. (2010) *Microb. Cell Fact.* 9:84, i.e., strain VG4 with a gene deletion of PDC1 (Pyruvate decarboxylase) and GDH1 (Glutamate dehydrogenase), and overexpressing GDH2. In addition, the strain harbored an expression construct containing a PPTase integrated into the ECM3 interlocus region of the yeast genome. Expression of the *Corynebacterium giutamicum* PPTase coding sequence was controlled by the yeast TPI1 promoter (Hansen, et al. (2009) *Appl. Environ. Microbiol.* 75(9):2765-74. Epub 2009 Mar. 13). The resulting strain was designated V12.

Example 2: Construction of an AROM Lacking Domain 5

The 5'-nearest 3912 bp of the yeast ARO1 gene, which includes all functional domains except domain 5 (having the shikimate dehydrogenase activity), was isolated by PCR amplification from genomic DNA prepared from *S. cerevisiae* strain S288C, using proof-reading PCR polymerase. The resulting DNA fragment was sub-cloned into the pTOPO vector and sequenced to confirm the DNA sequence. The nucleic acid sequence and corresponding amino acid sequence are presented in SEQ ID NO:1 and SEQ ID NO:2, respectively. This fragment was subjected to a restriction digest with SpeI and SalI and cloned into the corresponding restriction sites in the high copy number yeast expression vector p426-GPD (a 2μ-based vector), from which the inserted gene can be expressed by the strong, constitutive yeast GPD1 promoter. The resulting plasmid was designated pVAN133.

Example 3: Yeast AROM with Single Amino Acid Substitutions in Domain 5

All mutant AROM polypeptides described in this example are polypeptides of SEQ ID NO:4, wherein one amino acid has been substituted for another amino acid. The mutant AROM polypeptides are named as follows: XnnnY, where nnn indicates the position in SEQ ID NO:4 of the amino acid, which is substituted, X is the one letter code for the amino acid in position nnn in SEQ ID NO:4 and Y is the one letter code for the amino acid substituting X. By way of example A1533P refers to a mutant AROM polypeptide of SEQ ID NO:4, where the alanine at position 1533 is replaced with a proline.

The full 4764 bp yeast ARO1 gene was isolated by PCR amplification from genomic DNA prepared from *S. cerevisiae* strain S288C, using proof-reading PCR polymerase. The resulting DNA fragment was sub-cloned into the pTOPO vector and sequenced to confirm the DNA sequence. The nucleic acid sequence and corresponding amino acid sequence are presented in SEQ ID NO:3 and SEQ ID NO:4, respectively. This fragment was subjected to a restriction digest with SpeI and SalI and cloned into the corresponding restriction sites in the low copy number yeast expression vector p416-TEF (a CEN-ARS-based vector), from which the gene can be expressed from the strong TEF promoter. The resulting plasmid was designated pVAN183.

Plasmid pVAN183 was used to make 10 different domain 5 mutants of ARO1, using the QUICKCHANGE II Site-Directed Mutagenesis Kit (Agilent Technologies). With reference to SEQ ID NO:4, the mutants contained the following amino acid substitutions: A1533P, P1500K, R1458W, V1349G, T1366G, I1387H, W1571V, T1392K, K1370L and A1441P.

After sequence confirmation of these mutant AROM genes, the expression plasmids containing the A1533P, P1500K, R1458W, V1349G, T1366G, I1387H, W1571V, T1392K, K1370L and A1441P substitutions were designated pVAN368-pVAN377, respectively. The nucleic acid sequences and corresponding amino acid sequences of the AROM mutants are listed in Table 1.

TABLE 1

| Mutant | Plasmid | Nucleic Acid Sequence | Amino Acid Sequence |
|---|---|---|---|
| A1533P | pVAN368 | SEQ ID NO: 5 | SEQ ID NO: 6 |
| P1500K | pVAN369 | SEQ ID NO: 7 | SEQ ID NO: 8 |
| R1458W | pVAN370 | SEQ ID NO: 9 | SEQ ID NO: 10 |
| V1349G | pVAN371 | SEQ ID NO: 11 | SEQ ID NO: 12 |
| T1366G | pVAN372 | SEQ ID NO: 13 | SEQ ID NO: 14 |
| I1387H | pVAN373 | SEQ ID NO: 15 | SEQ ID NO: 16 |
| W1571V | pVAN374 | SEQ ID NO: 17 | SEQ ID NO: 18 |
| T1392K | pVAN375 | SEQ ID NO: 19 | SEQ ID NO: 20 |
| K1370L | pVAN376 | SEQ ID NO: 21 | SEQ ID NO: 22 |
| A1441P | pVAN377 | SEQ ID NO: 23 | SEQ ID NO: 24 |

Example 4: Yeast AROM and 3DHS Dehydratase Fusion Protein

The 5'-nearest 3951 bp of the yeast ARO1 gene, which includes all functional domains except domain 5 with the shikimate dehydrogenase activity, was isolated by PCR amplification from genomic DNA prepared from *S. cerevisiae* strain S288C, using proof-reading PCR polymerase. The resulting DNA fragment was sub-cloned into the pTOPO vector and sequenced to confirm the DNA sequence.

In order to fuse this fragment to the 3-dehydroshikimate dehydratase (3DSD) gene from the vanillin pathway, the 3DSD gene from *Podospora pauciseta* (Hansen, et al. (2009) supra) was inserted into the XmaI-EcoRI sites of yeast expression vector p426-GPD, and then the cloned ARO1 fragment was liberated and inserted into the SpeI-XmaI sites of the resulting construct. The final fusion gene is expressed from the strong, constitutive yeast GPD1 promoter. The resulting plasmid was named pVAN132. The nucleic acid sequence and corresponding amino acid sequence of this fusion protein are presented in SEQ ID NO:25 and SEQ ID NO:26, respectively.

Example 5: Expression of Mutant or Fusion AROM Enzymes in Yeast Already Biosynthesizing Vanillin Glucoside Each of the plasmids described in Examples 2, 3 and 4 were introduced into yeast strain V12 by transformation, using the lithium acetate transformation protocol, resulting in the following yeast strains: V12-Aro1-1 (containing plasmid pVAN133), V12-Aro1-2 (containing plasmid pVAN132), V12-1-3 (containing plasmid pVAN183), V12-Aro1-4 (containing plasmid pVAN368), V12-Aro1-5 (containing plasmid pVAN369), V12-Aro1-6 (containing plasmid pVAN370), V12-Aro1-7 (containing plasmid pVAN371), V12-Aro1-8 (containing plasmid pVAN372), V12-Aro1-9 (containing plasmid pVAN373), V12-Aro1-10 (containing plasmid pVAN374), V12-Aro1-11 (containing plasmid pVAN375), V12-Aro1-12 (containing plasmid pVAN376) and V12-Aro1-13 (containing plasmid pVAN377).

Yeast strains V12-Aro1-1, V12-Aro1-2, V12-1-3, V12-Aro1-4, V12-Aro1-5, V12-Aro1-6, V12-Aro1-7, V12-Aro1-8, V12-Aro1-9, V12-Aro1-10, V12-Aro1-11, V12-Aro1-12, and V12-Aro1-13 were grown as 200 ml cultures in 500 ml Erlenmeyer shake flasks using SC (synthetic complete) growth medium without aromatic amino acids, at 30° C. with moderate revolution (150 rpm) for 72 hours. Samples were taken at 48 hours, and the content of vanillin glucoside was determined. Yeast strain V12 containing the empty vectors p416-TEF or p426-GPD were included as controls. Vanillin glucoside (VG) production in the control strains (containing empty plasmids p416- and p426-GPD) was typically around 250 mg/L. Expressing the domain 5 truncated AROM is expected to increase VG production (strain V12-Aro1-1) and further physical fusion of this truncated AROM to the first committed enzyme in the heterologous vanillin pathway (*Podospora pauciseta* 3DSD) is expected to result in a further increase in vanillin glucoside production (strain V12-Aro1-2).

Of the mutant versions of AROM, in which single amino acids of domain 5 were changed, the T1392K (strain V12-Aro1-9) and K1370L (strain V12-Aro1-10) may be of use for increasing VG production. For example, an approximately 30-35% increase in VG production may be observed for T1392K (strain V12-Aro1-9) and K1370L (strain V12-Aro1-10).

This example demonstrates that by over-expressing a mutant AROM polypeptide with decreased shikimate dehydrogenase activity, the cellular concentration of 3-DHS can be increased sufficiently to play a role in the final titer yielded in the heterologous pathway. This example also demonstrates that fusing the first enzyme of the heterologous pathway, i.e., 3DHD, to a truncated AROM enzyme results in an augmentation of flux into the heterologous pathway, obtaining substrate channeling. Finally, the experiments described herein indicated that by changing discrete amino acids in the AROM domain naturally metabolizing 3DHS, the compound needed for vanillin production, the amount of the 3DHS available for vanillin biosynthesis can be increased.

Example 6: COMT Mutants

All mutant COMT polypeptides described in this example are polypeptides of SEQ ID NO:27, wherein one amino acid has been substituted for another amino acid. The mutant COMT polypeptides are named as follows: XnnnY, where nnn indicates the position in SEQ ID NO:27 of the amino acid, which is substituted, X is the one letter code for the amino acid in position nnn in SEQ ID NO:27 and Y is the one letter code for the amino acid substituting X. By way of example L198Y refers to a mutant COMT polypeptide of SEQ ID NO:27, where the leucine at position 198 is replaced with a tryptophan.

Nucleic acids encoding mutant COMT polypeptides were constructed by PCR using primers containing the desired codons. PCRs were either done as a single PCR or using sequence overlap extension PCR (SOE) by standard procedures. This step may, for example, be done by commercial providers, such as Life Technologies. The primers used are listed in Table 2.

TABLE 2

| Primer | Sequence | SEQ ID NO: |
|---|---|---|
| HSOMT_F | CGTAGCATGCAGTCTAGAAAAATGGGTGACACTAAGGAGC | 28 |
| HSOMT_R | GACGACGTTAGTGACAgaattcTTATGGACCAGCTTCAGAACCTG | 29 |
| HSOMT2_F | CGTAGCATGCAGTCTAGAaaaATGG | 30 |
| HSOMT2_R | GACGACGTTAGTGACAgaattc | 31 |
| W38NRK_F | CTATTGACACTTATTGTGAGCAAAAGGAGnrKGCTATGAACGTTG | 32 |
| W38NYK_F | CTATTGACACTTATTGTGAGCAAAAGGAGnyKGCTATGAACGTTG | 33 |
| W38_R | CTCCTTTTGCTCACAATAAGTGTCAATAG | 34 |

TABLE 2-continued

| Primer | Sequence | SEQ ID NO: |
|---|---|---|
| M40NRK_F | GACACTTATTGTGAGCAAAAGGAGTGGGCTnrKAACGTTGGTGAC | 35 |
| M4PNRK_R | CACTTATTGTGAGCAAAAGGAGTGGGCTnyKAACGTTGGTGAC | 36 |
| M40_R | CTCCTTTTGCTCACAATAAGTGTC | 37 |
| W143NRK_F | CTTTGGACATGGTTTTCTTGGACCATnrKAAGGACAGATATTTGCC | 38 |
| W143NYK_F | CTTTGGACATGGTTTTCTTGGACCATnyKAAGGACAGATATTTGCC | 39 |
| W143_R | ATGGTCCAAGAAAACCATGTCCAAAG | 40 |
| C173NRK_F | GTACTGTTTTGTTAGCTGACAACGTTATTnrKccaGGTGCTCCAGACTTCTTG | 41 |
| C173NYK_F | GTACTGTTTTGTTAGCTGACAACGTTATTnyKccaGGTGCTCCAGACTTCTTG | 42 |
| C173_R | AATAACGTTGTCAGCTAACAAAACAGTAC | 43 |
| P174NRK_F | CTGTTTTGTTAGCTGACAACGTTATTtgtnrKGGTGCTCCAGACTTC | 44 |
| P174NYK_F | CTGTTTTGTTAGCTGACAACGTTATTtgtnyKGGTGCTCCAGACTTC | 45 |
| P174_R | ACAAATAACGTTGTCAGCTAACAAAACAG | 46 |
| L198NRK_R | atttagaattcTTATGGACCAGCTTCAGAACCTGGACCCTTATATATAGCCTTCTCCAAACCGTCAACAACCTCTCTATATTCMYNGAAAGATTGATAATGAG | 47 |
| L198NYK_R | atttagaattcTATGGACCAGCTTCAGAACCTGGACCCTTATATATAGCCTTCTCCAAACCGTCAACAACCTCTCTATATTCMRNGAAAGATTGATAATGAG | 48 |
| E199NRK_R | atttagaattcTTATGGACCAGCTTCAGAACCTGGACCCTTATATATAGCCTTCTCCAAACCGTCAACAACCTCTCTATAMYNCAAGAAAGATTGATAATG | 49 |
| E199NYK_R | atttagaattcTTATGGACCAGCTTCAGAACCTGGACCCTTATATATAGCCTTCTCCAAACCGTCAACAACCTCTCTATAMRNCAAGAAAGATTGATAATG | 50 |
| R201NRK_R | atttagaattcTTATGGACCAGCTTCAGAACCTGGACCCTTATATATAGCCTTCTCCAAACCGTCAACAACCTCMYNATATTCCAAGAAAGATTG | 51 |
| R201NYK_R | atttagaattcTTATGGACCAGCTTCAGAACCTGGACCCTTATATATAGCCTTCTCCAAACCGTCAACAACCTCMRNATATTCCAAGAAAGATTG | 52 |

In the primer sequences provided above: M may be A or C; R may be A or G; W may be A or T; S may be G or C; Y may be C or T; K may be G or T; V may be A, G or C; H may be A, C or T; D may be A, G or T; B may be G, C or T; and N may be A, G, C or T.

Restriction sites for EcoRI/XbaI were included in the primers to facilitate cloning of the PCR products into the centromeric yeast expression vector p416-TEF (Mumberg, et al. (1995) *Gene* 156(1):119-22). The resulting plasmids were transformed into a Yeast strain EFSC2055 (Genotype: Mata his3D1 leu2D0 met15D0 ura3D0 adh6::LEU2 bgl1::KanMX4 PTPI1::3 DSD[AurC]::(HsOMT::MET15 [NatMX])::ACAR[HphMX]::UGT7 2E2[HIS3] ECM3::(C or PPTase-ScHAP4). This yeast strain is based on the VG4 strain (Brochado, et al. (2010) *Microbial. Cell Factories* 9:84), and further includes a disruption of HsOMT with MET15 marker, and has two additional genes integrated, namely *Corynebacterium glutamicum* PPtase (NCBI database accession no. NP 601186) and *S. cerevisiae* HAP4 (NCBI database accession no. Z28109).

The HsOMT was disrupted by PCR amplifying *S. cerevisiae* MET15 (methionine auxotrophic selection marker) using primers with 70 bp tails homologous to the front and back end of HsOMT, respectively. The yeast strain was then transformed with the PCR product, resulting in transformants having no HsOMT activity and able to grow on plates not supplemented with methionine. The resulting strain was designated EFSC2055, Plasmids expressing C or PPtase and ScHAP4 were transformed into EFSC2055 predecessor strain using the standard yeast transformation lithium acetate/PEG protocol and transformants were selected on SC-uracil plates. Transformants were tested by growing in 3 ml cultures for 72 hours in Delft medium supplemented with 8% sugar beet molasses.

Cultures were analyzed using HPLC-UV to quantify vanillin glucoside/Isovanillin glucoside and related products. HPLC analysis was carried out with an AGILENT 1100 series system with binary pump and a Phenomenex Synergi Polar-RP 2.5u 100 Å 100×2.00 mm column, which separates precursors and Isovanillin and vanillin. A flat gradient was run with water/acetonitrile+0.1% trifluoroacetic acid. A 8.9 minute program+1.1 minute postrun was carried out as presented in Table 3.

TABLE 3

| Time | % Acetonitrile | Flow ml/min. |
|---|---|---|
| 0 | 5 | 0.5 |
| 0.7 | 5 | 0.5 |
| 5.7 | 27 | 0.5 |
| 6.2 | 100 | 0.5 |
| 6.6 | 100 | 0.7 |
| 7.8 | 100 | 1.0 |
| 8.1 | 100 | 1.0 |
| 8.6 | 5 | 0.8 |
| 8.9 | 5 | 0.6 |

Vanillin glucoside and isovanillin glucoside were quantified by integrating the area of the HPLC peaks and comparing the same with a standard curve. The results of this analysis are shown in FIG. 3A. Yeast cells expressing the wild-type Hs-OMT of SEQ ID NO:27 (referred to as Hs-COMT wt) produced isovanillin and vanillin in a ratio of approximately 1:3, whereas the mutant L198Y produced isovanillin and vanillin in a ratio of approximately 1:125. The exact ratio was difficult to determine as isovanillin production was at the detection limit.

In addition to the mutations analyzed in FIG. 3A, good specificity and low isovanillin production in the mutants L198C, L198N, L198D, L198F, and L198E.

Example 7: Reduction of Vanillyl Alcohol

Figure 4:
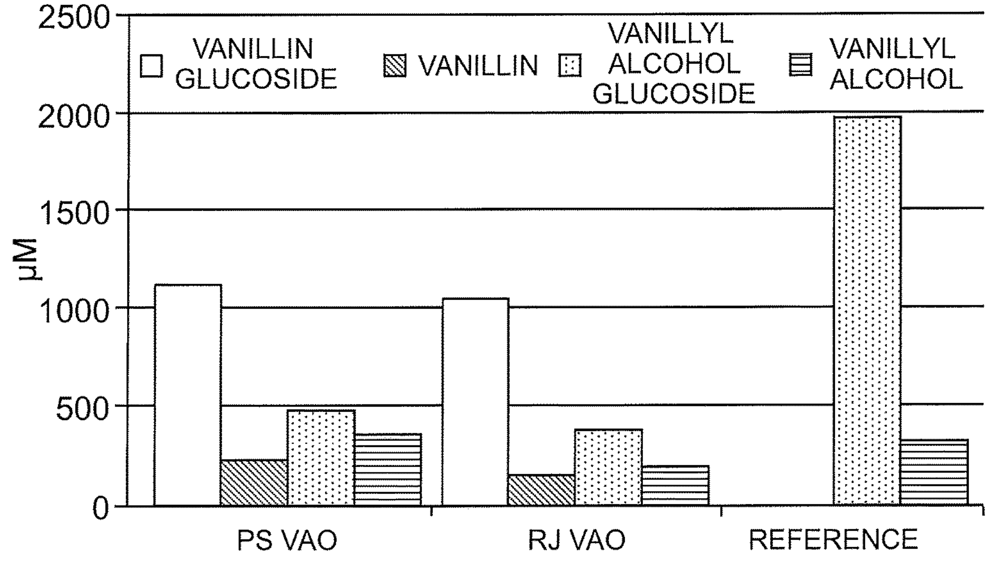
FIG. 4 shows the levels of vanillin glucoside, vanillin, vanillyl alcohol glucoside and vanillyl alcohol in yeast strains expressing *Penicillium simplicissium* (PS) or *Rhodococcus jostii* (RJ) vanillyl alcohol oxidase (VAO), which were supplemented with 3 mM vanillyl alcohol.

By way of illustration, *P. simplicissium* (GENBANK Accession No. P56216) and *R. jostii* (GENBANK Accession No. YP_703243.1) VAO genes were isolated and cloned into a yeast expression vector. The expression vectors were subsequently transformed into a yeast strain expressing glucosyltransferase. The transformed strains were tested for VAO activity by growing the yeast for 48 hours in medium supplemented with 3 mM vanillyl alcohol. The results of this analysis are presented in FIG. 4. VAO enzymes from both *P. simplicissium* and *R. jostii* exhibited activity in yeast. When the VAO enzymes were analyzed in a strain capable of producing vanillin glucoside, there was a reduction in the accumulation of vanillyl alcohol during vanillin glucoside fermentation.

Example 8: ACAR Gene from *Neurospora crassa*

Figure 5:
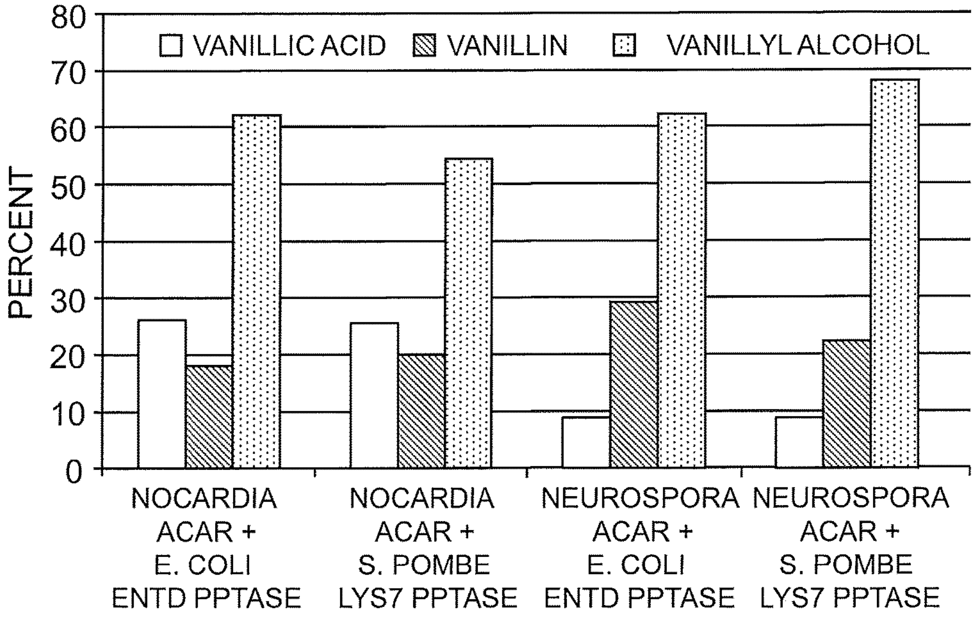
FIG. 5 shows the levels of vanillic acid, vanillin, and vanillin glucoside in yeast strains expressing *N. iowensis* ACAR or *N. crassa* ACAR and of *E. coli* phosphopantetheinyl transferase (PPTase) or *S. pombe* PPTase, when grown in medium supplemented with 3 mM vanillic acid.

As an alternative to an ACAR protein (EC 1.2.1.30) from *Nocardia iowensis* (Hansen, et al. ((2009) *Appl. Environ. Microbiol.* 75:2765-74), the use of a *Neurospora crassa* ACAR enzyme (Gross & Zenk (1969) *Eur. J. Biochem.* 8:413-9; U.S. Pat. No. 6,372,461) in yeast was investigated, as *Neurospora* (bread mold) is a GRAS organism. An *N. crassa* gene (GENBANK XP_955820) with homology to the *Nocardia iowensis* ACAR was isolated and cloned into a yeast expression vector. The vector was transformed into a yeast strain expressing a PPtase, strains were selected for the presence of the ACAR gene, and the selected yeast was cultured for 72 hours in medium supplemented with 3 mM vanillic acid to demonstrate ACAR activity. The results of this analysis are presented in FIG. 5. The *N. crassa* ACAR enzyme was found to exhibit a higher activity in yeast than the *N. iowensis* ACAR. Therefore, in some embodiments of the method disclosed herein, a *N. crassa* ACAR enzyme is used in the production of vanillin or vanillin glucoside.

In addition to *N. iownsis* or *N. crassa* ACAR proteins, it is contemplated that other ACAR proteins may be used, including but not limited to, those isolated from *Nocardia brasiliensis* (GENBANK Accession No. EHY26728), *Nocardia farcinica* (GENBANK Accession No. BAD56861), *Podospora anserina* (GENBANK Accession No. CAP62295), or *Sordaria macropora* (GENBANK Accession No. CCC14931), which significant sequence identity with the *N. iownsis* or *N. crassa* ACAR protein.

What is claimed is:

1. A recombinant mutant Arom Multifunctional Enzyme (AROM) polypeptide having the amino acid sequence of SEQ ID NO:20 or SEQ ID NO:22.

2. The recombinant mutant AROM polypeptide of claim 1, wherein said recombinant mutant AROM polypeptide further comprises a purification tag, a chloroplast transit peptide, a mitochondrial transit peptide, an amyloplast peptide, signal peptide, or a secretion tag at the N- or C-terminus of said polypeptide.

* * * * *

SEQUENCE LISTING

```
<160> NUMBER OF SEQ ID NOS: 56

<210> SEQ ID NO 1
<211> LENGTH: 3912
<212> TYPE: DNA
<213> ORGANISM: Saccharomyces cerevisiae

<400> SEQUENCE: 1

atggtgcagt tagccaaagt cccaattcta ggaaatgata ttatccacgt tgggtataac      60

attcatgacc atttggttga aaccataatt aaacattgtc cttcttcgac atacgttatt     120

tgcaatgata cgaacttgag taaagttcca tactaccagc aattagtcct ggaattcaag     180

gcttctttgc cagaaggctc tcgtttactt acttatgttg ttaaaccagg tgagacaagt     240

aaaagtagag aaaccaaagc gcagctagaa gattatcttt tagtggaagg atgtactcgt     300

gatacggtta tggtagcgat cggtggtggt gttattggtg acatgattgg gttcgttgca     360

tctacattta tgagaggtgt tcgtgttgtc caagtaccaa catccttatt ggcaatggtc     420

gattcctcca ttggtggtaa aactgctatt gacactcctc taggtaaaaa ctttattggt     480
```

-continued

```
gcattttggc aaccaaaatt tgtccttgta gatattaaat ggctagaaac gttagccaag    540
agagagttta tcaatgggat ggcagaagtt atcaagactg cttgtatttg gaacgctgac    600
gaatttacta gattagaatc aaacgcttcg ttgttcttaa atgttgttaa tggggcaaaa    660
aatgtcaagg ttaccaatca attgacaaac gagattgacg agatatcgaa tacagatatt    720
gaagctatgt tggatcatac atataagtta gttcttgaga gtattaaggt caaagcggaa    780
gttgtctctt cggatgaacg tgaatccagt ctaagaaacc ttttgaactt cggacattct    840
attggtcatg cttatgaagc tatactaacc ccacaagcat tacatggtga atgtgtgtcc    900
attggtatgg ttaaagaggc ggaattatcc cgttatttcg gtattctctc ccctacccaa    960
gttgcacgtc tatccaagat tttggttgcc tacgggttgc ctgtttcgcc tgatgagaaa   1020
tggtttaaag agctaacctt acataagaaa acaccattgg atatcttatt gaagaaaatg   1080
agtattgaca agaaaaacga gggttccaaa aagaaggtgg tcattttaga aagtattggt   1140
aagtgctatg gtgactccgc tcaatttgtt agcgatgaag acctgagatt tattctaaca   1200
gatgaaaccc tcgtttaccc cttcaaggac atccctgctg atcaacagaa agttgttatc   1260
ccccctggtt ctaagtccat ctccaatcgt gctttaattc ttgctgccct cggtgaaggt   1320
caatgtaaaa tcaagaactt attacattct gatgatacta aacatatgtt aaccgctgtt   1380
catgaattga aaggtgctac gatatcatgg gaagataatg gtgagacggt agtggtggaa   1440
ggacatggtg gttccacatt gtcagcttgt gctgacccct tatatctagg taatgcaggt   1500
actgcatcta gatttttgac ttccttggct gccttggtca attctacttc aagccaaaag   1560
tatatcgttt taactggtaa cgcaagaatg caacaaagac caattgctcc tttggtcgat   1620
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
gagctgtttg agcaacagca taacaatcaa agtgttaaac aatttgttgt ggagaacggt   2820
```

-continued

```
tgggagaagt tccgtgagga agaaacaaga attttcaagg aagttattca aaattacggc   2880

gatgatggat atgttttctc aacaggtggc ggtattgttg aaagcgctga gtctagaaaa   2940

gccttaaaag attttgcctc atcaggtgga tacgttttac acttacatag ggatattgag   3000

gagacaattg tctttttaca aagtgatcct tcaagacctg cctatgtgga agaaattcgt   3060

gaagtttgga acagaaggga ggggtggtat aaagaatgct caaatttctc tttctttgct   3120

cctcattgct ccgcagaagc tgagttccaa gctctaagaa gatcgtttag taagtacatt   3180

gcaaccatta caggtgtcag agaaatagaa attccaagcg gaagatctgc ctttgtgtgt   3240

ttaacctttg atgacttaac tgaacaaact gagaatttga ctccaatctg ttatggttgt   3300

gaggctgtag aggtcagagt agaccatttg gctaattact ctgctgattt cgtgagtaaa   3360

cagttatcta tattgcgtaa agccactgac agtattccta tcatttttac tgtgcgaacc   3420

atgaagcaag gtggcaactt tcctgatgaa gagttcaaaa ccttgagaga gctatacgat   3480

attgccttga agaatggtgt tgaattcctt gacttagaac taactttacc tactgatatc   3540

caatatgagg ttattaacaa aaggggcaac accaagatca ttggttccca tcatgacttc   3600

caaggattat actcctggga cgacgctgaa tgggaaaaca gattcaatca agcgttaact   3660

cttgatgtgg atgttgtaaa atttgtgggt acggctgtta atttcgaaga taatttgaga   3720

ctggaacact ttagggatac acacaagaat aagcctttaa ttgcagttaa tatgacttct   3780

aaaggtagca tttctcgtgt tttgaataat gttttaacac ctgtgacatc agatttattg   3840

cctaactccg ctgcccctgg ccaattgaca gtagcacaaa ttaacaagat gtatacatct   3900

atgggaggtt ga                                                       3912
```

<210> SEQ ID NO 2
<211> LENGTH: 1303
<212> TYPE: PRT
<213> ORGANISM: Saccharomyces cerevisiae

<400> SEQUENCE: 2

```
Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175
```

-continued

```
Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
```

-continued

```
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                1005

Asp Pro  Ser Arg Pro Ala Tyr  Val Glu Glu Ile Arg  Glu Val Trp
    1010                 1015                 1020
```

```
Asn Arg  Arg Glu Gly Trp Tyr  Lys Glu Cys Ser Asn  Phe Ser Phe
    1025                 1030                 1035

Phe Ala  Pro His Cys Ser Ala  Glu Ala Glu Phe Gln  Ala Leu Arg
    1040                 1045                 1050

Arg Ser  Phe Ser Lys Tyr Ile  Ala Thr Ile Thr Gly  Val Arg Glu
    1055                 1060                 1065

Ile Glu  Ile Pro Ser Gly Arg  Ser Ala Phe Val Cys  Leu Thr Phe
    1070                 1075                 1080

Asp Asp  Leu Thr Glu Gln Thr  Glu Asn Leu Thr Pro  Ile Cys Tyr
    1085                 1090                 1095

Gly Cys  Glu Ala Val Glu Val  Arg Val Asp His Leu  Ala Asn Tyr
    1100                 1105                 1110

Ser Ala  Asp Phe Val Ser Lys  Gln Leu Ser Ile Leu  Arg Lys Ala
    1115                 1120                 1125

Thr Asp  Ser Ile Pro Ile Ile  Phe Thr Val Arg Thr  Met Lys Gln
    1130                 1135                 1140

Gly Gly  Asn Phe Pro Asp Glu  Glu Phe Lys Thr Leu  Arg Glu Leu
    1145                 1150                 1155

Tyr Asp  Ile Ala Leu Lys Asn  Gly Val Glu Phe Leu  Asp Leu Glu
    1160                 1165                 1170

Leu Thr  Leu Pro Thr Asp Ile  Gln Tyr Glu Val Ile  Asn Lys Arg
    1175                 1180                 1185

Gly Asn  Thr Lys Ile Ile Gly  Ser His His Asp Phe  Gln Gly Leu
    1190                 1195                 1200

Tyr Ser  Trp Asp Asp Ala Glu  Trp Glu Asn Arg Phe  Asn Gln Ala
    1205                 1210                 1215

Leu Thr  Leu Asp Val Asp Val  Val Lys Phe Val Gly  Thr Ala Val
    1220                 1225                 1230

Asn Phe  Glu Asp Asn Leu Arg  Leu Glu His Phe Arg  Asp Thr His
    1235                 1240                 1245

Lys Asn  Lys Pro Leu Ile Ala  Val Asn Met Thr Ser  Lys Gly Ser
    1250                 1255                 1260

Ile Ser  Arg Val Leu Asn Asn  Val Leu Thr Pro Val  Thr Ser Asp
    1265                 1270                 1275

Leu Leu  Pro Asn Ser Ala Ala  Pro Gly Gln Leu Thr  Val Ala Gln
    1280                 1285                 1290

Ile Asn  Lys Met Tyr Thr Ser  Met Gly Gly
    1295                 1300
```

<210> SEQ ID NO 3
<211> LENGTH: 4767
<212> TYPE: DNA
<213> ORGANISM: Saccharomyces cerevisiae

<400> SEQUENCE: 3

```
atggtgcagt tagccaaagt cccaattcta ggaaatgata ttatccacgt tgggtataac      60

attcatgacc atttggttga aaccataatt aaacattgtc cttcttcgac atacgttatt     120

tgcaatgata cgaacttgag taaagttcca tactaccagc aattagtcct ggaattcaag     180

gcttctttgc cagaaggctc tcgtttactt acttatgttg ttaaaccagg tgagacaagt     240

aaaagtagag aaaccaaagc gcagctagaa gattatcttt tagtggaagg atgtactcgt     300

gatacggtta tggtagcgat cggtggtggt gttattggtg acatgattgg gttcgttgca     360

tctacattta tgagaggtgt tcgtgttgtc caagtaccaa catccttatt ggcaatggtc     420
```

-continued

```
gattcctcca ttggtggtaa aactgctatt gacactcctc taggtaaaaa ctttattggt    480
gcattttggc aaccaaaatt tgtccttgta gatattaaat ggctagaaac gttagccaag    540
agagagttta tcaatgggat ggcagaagtt atcaagactg cttgtatttg gaacgctgac    600
gaatttacta gattagaatc aaacgcttcg ttgttcttaa atgttgttaa tggggcaaaa    660
aatgtcaagg ttaccaatca attgacaaac gagattgacg agatatcgaa tacagatatt    720
gaagctatgt tggatcatac atataagtta gttcttgaga gtattaaggt caaagcggaa    780
gttgtctctt cggatgaacg tgaatccagt ctaagaaacc ttttgaactt cggacattct    840
attggtcatg cttatgaagc tatactaacc ccacaagcat tacatggtga atgtgtgtcc    900
attggtatgg ttaaagaggc ggaattatcc cgttatttcg gtattctctc ccctacccaa    960
gttgcacgtc tatccaagat tttggttgcc tacgggttgc ctgtttcgcc tgatgagaaa   1020
tggtttaaag agctaacctt acataagaaa acaccattgg atatcttatt gaagaaaatg   1080
agtattgaca agaaaaacga gggttccaaa aagaaggtgg tcattttaga aagtattggt   1140
aagtgctatg gtgactccgc tcaatttgtt agcgatgaag acctgagatt tattctaaca   1200
gatgaaaccc tcgtttaccc cttcaaggac atccctgctg atcaacagaa agttgttatc   1260
ccccctggtt ctaagtccat ctccaatcgt gctttaattc ttgctgccct cggtgaaggt   1320
caatgtaaaa tcaagaactt attacattct gatgatacta aacatatgtt aaccgctgtt   1380
catgaattga aaggtgctac gatatcatgg gaagataatg gtgagacggt agtggtggaa   1440
ggacatggtg gttccacatt gtcagcttgt gctgacccct tatatctagg taatgcaggt   1500
actgcatcta gatttttgac ttccttggct gccttggtca attctacttc aagccaaaag   1560
tatatcgttt taactggtaa cgcaagaatg caacaaagac caattgctcc tttggtcgat   1620
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
```

-continued

```
gagctgtttg agcaacagca taacaatcaa agtgttaaac aatttgttgt ggagaacggt   2820
tgggagaagt tccgtgagga agaaacaaga attttcaagg aagttattca aaattacggc   2880
gatgatggat atgttttctc aacaggtggc ggtattgttg aaagcgctga gtctagaaaa   2940
gccttaaaag attttgcctc atcaggtgga tacgttttac acttacatag ggatattgag   3000
gagacaattg tctttttaca aagtgatcct tcaagacctg cctatgtgga agaaattcgt   3060
gaagtttgga acagaaggga ggggtggtat aaagaatgct caaatttctc tttctttgct   3120
cctcattgct ccgcagaagc tgagttccaa gctctaagaa gatcgtttag taagtacatt   3180
gcaaccatta caggtgtcag agaaatagaa attccaagcg gaagatctgc ctttgtgtgt   3240
ttaacctttg atgacttaac tgaacaaact gagaatttga ctccaatctg ttatggttgt   3300
gaggctgtag aggtcagagt agaccatttg gctaattact ctgctgattt cgtgagtaaa   3360
cagttatcta tattgcgtaa agccactgac agtattccta tcatttttac tgtgcgaacc   3420
atgaagcaag gtggcaactt tcctgatgaa gagttcaaaa ccttgagaga gctatacgat   3480
attgccttga agaatggtgt tgaattcctt gacttagaac taactttacc tactgatatc   3540
caatatgagg ttattaacaa aaggggcaac accaagatca ttggttccca tcatgacttc   3600
caaggattat actcctggga cgacgctgaa tgggaaaaca gattcaatca agcgttaact   3660
cttgatgtgg atgttgtaaa atttgtgggt acggctgtta atttcgaaga taatttgaga   3720
ctggaacact ttagggatac acacaagaat aagcctttaa ttgcagttaa tatgacttct   3780
aaaggtagca tttctcgtgt tttgaataat gttttaacac ctgtgacatc agatttattg   3840
cctaactccg ctgcccctgg ccaattgaca gtagcacaaa ttaacaagat gtatacatct   3900
atgggaggta tcgagcctaa ggaactgttt gttgttggaa agccaattgg ccactctaga   3960
tcgccaattt tacataacac tggctatgaa attttaggtt tacctcacaa gttcgataaa   4020
tttgaaactg aatccgcaca attggtgaaa gaaaaacttt tggacggaaa caagaacttt   4080
ggcggtgctg cagtcacaat tcctctgaaa ttagatataa tgcagtacat ggatgaattg   4140
actgatgctg ctaaagttat tggtgctgta aacacagtta taccattggg taacaagaag   4200
tttaagggtg ataataccga ctggttaggt atccgtaatg ccttaattaa caatggcgtt   4260
cccgaatatg ttggtcatac cgctggtttg gttatcggtg caggtggcac ttctagagcc   4320
gccctttacg ccttgcacag tttaggttgc aaaaagatct tcataatcaa caggacaact   4380
tcgaaattga agccattaat agagtcactt ccatctgaat tcaacattat tggaatagag   4440
tccactaaat ctatagaaga gattaaggaa cacgttggcg ttgctgtcag ctgtgtacca   4500
gccgacaaac cattagatga cgaactttta agtaagctgg agagattcct tgtgaaaggt   4560
gcccatgctg cttttgtacc aaccttattg gaagccgcat acaaaccaag cgttactccc   4620
gttatgacaa tttcacaaga caaatatcaa tggcacgttg tccctggatc acaaatgtta   4680
gtacaccaag gtgtagctca gtttgaaaag tggacaggat tcaagggccc tttcaaggcc   4740
atttttgatg ccgttacgaa agagtag                                        4767
```

<210> SEQ ID NO 4
<211> LENGTH: 1588
<212> TYPE: PRT
<213> ORGANISM: Saccharomyces cerevisiae

<400> SEQUENCE: 4

```
Met Val Gln Leu Ala Lys Val Pro Ile Leu Gly Asn Asp Ile Ile His
1               5                   10                  15
```

-continued

```
Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
```

-continued

```
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860
```

```
Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                 1005

Asp Pro  Ser Arg Pro Ala Tyr  Val Glu Glu Ile Arg  Glu Val Trp
    1010                 1015                 1020

Asn Arg  Arg Glu Gly Trp Tyr  Lys Glu Cys Ser Asn  Phe Ser Phe
    1025                 1030                 1035

Phe Ala  Pro His Cys Ser Ala  Glu Ala Glu Phe Gln  Ala Leu Arg
    1040                 1045                 1050

Arg Ser  Phe Ser Lys Tyr Ile  Ala Thr Ile Thr Gly  Val Arg Glu
    1055                 1060                 1065

Ile Glu  Ile Pro Ser Gly Arg  Ser Ala Phe Val Cys  Leu Thr Phe
    1070                 1075                 1080

Asp Asp  Leu Thr Glu Gln Thr  Glu Asn Leu Thr Pro  Ile Cys Tyr
    1085                 1090                 1095

Gly Cys  Glu Ala Val Glu Val  Arg Val Asp His Leu  Ala Asn Tyr
    1100                 1105                 1110

Ser Ala  Asp Phe Val Ser Lys  Gln Leu Ser Ile Leu  Arg Lys Ala
    1115                 1120                 1125

Thr Asp  Ser Ile Pro Ile Ile  Phe Thr Val Arg Thr  Met Lys Gln
    1130                 1135                 1140

Gly Gly  Asn Phe Pro Asp Glu  Glu Phe Lys Thr Leu  Arg Glu Leu
    1145                 1150                 1155

Tyr Asp  Ile Ala Leu Lys Asn  Gly Val Glu Phe Leu  Asp Leu Glu
    1160                 1165                 1170

Leu Thr  Leu Pro Thr Asp Ile  Gln Tyr Glu Val Ile  Asn Lys Arg
    1175                 1180                 1185

Gly Asn  Thr Lys Ile Ile Gly  Ser His His Asp Phe  Gln Gly Leu
    1190                 1195                 1200

Tyr Ser  Trp Asp Asp Ala Glu  Trp Glu Asn Arg Phe  Asn Gln Ala
    1205                 1210                 1215

Leu Thr  Leu Asp Val Asp Val  Val Lys Phe Val Gly  Thr Ala Val
    1220                 1225                 1230

Asn Phe  Glu Asp Asn Leu Arg  Leu Glu His Phe Arg  Asp Thr His
    1235                 1240                 1245

Lys Asn  Lys Pro Leu Ile Ala  Val Asn Met Thr Ser  Lys Gly Ser
    1250                 1255                 1260
```

```
Ile Ser  Arg Val Leu Asn Asn  Val Leu Thr Pro Val  Thr Ser Asp
    1265                 1270                 1275

Leu Leu  Pro Asn Ser Ala Ala  Pro Gly Gln Leu Thr  Val Ala Gln
    1280                 1285                 1290

Ile Asn  Lys Met Tyr Thr Ser  Met Gly Gly Ile Glu  Pro Lys Glu
    1295                 1300                 1305

Leu Phe  Val Val Gly Lys Pro  Ile Gly His Ser Arg  Ser Pro Ile
    1310                 1315                 1320

Leu His  Asn Thr Gly Tyr Glu  Ile Leu Gly Leu Pro  His Lys Phe
    1325                 1330                 1335

Asp Lys  Phe Glu Thr Glu Ser  Ala Gln Leu Val Lys  Glu Lys Leu
    1340                 1345                 1350

Leu Asp  Gly Asn Lys Asn Phe  Gly Gly Ala Ala Val  Thr Ile Pro
    1355                 1360                 1365

Leu Lys  Leu Asp Ile Met Gln  Tyr Met Asp Glu Leu  Thr Asp Ala
    1370                 1375                 1380

Ala Lys  Val Ile Gly Ala Val  Asn Thr Val Ile Pro  Leu Gly Asn
    1385                 1390                 1395

Lys Lys  Phe Lys Gly Asp Asn  Thr Asp Trp Leu Gly  Ile Arg Asn
    1400                 1405                 1410

Ala Leu  Ile Asn Asn Gly Val  Pro Glu Tyr Val Gly  His Thr Ala
    1415                 1420                 1425

Gly Leu  Val Ile Gly Ala Gly  Gly Thr Ser Arg Ala  Ala Leu Tyr
    1430                 1435                 1440

Ala Leu  His Ser Leu Gly Cys  Lys Lys Ile Phe Ile  Ile Asn Arg
    1445                 1450                 1455

Thr Thr  Ser Lys Leu Lys Pro  Leu Ile Glu Ser Leu  Pro Ser Glu
    1460                 1465                 1470

Phe Asn  Ile Ile Gly Ile Glu  Ser Thr Lys Ser Ile  Glu Glu Ile
    1475                 1480                 1485

Lys Glu  His Val Gly Val Ala  Val Ser Cys Val Pro  Ala Asp Lys
    1490                 1495                 1500

Pro Leu  Asp Asp Glu Leu Leu  Ser Lys Leu Glu Arg  Phe Leu Val
    1505                 1510                 1515

Lys Gly  Ala His Ala Ala Phe  Val Pro Thr Leu Leu  Glu Ala Ala
    1520                 1525                 1530

Tyr Lys  Pro Ser Val Thr Pro  Val Met Thr Ile Ser  Gln Asp Lys
    1535                 1540                 1545

Tyr Gln  Trp His Val Val Pro  Gly Ser Gln Met Leu  Val His Gln
    1550                 1555                 1560

Gly Val  Ala Gln Phe Glu Lys  Trp Thr Gly Phe Lys  Gly Pro Phe
    1565                 1570                 1575

Lys Ala  Ile Phe Asp Ala Val  Thr Lys Glu
    1580                 1585
```

<210> SEQ ID NO 5
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 5

```
atggtgcagt tagccaaagt cccaattcta ggaaatgata ttatccacgt tgggtataac     60

attcatgacc atttggttga aaccataatt aaacattgtc cttcttcgac atacgttatt    120
```

```
tgcaatgata cgaacttgag taaagttcca tactaccagc aattagtcct ggaattcaag    180
gcttctttgc cagaaggctc tcgtttactt acttatgttg ttaaaccagg tgagacaagt    240
aaaagtagag aaaccaaagc gcagctagaa gattatcttt tagtggaagg atgtactcgt    300
gatacggtta tggtagcgat cggtggtggt gttattggtg acatgattgg gttcgttgca    360
tctacattta tgagaggtgt tcgtgttgtc caagtaccaa catccttatt ggcaatggtc    420
gattcctcca ttggtggtaa aactgctatt gacactcctc taggtaaaaa ctttattggt    480
gcattttggc aaccaaaatt tgtccttgta gatattaaat ggctagaaac gttagccaag    540
agagagttta tcaatgggat ggcagaagtt atcaagactg cttgtatttg gaacgctgac    600
gaatttacta gattagaatc aaacgcttcg ttgttcttaa atgttgttaa tggggcaaaa    660
aatgtcaagg ttaccaatca attgacaaac gagattgacg agatatcgaa tacagatatt    720
gaagctatgt tggatcatac atataagtta gttcttgaga gtattaaggt caaagcggaa    780
gttgtctctt cggatgaacg tgaatccagt ctaagaaacc ttttgaactt cggacattct    840
attggtcatg cttatgaagc tatactaacc ccacaagcat tacatggtga atgtgtgtcc    900
attggtatgg ttaaagaggc ggaattatcc cgttatttcg gtattctctc ccctacccaa    960
gttgcacgtc tatccaagat tttggttgcc tacgggttgc ctgtttcgcc tgatgagaaa   1020
tggtttaaag agctaacctt acataagaaa acaccattgg atatcttatt gaagaaaatg   1080
agtattgaca agaaaaacga gggttccaaa aagaaggtgg tcattttaga aagtattggt   1140
aagtgctatg gtgactccgc tcaatttgtt agcgatgaag acctgagatt tattctaaca   1200
gatgaaaccc tcgtttaccc cttcaaggac atccctgctg atcaacagaa agttgttatc   1260
ccccctggtt ctaagtccat ctccaatcgt gctttaattc ttgctgccct cggtgaaggt   1320
caatgtaaaa tcaagaactt attacattct gatgatacta aacatatgtt aaccgctgtt   1380
catgaattga aggtgctac gatatcatgg gaagataatg gtgagacggt agtggtggaa   1440
ggacatggtg gttccacatt gtcagcttgt gctgacccct tatatctagg taatgcaggt   1500
actgcatcta gatttttgac ttccttggct gccttggtca attctacttc aagccaaaag   1560
tatatcgttt taactggtaa cgcaagaatg caacaaagac caattgctcc tttggtcgat   1620
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
```

-continued

```
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
gagctgtttg agcaacagca taacaatcaa agtgttaaac aatttgttgt ggagaacggt   2820
tgggagaagt tccgtgagga agaaacaaga attttcaagg aagttattca aaattacggc   2880
gatgatggat atgttttctc aacaggtggc ggtattgttg aaagcgctga gtctagaaaa   2940
gccttaaaag attttgcctc atcaggtgga tacgttttac acttacatag ggatattgag   3000
gagacaattg tctttttaca aagtgatcct tcaagacctg cctatgtgga agaaattcgt   3060
gaagtttgga acagaaggga ggggtggtat aaagaatgct caaatttctc tttctttgct   3120
cctcattgct ccgcagaagc tgagttccaa gctctaagaa gatcgtttag taagtacatt   3180
gcaaccatta caggtgtcag agaaatagaa attccaagcg gaagatctgc ctttgtgtgt   3240
ttaacctttg atgacttaac tgaacaaact gagaatttga ctccaatctg ttatggttgt   3300
gaggctgtag aggtcagagt agaccatttg gctaattact ctgctgattt cgtgagtaaa   3360
cagttatcta tattgcgtaa agccactgac agtattccta tcatttttac tgtgcgaacc   3420
atgaagcaag gtggcaactt tcctgatgaa gagttcaaaa ccttgagaga gctatacgat   3480
attgccttga agaatggtgt tgaattcctt gacttagaac taactttacc tactgatatc   3540
caatatgagg ttattaacaa aaggggcaac accaagatca ttggttccca tcatgacttc   3600
caaggattat actcctggga cgacgctgaa tgggaaaaca gattcaatca agcgttaact   3660
cttgatgtgg atgttgtaaa atttgtgggt acggctgtta atttcgaaga taatttgaga   3720
ctggaacact ttagggatac acacaagaat aagcctttaa ttgcagttaa tatgacttct   3780
aaaggtagca tttctcgtgt tttgaataat gttttaacac ctgtgacatc agatttattg   3840
cctaactccg ctgcccctgg ccaattgaca gtagcacaaa ttaacaagat gtatacatct   3900
atgggaggta tcgagcctaa ggaactgttt gttgttggaa agccaattgg ccactctaga   3960
tcgccaattt tacataacac tggctatgaa attttaggtt tacctcacaa gttcgataaa   4020
tttgaaactg aatccgcaca attggtgaaa gaaaaacttt tggacggaaa caagaacttt   4080
ggcggtgctg cagtcacaat tcctctgaaa ttagatataa tgcagtacat ggatgaattg   4140
actgatgctg ctaaagttat tggtgctgta aacacagtta taccattggg taacaagaag   4200
tttaagggtg ataataccga ctggttaggt atccgtaatg ccttaattaa caatggcgtt   4260
cccgaatatg ttggtcatac cgctggtttg gttatcggtg caggtggcac ttctagagcc   4320
gccctttacg ccttgcacag tttaggttgc aaaaagatct tcataatcaa caggacaact   4380
tcgaaattga agccattaat agagtcactt ccatctgaat tcaacattat tggaatagag   4440
tccactaaat ctatagaaga gattaaggaa cacgttggcg ttgctgtcag ctgtgtacca   4500
gccgacaaac cattagatga cgaacttttta agtaagctgg agagattcct tgtgaaaggt   4560
gcccatgctg cttttgtacc aaccttattg gaagccccat acaaaccaag cgttactccc   4620
gttatgacaa tttcacaaga caaatatcaa tggcacgttg tccctggatc acaaatgtta   4680
gtacaccaag gtgtagctca gtttgaaaag tggacaggat tcaagggccc tttcaaggcc   4740
atttttgatg ccgttacgaa agagtag                                        4767
```

<210> SEQ ID NO 6
<211> LENGTH: 1588
<212> TYPE: PRT
<213> ORGANISM: Artificial sequence
<220> FEATURE:
<223> OTHER INFORMATION: Synthethic polypeptide

<400> SEQUENCE: 6

```
Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
```

-continued

```
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800
```

-continued

```
Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                 1005

Asp Pro  Ser Arg Pro Ala Tyr  Val Glu Glu Ile Arg  Glu Val Trp
    1010                 1015                 1020

Asn Arg  Arg Glu Gly Trp Tyr  Lys Glu Cys Ser Asn  Phe Ser Phe
    1025                 1030                 1035

Phe Ala  Pro His Cys Ser Ala  Glu Ala Glu Phe Gln  Ala Leu Arg
    1040                 1045                 1050

Arg Ser  Phe Ser Lys Tyr Ile  Ala Thr Ile Thr Gly  Val Arg Glu
    1055                 1060                 1065

Ile Glu  Ile Pro Ser Gly Arg  Ser Ala Phe Val Cys  Leu Thr Phe
    1070                 1075                 1080

Asp Asp  Leu Thr Glu Gln Thr  Glu Asn Leu Thr Pro  Ile Cys Tyr
    1085                 1090                 1095

Gly Cys  Glu Ala Val Glu Val  Arg Val Asp His Leu  Ala Asn Tyr
    1100                 1105                 1110

Ser Ala  Asp Phe Val Ser Lys  Gln Leu Ser Ile Leu  Arg Lys Ala
    1115                 1120                 1125

Thr Asp  Ser Ile Pro Ile Ile  Phe Thr Val Arg Thr  Met Lys Gln
    1130                 1135                 1140

Gly Gly  Asn Phe Pro Asp Glu  Glu Phe Lys Thr Leu  Arg Glu Leu
    1145                 1150                 1155

Tyr Asp  Ile Ala Leu Lys Asn  Gly Val Glu Phe Leu  Asp Leu Glu
    1160                 1165                 1170

Leu Thr  Leu Pro Thr Asp Ile  Gln Tyr Glu Val Ile  Asn Lys Arg
    1175                 1180                 1185

Gly Asn  Thr Lys Ile Ile Gly  Ser His His Asp Phe  Gln Gly Leu
    1190                 1195                 1200
```

-continued

```
Tyr Ser  Trp Asp Asp Ala Glu  Trp Glu Asn Arg Phe  Asn Gln Ala
    1205                 1210                 1215

Leu Thr  Leu Asp Val Asp Val  Val Lys Phe Val Gly  Thr Ala Val
    1220                 1225                 1230

Asn Phe  Glu Asp Asn Leu Arg  Leu Glu His Phe Arg  Asp Thr His
    1235                 1240                 1245

Lys Asn  Lys Pro Leu Ile Ala  Val Asn Met Thr Ser  Lys Gly Ser
    1250                 1255                 1260

Ile Ser  Arg Val Leu Asn Asn  Val Leu Thr Pro Val  Thr Ser Asp
    1265                 1270                 1275

Leu Leu  Pro Asn Ser Ala Ala  Pro Gly Gln Leu Thr  Val Ala Gln
    1280                 1285                 1290

Ile Asn  Lys Met Tyr Thr Ser  Met Gly Gly Ile Glu  Pro Lys Glu
    1295                 1300                 1305

Leu Phe  Val Val Gly Lys Pro  Ile Gly His Ser Arg  Ser Pro Ile
    1310                 1315                 1320

Leu His  Asn Thr Gly Tyr Glu  Ile Leu Gly Leu Pro  His Lys Phe
    1325                 1330                 1335

Asp Lys  Phe Glu Thr Glu Ser  Ala Gln Leu Val Lys  Glu Lys Leu
    1340                 1345                 1350

Leu Asp  Gly Asn Lys Asn Phe  Gly Gly Ala Ala Val  Thr Ile Pro
    1355                 1360                 1365

Leu Lys  Leu Asp Ile Met Gln  Tyr Met Asp Glu Leu  Thr Asp Ala
    1370                 1375                 1380

Ala Lys  Val Ile Gly Ala Val  Asn Thr Val Ile Pro  Leu Gly Asn
    1385                 1390                 1395

Lys Lys  Phe Lys Gly Asp Asn  Thr Asp Trp Leu Gly  Ile Arg Asn
    1400                 1405                 1410

Ala Leu  Ile Asn Asn Gly Val  Pro Glu Tyr Val Gly  His Thr Ala
    1415                 1420                 1425

Gly Leu  Val Ile Gly Ala Gly  Gly Thr Ser Arg Ala  Ala Leu Tyr
    1430                 1435                 1440

Ala Leu  His Ser Leu Gly Cys  Lys Lys Ile Phe Ile  Ile Asn Arg
    1445                 1450                 1455

Thr Thr  Ser Lys Leu Lys Pro  Leu Ile Glu Ser Leu  Pro Ser Glu
    1460                 1465                 1470

Phe Asn  Ile Ile Gly Ile Glu  Ser Thr Lys Ser Ile  Glu Glu Ile
    1475                 1480                 1485

Lys Glu  His Val Gly Val Ala  Val Ser Cys Val Pro  Ala Asp Lys
    1490                 1495                 1500

Pro Leu  Asp Asp Glu Leu Leu  Ser Lys Leu Glu Arg  Phe Leu Val
    1505                 1510                 1515

Lys Gly  Ala His Ala Ala Phe  Val Pro Thr Leu Leu  Glu Ala Pro
    1520                 1525                 1530

Tyr Lys  Pro Ser Val Thr Pro  Val Met Thr Ile Ser  Gln Asp Lys
    1535                 1540                 1545

Tyr Gln  Trp His Val Val Pro  Gly Ser Gln Met Leu  Val His Gln
    1550                 1555                 1560

Gly Val  Ala Gln Phe Glu Lys  Trp Thr Gly Phe Lys  Gly Pro Phe
    1565                 1570                 1575

Lys Ala  Ile Phe Asp Ala Val  Thr Lys Glu
    1580                 1585
```

-continued

<210> SEQ ID NO 7
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 7
atggtgcagt tagccaaagt cccaattcta ggaaatgata ttatccacgt tgggtataac 60
attcatgacc atttggttga aaccataatt aaacattgtc cttcttcgac atacgttatt 120
tgcaatgata cgaacttgag taaagttcca tactaccagc aattagtcct ggaattcaag 180
gcttctttgc cagaaggctc tcgtttactt acttatgttg ttaaaccagg tgagacaagt 240
aaaagtagag aaaccaaagc gcagctagaa gattatcttt tagtggaagg atgtactcgt 300
gatacggtta tggtagcgat cggtggtggt gttattggtg acatgattgg gttcgttgca 360
tctacattta tgagaggtgt tcgtgttgtc caagtaccaa catccttatt ggcaatggtc 420
gattcctcca ttggtggtaa aactgctatt gacactcctc taggtaaaaa ctttattggt 480
gcattttggc aaccaaaatt tgtccttgta gatattaaat ggctagaaac gttagccaag 540
agagagttta tcaatgggat ggcagaagtt atcaagactg cttgtatttg gaacgctgac 600
gaatttacta gattagaatc aaacgcttcg ttgttcttaa atgttgttaa tggggcaaaa 660
aatgtcaagg ttaccaatca attgacaaac gagattgacg agatatcgaa tacagatatt 720
gaagctatgt tggatcatac atataagtta gttcttgaga gtattaaggt caaagcggaa 780
gttgtctctt cggatgaacg tgaatccagt ctaagaaacc ttttgaactt cggacattct 840
attggtcatg cttatgaagc tatactaacc ccacaagcat tacatggtga atgtgtgtcc 900
attggtatgg ttaaagaggc ggaattatcc cgttatttcg gtattctctc ccctacccaa 960
gttgcacgtc tatccaagat tttggttgcc tacgggttgc ctgtttcgcc tgatgagaaa 1020
tggtttaaag agctaacctt acataagaaa acaccattgg atatcttatt gaagaaaatg 1080
agtattgaca agaaaaacga gggttccaaa aagaaggtgg tcattttaga aagtattggt 1140
aagtgctatg gtgactccgc tcaatttgtt agcgatgaag acctgagatt tattctaaca 1200
gatgaaaccc tcgtttaccc cttcaaggac atccctgctg atcaacagaa agttgttatc 1260
ccccctggtt ctaagtccat ctccaatcgt gctttaattc ttgctgccct cggtgaaggt 1320
caatgtaaaa tcaagaactt attacattct gatgatacta aacatatgtt aaccgctgtt 1380
catgaattga aaggtgctac gatatcatgg gaagataatg gtgagacggt agtggtggaa 1440
ggacatggtg gttccacatt gtcagcttgt gctgacccct tatatctagg taatgcaggt 1500
actgcatcta gatttttgac ttccttggct gccttggtca attctacttc aagccaaaag 1560
tatatcgttt taactggtaa cgcaagaatg caacaaagac caattgctcc tttggtcgat 1620
tctttgcgtg ctaatggtac taaaattgag tacttgaata atgaaggttc cctgccaatc 1680
aaagtttata ctgattcggt attcaaaggt ggtagaattg aattagctgc tacagtttct 1740
tctcagtacg tatcctctat cttgatgtgt gccccatacg ctgaagaacc tgtaactttg 1800
gctcttgttg gtggtaagcc aatctctaaa ttgtacgtcg atatgacaat aaaaatgatg 1860
gaaaaattcg gtatcaatgt tgaaacttct actacagaac cttacactta ttatattcca 1920
aagggacatt atattaaccc atcagaatac gtcattgaaa gtgatgcctc aagtgctaca 1980
tacccattgg ccttcgccgc aatgactggt actaccgtaa cggttccaaa cattggtttt 2040
gagtcgttac aaggtgatgc cagatttgca agagatgtct tgaaacctat gggttgtaaa 2100

-continued ataactcaaa cggcaacttc aactactgtt tcgggtcctc ctgtaggtac tttaaagcca 2160
ttaaaacatg ttgatatgga gccaatgact gatgcgttct taactgcatg tgttgttgcc 2220
gctatttcgc acgacagtga tccaaattct gcaaatacaa ccaccattga aggtattgca 2280
aaccagcgtg tcaaagagtg taacagaatt ttggccatgg ctacagagct cgccaaattt 2340
ggcgtcaaaa ctacagaatt accagatggt attcaagtcc atggtttaaa ctcgataaaa 2400
gatttgaagg ttccttccga ctcttctgga cctgtcggtg tatgcacata tgatgatcat 2460
cgtgtggcca tgagtttctc gcttcttgca ggaatggtaa attctcaaaa tgaacgtgac 2520
gaagttgcta atcctgtaag aatacttgaa agacattgta ctggtaaaac ctggcctggc 2580
tggtgggatg tgttacattc cgaactaggt gccaaattag atggtgcaga acctttagag 2640
tgcacatcca aaaagaactc aaagaaaagc gttgtcatta ttggcatgag agcagctggc 2700
aaaactacta taagtaaatg gtgcgcatcc gctctgggtt acaaattagt tgacctagac 2760
gagctgtttg agcaacagca taacaatcaa agtgttaaac aatttgttgt ggagaacggt 2820
tgggagaagt tccgtgagga agaaacaaga attttcaagg aagttattca aaattacggc 2880
gatgatggat atgttttctc aacaggtggc ggtattgttg aaagcgctga gtctagaaaa 2940
gccttaaaag attttgcctc atcaggtgga tacgttttac acttacatag ggatattgag 3000
gagacaattg tctttttaca aagtgatcct tcaagacctg cctatgtgga agaaattcgt 3060
gaagtttgga acagaaggga ggggtggtat aaagaatgct caaatttctc tttctttgct 3120
cctcattgct ccgcagaagc tgagttccaa gctctaagaa gatcgtttag taagtacatt 3180
gcaaccatta caggtgtcag agaaatagaa attccaagcg gaagatctgc ctttgtgtgt 3240
ttaacctttg atgacttaac tgaacaaact gagaatttga ctccaatctg ttatggttgt 3300
gaggctgtag aggtcagagt agaccatttg gctaattact ctgctgattt cgtgagtaaa 3360
cagttatcta tattgcgtaa agccactgac agtattccta tcatttttac tgtgcgaacc 3420
atgaagcaag gtggcaactt tcctgatgaa gagttcaaaa ccttgagaga gctatacgat 3480
attgccttga agaatggtgt tgaattcctt gacttagaac taactttacc tactgatatc 3540
caatatgagg ttattaacaa aaggggcaac accaagatca ttggttccca tcatgacttc 3600
caaggattat actcctggga cgacgctgaa tgggaaaaca gattcaatca agcgttaact 3660
cttgatgtgg atgttgtaaa atttgtgggt acggctgtta atttcgaaga taatttgaga 3720
ctggaacact ttagggatac acacaagaat aagcctttaa ttgcagttaa tatgacttct 3780
aaaggtagca tttctcgtgt tttgaataat gttttaacac ctgtgacatc agatttattg 3840
cctaactccg ctgcccctgg ccaattgaca gtagcacaaa ttaacaagat gtatacatct 3900
atgggaggta tcgagcctaa ggaactgttt gttgttggaa agccaattgg ccactctaga 3960
tcgccaattt tacataacac tggctatgaa attttaggtt tacctcacaa gttcgataaa 4020
tttgaaactg aatccgcaca attggtgaaa gaaaaacttt tggacggaaa caagaacttt 4080
ggcggtgctg cagtcacaat tcctctgaaa ttagatataa tgcagtacat ggatgaattg 4140
actgatgctg ctaaagttat tggtgctgta aacacagtta taccattggg taacaagaag 4200
tttaagggtg ataataccga ctggttaggt atccgtaatg ccttaattaa caatggcgtt 4260
cccgaatatg ttggtcatac cgctggtttg gttatcggtg caggtggcac ttctagagcc 4320
gccctttacg ccttgcacag tttaggttgc aaaaagatct tcataatcaa caggacaact 4380
tcgaaattga agccattaat agagtcactt ccatctgaat tcaacattat tggaatagag 4440
tccactaaat ctatagaaga gattaaggaa cacgttggcg ttgctgtcag ctgtgtaaaa 4500

```
gccgacaaac cattagatga cgaactttta agtaagctgg agagattcct tgtgaaaggt   4560

gcccatgctg cttttgtacc aaccttattg gaagccgcat acaaaccaag cgttactccc   4620

gttatgacaa tttcacaaga caaatatcaa tggcacgttg tccctggatc acaaatgtta   4680

gtacaccaag gtgtagctca gtttgaaaag tggacaggat tcaagggccc tttcaaggcc   4740

atttttgatg ccgttacgaa agagtag                                       4767


<210> SEQ ID NO 8
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 8

Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
```

-continued

```
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735
```

```
Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                1005

Asp Pro  Ser Arg Pro Ala Tyr  Val Glu Glu Ile Arg  Glu Val Trp
    1010                1015                1020

Asn Arg  Arg Glu Gly Trp Tyr  Lys Glu Cys Ser Asn  Phe Ser Phe
    1025                1030                1035

Phe Ala  Pro His Cys Ser Ala  Glu Ala Glu Phe Gln  Ala Leu Arg
    1040                1045                1050

Arg Ser  Phe Ser Lys Tyr Ile  Ala Thr Ile Thr Gly  Val Arg Glu
    1055                1060                1065

Ile Glu  Ile Pro Ser Gly Arg  Ser Ala Phe Val Cys  Leu Thr Phe
    1070                1075                1080

Asp Asp  Leu Thr Glu Gln Thr  Glu Asn Leu Thr Pro  Ile Cys Tyr
    1085                1090                1095

Gly Cys  Glu Ala Val Glu Val  Arg Val Asp His Leu  Ala Asn Tyr
    1100                1105                1110

Ser Ala  Asp Phe Val Ser Lys  Gln Leu Ser Ile Leu  Arg Lys Ala
    1115                1120                1125

Thr Asp  Ser Ile Pro Ile Ile  Phe Thr Val Arg Thr  Met Lys Gln
    1130                1135                1140
```

```
Gly Gly  Asn Phe Pro Asp Glu  Glu Phe Lys Thr Leu  Arg Glu Leu
    1145                 1150                 1155

Tyr Asp  Ile Ala Leu Lys Asn  Gly Val Glu Phe Leu  Asp Leu Glu
    1160                 1165                 1170

Leu Thr  Leu Pro Thr Asp Ile  Gln Tyr Glu Val Ile  Asn Lys Arg
    1175                 1180                 1185

Gly Asn  Thr Lys Ile Ile Gly  Ser His His Asp Phe  Gln Gly Leu
    1190                 1195                 1200

Tyr Ser  Trp Asp Asp Ala Glu  Trp Glu Asn Arg Phe  Asn Gln Ala
    1205                 1210                 1215

Leu Thr  Leu Asp Val Asp Val  Val Lys Phe Val Gly  Thr Ala Val
    1220                 1225                 1230

Asn Phe  Glu Asp Asn Leu Arg  Leu Glu His Phe Arg  Asp Thr His
    1235                 1240                 1245

Lys Asn  Lys Pro Leu Ile Ala  Val Asn Met Thr Ser  Lys Gly Ser
    1250                 1255                 1260

Ile Ser  Arg Val Leu Asn Asn  Val Leu Thr Pro Val  Thr Ser Asp
    1265                 1270                 1275

Leu Leu  Pro Asn Ser Ala Ala  Pro Gly Gln Leu Thr  Val Ala Gln
    1280                 1285                 1290

Ile Asn  Lys Met Tyr Thr Ser  Met Gly Gly Ile Glu  Pro Lys Glu
    1295                 1300                 1305

Leu Phe  Val Val Gly Lys Pro  Ile Gly His Ser Arg  Ser Pro Ile
    1310                 1315                 1320

Leu His  Asn Thr Gly Tyr Glu  Ile Leu Gly Leu Pro  His Lys Phe
    1325                 1330                 1335

Asp Lys  Phe Glu Thr Glu Ser  Ala Gln Leu Val Lys  Glu Lys Leu
    1340                 1345                 1350

Leu Asp  Gly Asn Lys Asn Phe  Gly Gly Ala Ala Val  Thr Ile Pro
    1355                 1360                 1365

Leu Lys  Leu Asp Ile Met Gln  Tyr Met Asp Glu Leu  Thr Asp Ala
    1370                 1375                 1380

Ala Lys  Val Ile Gly Ala Val  Asn Thr Val Ile Pro  Leu Gly Asn
    1385                 1390                 1395

Lys Lys  Phe Lys Gly Asp Asn  Thr Asp Trp Leu Gly  Ile Arg Asn
    1400                 1405                 1410

Ala Leu  Ile Asn Asn Gly Val  Pro Glu Tyr Val Gly  His Thr Ala
    1415                 1420                 1425

Gly Leu  Val Ile Gly Ala Gly  Gly Thr Ser Arg Ala  Ala Leu Tyr
    1430                 1435                 1440

Ala Leu  His Ser Leu Gly Cys  Lys Lys Ile Phe Ile  Ile Asn Arg
    1445                 1450                 1455

Thr Thr  Ser Lys Leu Lys Pro  Leu Ile Glu Ser Leu  Pro Ser Glu
    1460                 1465                 1470

Phe Asn  Ile Ile Gly Ile Glu  Ser Thr Lys Ser Ile  Glu Glu Ile
    1475                 1480                 1485

Lys Glu  His Val Gly Val Ala  Val Ser Cys Val Lys  Ala Asp Lys
    1490                 1495                 1500

Pro Leu  Asp Asp Glu Leu Leu  Ser Lys Leu Glu Arg  Phe Leu Val
    1505                 1510                 1515

Lys Gly  Ala His Ala Ala Phe  Val Pro Thr Leu Leu  Glu Ala Ala
    1520                 1525                 1530

Tyr Lys  Pro Ser Val Thr Pro  Val Met Thr Ile Ser  Gln Asp Lys
```

```
    1535                1540                1545

Tyr Gln  Trp His Val Val Pro  Gly Ser Gln Met Leu  Val His Gln
    1550                1555                1560

Gly Val  Ala Gln Phe Glu Lys  Trp Thr Gly Phe Lys  Gly Pro Phe
    1565                1570                1575

Lys Ala  Ile Phe Asp Ala Val  Thr Lys Glu
    1580                1585
```

```
<210> SEQ ID NO 9
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 9

atggtgcagt tagccaaagt cccaattcta ggaaatgata ttatccacgt tgggtataac     60

attcatgacc atttggttga aaccataatt aaacattgtc cttcttcgac atacgttatt    120

tgcaatgata cgaacttgag taaagttcca tactaccagc aattagtcct ggaattcaag    180

gcttctttgc cagaaggctc tcgtttactt acttatgttg ttaaaccagg tgagacaagt    240

aaaagtagag aaaccaaagc gcagctagaa gattatcttt tagtggaagg atgtactcgt    300

gatacggtta tggtagcgat cggtggtggt gttattggtg acatgattgg gttcgttgca    360

tctacattta tgagaggtgt tcgtgttgtc caagtaccaa catccttatt ggcaatggtc    420

gattcctcca ttggtggtaa aactgctatt gacactcctc taggtaaaaa ctttattggt    480

gcattttggc aaccaaaatt tgtccttgta gatattaaat ggctagaaac gttagccaag    540

agagagttta tcaatgggat ggcagaagtt atcaagactg cttgtatttg gaacgctgac    600

gaatttacta gattagaatc aaacgcttcg ttgttcttaa atgttgttaa tggggcaaaa    660

aatgtcaagg ttaccaatca attgacaaac gagattgacg agatatcgaa tacagatatt    720

gaagctatgt tggatcatac atataagtta gttcttgaga gtattaaggt caaagcggaa    780

gttgtctctt cggatgaacg tgaatccagt ctaagaaacc ttttgaactt cggacattct    840

attggtcatg cttatgaagc tatactaacc ccacaagcat tacatggtga atgtgtgtcc    900

attggtatgg ttaaagaggc ggaattatcc cgttatttcg gtattctctc ccctacccaa    960

gttgcacgtc tatccaagat tttggttgcc tacgggttgc ctgtttcgcc tgatgagaaa   1020

tggtttaaag agctaacctt acataagaaa acaccattgg atatcttatt gaagaaaatg   1080

agtattgaca agaaaaacga gggttccaaa aagaaggtgg tcattttaga aagtattggt   1140

aagtgctatg gtgactccgc tcaatttgtt agcgatgaag acctgagatt tattctaaca   1200

gatgaaaccc tcgtttaccc cttcaaggac atccctgctg atcaacagaa agttgttatc   1260

ccccctggtt ctaagtccat ctccaatcgt gctttaattc ttgctgccct cggtgaaggt   1320

caatgtaaaa tcaagaactt attacattct gatgatacta aacatatgtt aaccgctgtt   1380

catgaattga aaggtgctac gatatcatgg gaagataatg gtgagacggt agtggtggaa   1440

ggacatggtg gttccacatt gtcagcttgt gctgacccct tatatctagg taatgcaggt   1500

actgcatcta gatttttgac ttccttggct gccttggtca attctacttc aagccaaaag   1560

tatatcgttt taactggtaa cgcaagaatg caacaaagac caattgctcc tttggtcgat   1620

tctttgcgtg ctaatggtac taaaattgag tacttgaata atgaaggttc cctgccaatc   1680

aaagtttata ctgattcggt attcaaaggt ggtagaattg aattagctgc tacagtttct   1740
```

-continued

```
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
gagctgtttg agcaacagca taacaatcaa agtgttaaac aatttgttgt ggagaacggt   2820
tgggagaagt tccgtgagga agaaacaaga attttcaagg aagttattca aaattacggc   2880
gatgatggat atgttttctc aacaggtggc ggtattgttg aaagcgctga gtctagaaaa   2940
gccttaaaag attttgcctc atcaggtgga tacgttttac acttacatag ggatattgag   3000
gagacaattg tctttttaca aagtgatcct tcaagacctg cctatgtgga agaaattcgt   3060
gaagtttgga acagaaggga ggggtggtat aaagaatgct caaatttctc tttctttgct   3120
cctcattgct ccgcagaagc tgagttccaa gctctaagaa gatcgtttag taagtacatt   3180
gcaaccatta caggtgtcag agaaatagaa attccaagcg gaagatctgc ctttgtgtgt   3240
ttaacctttg atgacttaac tgaacaaact gagaatttga ctccaatctg ttatggttgt   3300
gaggctgtag aggtcagagt agaccatttg gctaattact ctgctgattt cgtgagtaaa   3360
cagttatcta tattgcgtaa agccactgac agtattccta tcatttttac tgtgcgaacc   3420
atgaagcaag gtggcaactt tcctgatgaa gagttcaaaa ccttgagaga gctatacgat   3480
attgccttga agaatggtgt tgaattcctt gacttagaac taactttacc tactgatatc   3540
caatatgagg ttattaacaa aaggggcaac accaagatca ttggttccca tcatgacttc   3600
caaggattat actcctggga cgacgctgaa tgggaaaaca gattcaatca agcgttaact   3660
cttgatgtgg atgttgtaaa atttgtgggt acggctgtta atttcgaaga taatttgaga   3720
ctggaacact ttagggatac acacaagaat aagcctttaa ttgcagttaa tatgacttct   3780
aaaggtagca tttctcgtgt tttgaataat gttttaacac ctgtgacatc agatttattg   3840
cctaactccg ctgcccctgg ccaattgaca gtagcacaaa ttaacaagat gtatacatct   3900
atgggaggta tcgagcctaa ggaactgttt gttgttggaa agccaattgg ccactctaga   3960
tcgccaattt tacataacac tggctatgaa attttaggtt tacctcacaa gttcgataaa   4020
tttgaaactg aatccgcaca attggtgaaa gaaaaacttt tggacggaaa caagaacttt   4080
ggcggtgctg cagtcacaat tcctctgaaa ttagatataa tgcagtacat ggatgaattg   4140
```

```
actgatgctg ctaaagttat tggtgctgta aacacagtta taccattggg taacaagaag   4200

tttaagggtg ataataccga ctggttaggt atccgtaatg ccttaattaa caatggcgtt   4260

cccgaatatg ttggtcatac cgctggtttg gttatcggtg caggtggcac ttctagagcc   4320

gccctttacg ccttgcacag tttaggttgc aaaaagatct tcataatcaa ctggacaact   4380

tcgaaattga agccattaat agagtcactt ccatctgaat tcaacattat tggaatagag   4440

tccactaaat ctatagaaga gattaaggaa cacgttggcg ttgctgtcag ctgtgtacca   4500

gccgacaaac cattagatga cgaactttta agtaagctgg agagattcct tgtgaaaggt   4560

gcccatgctg cttttgtacc aaccttattg gaagccgcat acaaaccaag cgttactccc   4620

gttatgacaa tttcacaaga caaatatcaa tggcacgttg tccctggatc acaaatgtta   4680

gtacaccaag gtgtagctca gtttgaaaag tggacaggat tcaagggccc tttcaaggcc   4740

atttttgatg ccgttacgaa agagtag                                        4767
```

```
<210> SEQ ID NO 10
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 10

Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
```

-continued

```
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670
```

-continued

```
Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                1005

Asp Pro  Ser Arg Pro Ala Tyr  Val Glu Glu Ile Arg  Glu Val Trp
    1010                1015                1020

Asn Arg  Arg Glu Gly Trp Tyr  Lys Glu Cys Ser Asn  Phe Ser Phe
    1025                1030                1035

Phe Ala  Pro His Cys Ser Ala  Glu Ala Glu Phe Gln  Ala Leu Arg
    1040                1045                1050

Arg Ser  Phe Ser Lys Tyr Ile  Ala Thr Ile Thr Gly  Val Arg Glu
    1055                1060                1065

Ile Glu  Ile Pro Ser Gly Arg  Ser Ala Phe Val Cys  Leu Thr Phe
    1070                1075                1080
```

-continued

```
Asp Asp Leu Thr Glu Gln Thr Glu Asn Leu Thr Pro Ile Cys Tyr
    1085                1090                1095

Gly Cys Glu Ala Val Glu Val Arg Val Asp His Leu Ala Asn Tyr
    1100                1105                1110

Ser Ala Asp Phe Val Ser Lys Gln Leu Ser Ile Leu Arg Lys Ala
    1115                1120                1125

Thr Asp Ser Ile Pro Ile Ile Phe Thr Val Arg Thr Met Lys Gln
    1130                1135                1140

Gly Gly Asn Phe Pro Asp Glu Glu Phe Lys Thr Leu Arg Glu Leu
    1145                1150                1155

Tyr Asp Ile Ala Leu Lys Asn Gly Val Glu Phe Leu Asp Leu Glu
    1160                1165                1170

Leu Thr Leu Pro Thr Asp Ile Gln Tyr Glu Val Ile Asn Lys Arg
    1175                1180                1185

Gly Asn Thr Lys Ile Ile Gly Ser His His Asp Phe Gln Gly Leu
    1190                1195                1200

Tyr Ser Trp Asp Asp Ala Glu Trp Glu Asn Arg Phe Asn Gln Ala
    1205                1210                1215

Leu Thr Leu Asp Val Asp Val Val Lys Phe Val Gly Thr Ala Val
    1220                1225                1230

Asn Phe Glu Asp Asn Leu Arg Leu Glu His Phe Arg Asp Thr His
    1235                1240                1245

Lys Asn Lys Pro Leu Ile Ala Val Asn Met Thr Ser Lys Gly Ser
    1250                1255                1260

Ile Ser Arg Val Leu Asn Asn Val Leu Thr Pro Val Thr Ser Asp
    1265                1270                1275

Leu Leu Pro Asn Ser Ala Ala Pro Gly Gln Leu Thr Val Ala Gln
    1280                1285                1290

Ile Asn Lys Met Tyr Thr Ser Met Gly Gly Ile Glu Pro Lys Glu
    1295                1300                1305

Leu Phe Val Val Gly Lys Pro Ile Gly His Ser Arg Ser Pro Ile
    1310                1315                1320

Leu His Asn Thr Gly Tyr Glu Ile Leu Gly Leu Pro His Lys Phe
    1325                1330                1335

Asp Lys Phe Glu Thr Glu Ser Ala Gln Leu Val Lys Glu Lys Leu
    1340                1345                1350

Leu Asp Gly Asn Lys Asn Phe Gly Gly Ala Ala Val Thr Ile Pro
    1355                1360                1365

Leu Lys Leu Asp Ile Met Gln Tyr Met Asp Glu Leu Thr Asp Ala
    1370                1375                1380

Ala Lys Val Ile Gly Ala Val Asn Thr Val Ile Pro Leu Gly Asn
    1385                1390                1395

Lys Lys Phe Lys Gly Asp Asn Thr Asp Trp Leu Gly Ile Arg Asn
    1400                1405                1410

Ala Leu Ile Asn Asn Gly Val Pro Glu Tyr Val Gly His Thr Ala
    1415                1420                1425

Gly Leu Val Ile Gly Ala Gly Gly Thr Ser Arg Ala Ala Leu Tyr
    1430                1435                1440

Ala Leu His Ser Leu Gly Cys Lys Lys Ile Phe Ile Ile Asn Trp
    1445                1450                1455

Thr Thr Ser Lys Leu Lys Pro Leu Ile Glu Ser Leu Pro Ser Glu
    1460                1465                1470

Phe Asn Ile Ile Gly Ile Glu Ser Thr Lys Ser Ile Glu Glu Ile
```

```
    1475                1480                1485

Lys Glu  His Val Gly Val Ala  Val Ser Cys Val Pro  Ala Asp Lys
    1490                1495                1500

Pro Leu  Asp Asp Glu Leu Leu  Ser Lys Leu Glu Arg  Phe Leu Val
    1505                1510                1515

Lys Gly  Ala His Ala Ala Phe  Val Pro Thr Leu Leu  Glu Ala Ala
    1520                1525                1530

Tyr Lys  Pro Ser Val Thr Pro  Val Met Thr Ile Ser  Gln Asp Lys
    1535                1540                1545

Tyr Gln  Trp His Val Val Pro  Gly Ser Gln Met Leu  Val His Gln
    1550                1555                1560

Gly Val  Ala Gln Phe Glu Lys  Trp Thr Gly Phe Lys  Gly Pro Phe
    1565                1570                1575

Lys Ala  Ile Phe Asp Ala Val  Thr Lys Glu
    1580                1585
```

<210> SEQ ID NO 11
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 11

```
atggtgcagt tagccaaagt cccaattcta ggaaatgata ttatccacgt tgggtataac     60

attcatgacc atttggttga aaccataatt aaacattgtc cttcttcgac atacgttatt    120

tgcaatgata cgaacttgag taaagttcca tactaccagc aattagtcct ggaattcaag    180

gcttctttgc cagaaggctc tcgtttactt acttatgttg ttaaaccagg tgagacaagt    240

aaaagtagag aaaccaaagc gcagctagaa gattatcttt tagtggaagg atgtactcgt    300

gatacggtta tggtagcgat cggtggtggt gttattggtg acatgattgg gttcgttgca    360

tctacattta tgagaggtgt tcgtgttgtc caagtaccaa catccttatt ggcaatggtc    420

gattcctcca ttggtggtaa aactgctatt gacactcctc taggtaaaaa ctttattggt    480

gcattttggc aaccaaaatt tgtccttgta gatattaaat ggctagaaac gttagccaag    540

agagagttta tcaatgggat ggcagaagtt atcaagactg cttgtatttg gaacgctgac    600

gaatttacta gattagaatc aaacgcttcg ttgttcttaa atgttgttaa tggggcaaaa    660

aatgtcaagg ttaccaatca attgacaaac gagattgacg agatatcgaa tacagatatt    720

gaagctatgt tggatcatac atataagtta gttcttgaga gtattaaggt caaagcggaa    780

gttgtctctt cggatgaacg tgaatccagt ctaagaaacc ttttgaactt cggacattct    840

attggtcatg cttatgaagc tatactaacc ccacaagcat tacatggtga atgtgtgtcc    900

attggtatgg ttaaagaggc ggaattatcc cgttatttcg gtattctctc ccctacccaa    960

gttgcacgtc tatccaagat tttggttgcc tacgggttgc ctgtttcgcc tgatgagaaa   1020

tggtttaaag agctaacctt acataagaaa acaccattgg atatcttatt gaagaaaatg   1080

agtattgaca agaaaaacga gggttccaaa aagaaggtgg tcattttaga aagtattggt   1140

aagtgctatg gtgactccgc tcaatttgtt agcgatgaag acctgagatt tattctaaca   1200

gatgaaaccc tcgtttaccc cttcaaggac atccctgctg atcaacagaa agttgttatc   1260

ccccctggtt ctaagtccat ctccaatcgt gctttaattc ttgctgccct cggtgaaggt   1320

caatgtaaaa tcaagaactt attacattct gatgatacta aacatatgtt aaccgctgtt   1380
```

-continued

```
catgaattga aaggtgctac gatatcatgg gaagataatg gtgagacggt agtggtggaa   1440
ggacatggtg gttccacatt gtcagcttgt gctgacccct tatatctagg taatgcaggt   1500
actgcatcta gatttttgac ttccttggct gccttggtca attctacttc aagccaaaag   1560
tatatcgttt taactggtaa cgcaagaatg caacaaagac caattgctcc tttggtcgat   1620
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
gagctgtttg agcaacagca taacaatcaa agtgttaaac aatttgttgt ggagaacggt   2820
tgggagaagt tccgtgagga agaaacaaga attttcaagg aagttattca aaattacggc   2880
gatgatggat atgttttctc aacaggtggc ggtattgttg aaagcgctga gtctagaaaa   2940
gccttaaaag attttgcctc atcaggtgga tacgttttac acttacatag ggatattgag   3000
gagacaattg tctttttaca aagtgatcct tcaagacctg cctatgtgga agaaattcgt   3060
gaagtttgga acagaaggga ggggtggtat aaagaatgct caaatttctc tttctttgct   3120
cctcattgct ccgcagaagc tgagttccaa gctctaagaa gatcgtttag taagtacatt   3180
gcaaccatta caggtgtcag agaaatagaa attccaagcg gaagatctgc ctttgtgtgt   3240
ttaacctttg atgacttaac tgaacaaact gagaatttga ctccaatctg ttatggttgt   3300
gaggctgtag aggtcagagt agaccatttg gctaattact ctgctgattt cgtgagtaaa   3360
cagttatcta tattgcgtaa agccactgac agtattccta tcatttttac tgtgcgaacc   3420
atgaagcaag gtggcaactt tcctgatgaa gagttcaaaa ccttgagaga gctatacgat   3480
attgccttga agaatggtgt tgaattcctt gacttagaac taactttacc tactgatatc   3540
caatatgagg ttattaacaa aaggggcaac accaagatca ttggttccca tcatgacttc   3600
caaggattat actcctggga cgacgctgaa tgggaaaaca gattcaatca agcgttaact   3660
cttgatgtgg atgttgtaaa atttgtgggt acggctgtta atttcgaaga taatttgaga   3720
ctggaacact ttagggatac acacaagaat aagcctttaa ttgcagttaa tatgacttct   3780
```

```
aaaggtagca tttctcgtgt tttgaataat gttttaacac ctgtgacatc agatttattg   3840

cctaactccg ctgcccctgg ccaattgaca gtagcacaaa ttaacaagat gtatacatct   3900

atgggaggta tcgagcctaa ggaactgttt gttgttggaa agccaattgg ccactctaga   3960

tcgccaattt tacataacac tggctatgaa attttaggtt tacctcacaa gttcgataaa   4020

tttgaaactg aatccgcaca attgggaaaa gaaaaacttt tggacggaaa caagaacttt   4080

ggcggtgctg cagtcacaat tcctctgaaa ttagatataa tgcagtacat ggatgaattg   4140

actgatgctg ctaaagttat tggtgctgta aacacagtta taccattggg taacaagaag   4200

tttaagggtg ataataccga ctggttaggt atccgtaatg ccttaattaa caatggcgtt   4260

cccgaatatg ttggtcatac cgctggtttg gttatcggtg caggtggcac ttctagagcc   4320

gccctttacg ccttgcacag tttaggttgc aaaaagatct tcataatcaa caggacaact   4380

tcgaaattga agccattaat agagtcactt ccatctgaat tcaacattat tggaatagag   4440

tccactaaat ctatagaaga gattaaggaa cacgttggcg ttgctgtcag ctgtgtacca   4500

gccgacaaac cattagatga cgaactttta agtaagctgg agagattcct tgtgaaaggt   4560

gcccatgctg cttttgtacc aaccttattg gaagccgcat acaaaccaag cgttactccc   4620

gttatgacaa tttcacaaga caaatatcaa tggcacgttg tccctggatc acaaatgtta   4680

gtacaccaag gtgtagctca gtttgaaaag tggacaggat tcaagggccc tttcaaggcc   4740

atttttgatg ccgttacgaa agagtag                                        4767
```

<210> SEQ ID NO 12
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 12

```
Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
```

-continued

```
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605
```

```
Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                 1005

Asp Pro  Ser Arg Pro Ala Tyr  Val Glu Glu Ile Arg  Glu Val Trp
    1010                 1015                 1020
```

Asn Arg Arg Glu Gly Trp Tyr Lys Glu Cys Ser Asn Phe Ser Phe
1025 1030 1035

Phe Ala Pro His Cys Ser Ala Glu Ala Glu Phe Gln Ala Leu Arg
1040 1045 1050

Arg Ser Phe Ser Lys Tyr Ile Ala Thr Ile Thr Gly Val Arg Glu
1055 1060 1065

Ile Glu Ile Pro Ser Gly Arg Ser Ala Phe Val Cys Leu Thr Phe
1070 1075 1080

Asp Asp Leu Thr Glu Gln Thr Glu Asn Leu Thr Pro Ile Cys Tyr
1085 1090 1095

Gly Cys Glu Ala Val Glu Val Arg Val Asp His Leu Ala Asn Tyr
1100 1105 1110

Ser Ala Asp Phe Val Ser Lys Gln Leu Ser Ile Leu Arg Lys Ala
1115 1120 1125

Thr Asp Ser Ile Pro Ile Ile Phe Thr Val Arg Thr Met Lys Gln
1130 1135 1140

Gly Gly Asn Phe Pro Asp Glu Glu Phe Lys Thr Leu Arg Glu Leu
1145 1150 1155

Tyr Asp Ile Ala Leu Lys Asn Gly Val Glu Phe Leu Asp Leu Glu
1160 1165 1170

Leu Thr Leu Pro Thr Asp Ile Gln Tyr Glu Val Ile Asn Lys Arg
1175 1180 1185

Gly Asn Thr Lys Ile Ile Gly Ser His His Asp Phe Gln Gly Leu
1190 1195 1200

Tyr Ser Trp Asp Asp Ala Glu Trp Glu Asn Arg Phe Asn Gln Ala
1205 1210 1215

Leu Thr Leu Asp Val Asp Val Val Lys Phe Val Gly Thr Ala Val
1220 1225 1230

Asn Phe Glu Asp Asn Leu Arg Leu Glu His Phe Arg Asp Thr His
1235 1240 1245

Lys Asn Lys Pro Leu Ile Ala Val Asn Met Thr Ser Lys Gly Ser
1250 1255 1260

Ile Ser Arg Val Leu Asn Asn Val Leu Thr Pro Val Thr Ser Asp
1265 1270 1275

Leu Leu Pro Asn Ser Ala Ala Pro Gly Gln Leu Thr Val Ala Gln
1280 1285 1290

Ile Asn Lys Met Tyr Thr Ser Met Gly Gly Ile Glu Pro Lys Glu
1295 1300 1305

Leu Phe Val Val Gly Lys Pro Ile Gly His Ser Arg Ser Pro Ile
1310 1315 1320

Leu His Asn Thr Gly Tyr Glu Ile Leu Gly Leu Pro His Lys Phe
1325 1330 1335

Asp Lys Phe Glu Thr Glu Ser Ala Gln Leu Gly Lys Glu Lys Leu
1340 1345 1350

Leu Asp Gly Asn Lys Asn Phe Gly Gly Ala Ala Val Thr Ile Pro
1355 1360 1365

Leu Lys Leu Asp Ile Met Gln Tyr Met Asp Glu Leu Thr Asp Ala
1370 1375 1380

Ala Lys Val Ile Gly Ala Val Asn Thr Val Ile Pro Leu Gly Asn
1385 1390 1395

Lys Lys Phe Lys Gly Asp Asn Thr Asp Trp Leu Gly Ile Arg Asn
1400 1405 1410

Ala Leu Ile Asn Asn Gly Val Pro Glu Tyr Val Gly His Thr Ala

```
    1415                1420                1425

Gly Leu  Val Ile Gly Ala Gly  Gly Thr Ser Arg Ala  Ala Leu Tyr
    1430                1435                1440

Ala Leu  His Ser Leu Gly Cys  Lys Lys Ile Phe Ile  Ile Asn Arg
    1445                1450                1455

Thr Thr  Ser Lys Leu Lys Pro  Leu Ile Glu Ser Leu  Pro Ser Glu
    1460                1465                1470

Phe Asn  Ile Ile Gly Ile Glu  Ser Thr Lys Ser Ile  Glu Glu Ile
    1475                1480                1485

Lys Glu  His Val Gly Val Ala  Val Ser Cys Val Pro  Ala Asp Lys
    1490                1495                1500

Pro Leu  Asp Asp Glu Leu Leu  Ser Lys Leu Glu Arg  Phe Leu Val
    1505                1510                1515

Lys Gly  Ala His Ala Ala Phe  Val Pro Thr Leu Leu  Glu Ala Ala
    1520                1525                1530

Tyr Lys  Pro Ser Val Thr Pro  Val Met Thr Ile Ser  Gln Asp Lys
    1535                1540                1545

Tyr Gln  Trp His Val Val Pro  Gly Ser Gln Met Leu  Val His Gln
    1550                1555                1560

Gly Val  Ala Gln Phe Glu Lys  Trp Thr Gly Phe Lys  Gly Pro Phe
    1565                1570                1575

Lys Ala  Ile Phe Asp Ala Val  Thr Lys Glu
    1580                1585


<210> SEQ ID NO 13
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 13

atggtgcagt tagccaaagt cccaattcta ggaaatgata ttatccacgt tgggtataac     60

attcatgacc atttggttga aaccataatt aaacattgtc cttcttcgac atacgttatt    120

tgcaatgata cgaacttgag taaagttcca tactaccagc aattagtcct ggaattcaag    180

gcttctttgc cagaaggctc tcgtttactt acttatgttg ttaaaccagg tgagacaagt    240

aaaagtagag aaaccaaagc gcagctagaa gattatcttt tagtggaagg atgtactcgt    300

gatacggtta tggtagcgat cggtggtggt gttattggtg acatgattgg gttcgttgca    360

tctacattta tgagaggtgt tcgtgttgtc caagtaccaa catccttatt ggcaatggtc    420

gattcctcca ttggtggtaa aactgctatt gacactcctc taggtaaaaa ctttattggt    480

gcattttggc aaccaaaatt tgtccttgta gatattaaat ggctagaaac gttagccaag    540

agagagttta tcaatgggat ggcagaagtt atcaagactg cttgtatttg gaacgctgac    600

gaatttacta gattagaatc aaacgcttcg ttgttcttaa atgttgttaa tggggcaaaa    660

aatgtcaagg ttaccaatca attgacaaac gagattgacg agatatcgaa tacagatatt    720

gaagctatgt tggatcatac atataagtta gttcttgaga gtattaaggt caaagcggaa    780

gttgtctctt cggatgaacg tgaatccagt ctaagaaacc ttttgaactt cggacattct    840

attggtcatg cttatgaagc tatactaacc ccacaagcat tacatggtga atgtgtgtcc    900

attggtatgg ttaaagaggc ggaattatcc cgttatttcg gtattctctc ccctacccaa    960

gttgcacgtc tatccaagat tttggttgcc tacgggttgc ctgtttcgcc tgatgagaaa   1020
```

tggtttaaag agctaacctt acataagaaa acaccattgg atatcttatt gaagaaaatg 1080
agtattgaca agaaaaacga gggttccaaa aagaaggtgg tcattttaga aagtattggt 1140
aagtgctatg gtgactccgc tcaatttgtt agcgatgaag acctgagatt tattctaaca 1200
gatgaaaccc tcgtttaccc cttcaaggac atccctgctg atcaacagaa agttgttatc 1260
ccccctggtt ctaagtccat ctccaatcgt gctttaattc ttgctgccct cggtgaaggt 1320
caatgtaaaa tcaagaactt attacattct gatgatacta aacatatgtt aaccgctgtt 1380
catgaattga aaggtgctac gatatcatgg gaagataatg gtgagacggt agtggtggaa 1440
ggacatggtg gttccacatt gtcagcttgt gctgacccct tatatctagg taatgcaggt 1500
actgcatcta gatttttgac ttccttggct gccttggtca attctacttc aagccaaaag 1560
tatatcgttt taactggtaa cgcaagaatg caacaaagac caattgctcc tttggtcgat 1620
tctttgcgtg ctaatggtac taaaattgag tacttgaata atgaaggttc cctgccaatc 1680
aaagtttata ctgattcggt attcaaaggt ggtagaattg aattagctgc tacagtttct 1740
tctcagtacg tatcctctat cttgatgtgt gccccatacg ctgaagaacc tgtaactttg 1800
gctcttgttg gtggtaagcc aatctctaaa ttgtacgtcg atatgacaat aaaaatgatg 1860
gaaaaattcg gtatcaatgt tgaaacttct actacagaac cttacactta ttatattcca 1920
aagggacatt atattaaccc atcagaatac gtcattgaaa gtgatgcctc aagtgctaca 1980
tacccattgg ccttcgccgc aatgactggt actaccgtaa cggttccaaa cattggtttt 2040
gagtcgttac aaggtgatgc cagatttgca agagatgtct tgaaacctat gggttgtaaa 2100
ataactcaaa cggcaacttc aactactgtt tcgggtcctc ctgtaggtac tttaaagcca 2160
ttaaaacatg ttgatatgga gccaatgact gatgcgttct taactgcatg tgttgttgcc 2220
gctatttcgc acgacagtga tccaaattct gcaaatacaa ccaccattga aggtattgca 2280
aaccagcgtg tcaaagagtg taacagaatt ttggccatgg ctacagagct cgccaaattt 2340
ggcgtcaaaa ctacagaatt accagatggt attcaagtcc atggtttaaa ctcgataaaa 2400
gatttgaagg ttccttccga ctcttctgga cctgtcggtg tatgcacata tgatgatcat 2460
cgtgtggcca tgagtttctc gcttcttgca ggaatggtaa attctcaaaa tgaacgtgac 2520
gaagttgcta atcctgtaag aatacttgaa agacattgta ctggtaaaac ctggcctggc 2580
tggtgggatg tgttacattc cgaactaggt gccaaattag atggtgcaga acctttagag 2640
tgcacatcca aaaagaactc aaagaaaagc gttgtcatta ttggcatgag agcagctggc 2700
aaaactacta taagtaaatg gtgcgcatcc gctctgggtt acaaattagt tgacctagac 2760
gagctgtttg agcaacagca taacaatcaa agtgttaaac aatttgttgt ggagaacggt 2820
tgggagaagt tccgtgagga agaaacaaga attttcaagg aagttattca aaattacggc 2880
gatgatggat atgttttctc aacaggtggc ggtattgttg aaagcgctga gtctagaaaa 2940
gccttaaaag attttgcctc atcaggtgga tacgttttac acttacatag ggatattgag 3000
gagacaattg tctttttaca aagtgatcct tcaagacctg cctatgtgga agaaattcgt 3060
gaagtttgga acagaaggga ggggtggtat aaagaatgct caaatttctc tttctttgct 3120
cctcattgct ccgcagaagc tgagttccaa gctctaagaa gatcgtttag taagtacatt 3180
gcaaccatta caggtgtcag agaaatagaa attccaagcg gaagatctgc ctttgtgtgt 3240
ttaacctttg atgacttaac tgaacaaact gagaatttga ctccaatctg ttatggttgt 3300
gaggctgtag aggtcagagt agaccatttg gctaattact ctgctgattt cgtgagtaaa 3360
cagttatcta tattgcgtaa agccactgac agtattccta tcatttttac tgtgcgaacc 3420

```
atgaagcaag gtggcaactt tcctgatgaa gagttcaaaa ccttgagaga gctatacgat   3480

attgccttga agaatggtgt tgaattcctt gacttagaac taactttacc tactgatatc   3540

caatatgagg ttattaacaa aaggggcaac accaagatca ttggttccca tcatgacttc   3600

caaggattat actcctggga cgacgctgaa tgggaaaaca gattcaatca agcgttaact   3660

cttgatgtgg atgttgtaaa atttgtgggt acggctgtta atttcgaaga taatttgaga   3720

ctggaacact ttagggatac acacaagaat aagcctttaa ttgcagttaa tatgacttct   3780

aaaggtagca tttctcgtgt tttgaataat gttttaacac ctgtgacatc agatttattg   3840

cctaactccg ctgcccctgg ccaattgaca gtagcacaaa ttaacaagat gtatacatct   3900

atgggaggta tcgagcctaa ggaactgttt gttgttggaa agccaattgg ccactctaga   3960

tcgccaattt tacataacac tggctatgaa attttaggtt tacctcacaa gttcgataaa   4020

tttgaaactg aatccgcaca attggtgaaa gaaaaacttt tggacggaaa caagaacttt   4080

ggcggtgctg cagtcaggat tcctctgaaa ttagatataa tgcagtacat ggatgaattg   4140

actgatgctg ctaaagttat tggtgctgta aacacagtta taccattggg taacaagaag   4200

tttaagggtg ataataccga ctggttaggt atccgtaatg ccttaattaa caatggcgtt   4260

cccgaatatg ttggtcatac cgctggtttg gttatcggtg caggtggcac ttctagagcc   4320

gccctttacg ccttgcacag tttaggttgc aaaaagatct tcataatcaa caggacaact   4380

tcgaaattga agccattaat agagtcactt ccatctgaat tcaacattat tggaatagag   4440

tccactaaat ctatagaaga gattaaggaa cacgttggcg ttgctgtcag ctgtgtacca   4500

gccgacaaac cattagatga cgaacttta agtaagctgg agagattcct tgtgaaaggt   4560

gcccatgctg cttttgtacc aaccttattg gaagccgcat acaaaccaag cgttactccc   4620

gttatgacaa tttcacaaga caaatatcaa tggcacgttg tccctggatc acaaatgtta   4680

gtacaccaag gtgtagctca gtttgaaaag tggacaggat tcaagggccc tttcaaggcc   4740

atttttgatg ccgttacgaa agagtag                                       4767
```

<210> SEQ ID NO 14
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 14

```
Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
```

-continued

```
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540
```

-continued

Asn Gly Thr Lys Ile Glu Tyr Leu Asn Asn Glu Gly Ser Leu Pro Ile
545 550 555 560

Lys Val Tyr Thr Asp Ser Val Phe Lys Gly Gly Arg Ile Glu Leu Ala
565 570 575

Ala Thr Val Ser Ser Gln Tyr Val Ser Ser Ile Leu Met Cys Ala Pro
580 585 590

Tyr Ala Glu Glu Pro Val Thr Leu Ala Leu Val Gly Gly Lys Pro Ile
595 600 605

Ser Lys Leu Tyr Val Asp Met Thr Ile Lys Met Met Glu Lys Phe Gly
610 615 620

Ile Asn Val Glu Thr Ser Thr Thr Glu Pro Tyr Thr Tyr Tyr Ile Pro
625 630 635 640

Lys Gly His Tyr Ile Asn Pro Ser Glu Tyr Val Ile Glu Ser Asp Ala
645 650 655

Ser Ser Ala Thr Tyr Pro Leu Ala Phe Ala Ala Met Thr Gly Thr Thr
660 665 670

Val Thr Val Pro Asn Ile Gly Phe Glu Ser Leu Gln Gly Asp Ala Arg
675 680 685

Phe Ala Arg Asp Val Leu Lys Pro Met Gly Cys Lys Ile Thr Gln Thr
690 695 700

Ala Thr Ser Thr Thr Val Ser Gly Pro Pro Val Gly Thr Leu Lys Pro
705 710 715 720

Leu Lys His Val Asp Met Glu Pro Met Thr Asp Ala Phe Leu Thr Ala
725 730 735

Cys Val Val Ala Ala Ile Ser His Asp Ser Asp Pro Asn Ser Ala Asn
740 745 750

Thr Thr Thr Ile Glu Gly Ile Ala Asn Gln Arg Val Lys Glu Cys Asn
755 760 765

Arg Ile Leu Ala Met Ala Thr Glu Leu Ala Lys Phe Gly Val Lys Thr
770 775 780

Thr Glu Leu Pro Asp Gly Ile Gln Val His Gly Leu Asn Ser Ile Lys
785 790 795 800

Asp Leu Lys Val Pro Ser Asp Ser Ser Gly Pro Val Gly Val Cys Thr
805 810 815

Tyr Asp Asp His Arg Val Ala Met Ser Phe Ser Leu Leu Ala Gly Met
820 825 830

Val Asn Ser Gln Asn Glu Arg Asp Glu Val Ala Asn Pro Val Arg Ile
835 840 845

Leu Glu Arg His Cys Thr Gly Lys Thr Trp Pro Gly Trp Trp Asp Val
850 855 860

Leu His Ser Glu Leu Gly Ala Lys Leu Asp Gly Ala Glu Pro Leu Glu
865 870 875 880

Cys Thr Ser Lys Lys Asn Ser Lys Lys Ser Val Val Ile Ile Gly Met
885 890 895

Arg Ala Ala Gly Lys Thr Thr Ile Ser Lys Trp Cys Ala Ser Ala Leu
900 905 910

Gly Tyr Lys Leu Val Asp Leu Asp Glu Leu Phe Glu Gln Gln His Asn
915 920 925

Asn Gln Ser Val Lys Gln Phe Val Val Glu Asn Gly Trp Glu Lys Phe
930 935 940

Arg Glu Glu Glu Thr Arg Ile Phe Lys Glu Val Ile Gln Asn Tyr Gly
945 950 955 960

-continued

```
Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                 1005

Asp Pro  Ser Arg Pro Ala Tyr  Val Glu Glu Ile Arg  Glu Val Trp
    1010                 1015                 1020

Asn Arg  Arg Glu Gly Trp Tyr  Lys Glu Cys Ser Asn  Phe Ser Phe
    1025                 1030                 1035

Phe Ala  Pro His Cys Ser Ala  Glu Ala Glu Phe Gln  Ala Leu Arg
    1040                 1045                 1050

Arg Ser  Phe Ser Lys Tyr Ile  Ala Thr Ile Thr Gly  Val Arg Glu
    1055                 1060                 1065

Ile Glu  Ile Pro Ser Gly Arg  Ser Ala Phe Val Cys  Leu Thr Phe
    1070                 1075                 1080

Asp Asp  Leu Thr Glu Gln Thr  Glu Asn Leu Thr Pro  Ile Cys Tyr
    1085                 1090                 1095

Gly Cys  Glu Ala Val Glu Val  Arg Val Asp His Leu  Ala Asn Tyr
    1100                 1105                 1110

Ser Ala  Asp Phe Val Ser Lys  Gln Leu Ser Ile Leu  Arg Lys Ala
    1115                 1120                 1125

Thr Asp  Ser Ile Pro Ile Ile  Phe Thr Val Arg Thr  Met Lys Gln
    1130                 1135                 1140

Gly Gly  Asn Phe Pro Asp Glu  Glu Phe Lys Thr Leu  Arg Glu Leu
    1145                 1150                 1155

Tyr Asp  Ile Ala Leu Lys Asn  Gly Val Glu Phe Leu  Asp Leu Glu
    1160                 1165                 1170

Leu Thr  Leu Pro Thr Asp Ile  Gln Tyr Glu Val Ile  Asn Lys Arg
    1175                 1180                 1185

Gly Asn  Thr Lys Ile Ile Gly  Ser His His Asp Phe  Gln Gly Leu
    1190                 1195                 1200

Tyr Ser  Trp Asp Asp Ala Glu  Trp Glu Asn Arg Phe  Asn Gln Ala
    1205                 1210                 1215

Leu Thr  Leu Asp Val Asp Val  Val Lys Phe Val Gly  Thr Ala Val
    1220                 1225                 1230

Asn Phe  Glu Asp Asn Leu Arg  Leu Glu His Phe Arg  Asp Thr His
    1235                 1240                 1245

Lys Asn  Lys Pro Leu Ile Ala  Val Asn Met Thr Ser  Lys Gly Ser
    1250                 1255                 1260

Ile Ser  Arg Val Leu Asn Asn  Val Leu Thr Pro Val  Thr Ser Asp
    1265                 1270                 1275

Leu Leu  Pro Asn Ser Ala Ala  Pro Gly Gln Leu Thr  Val Ala Gln
    1280                 1285                 1290

Ile Asn  Lys Met Tyr Thr Ser  Met Gly Gly Ile Glu  Pro Lys Glu
    1295                 1300                 1305

Leu Phe  Val Val Gly Lys Pro  Ile Gly His Ser Arg  Ser Pro Ile
    1310                 1315                 1320

Leu His  Asn Thr Gly Tyr Glu  Ile Leu Gly Leu Pro  His Lys Phe
    1325                 1330                 1335

Asp Lys  Phe Glu Thr Glu Ser  Ala Gln Leu Val Lys  Glu Lys Leu
    1340                 1345                 1350

Leu Asp  Gly Asn Lys Asn Phe  Gly Gly Ala Ala Val  Arg Ile Pro
```

```
    1355                1360                1365

Leu Lys  Leu Asp Ile Met Gln  Tyr Met Asp Glu Leu  Thr Asp Ala
    1370                1375                1380

Ala Lys  Val Ile Gly Ala Val  Asn Thr Val Ile Pro  Leu Gly Asn
    1385                1390                1395

Lys Lys  Phe Lys Gly Asp Asn  Thr Asp Trp Leu Gly  Ile Arg Asn
    1400                1405                1410

Ala Leu  Ile Asn Asn Gly Val  Pro Glu Tyr Val Gly  His Thr Ala
    1415                1420                1425

Gly Leu  Val Ile Gly Ala Gly  Gly Thr Ser Arg Ala  Ala Leu Tyr
    1430                1435                1440

Ala Leu  His Ser Leu Gly Cys  Lys Lys Ile Phe Ile  Ile Asn Arg
    1445                1450                1455

Thr Thr  Ser Lys Leu Lys Pro  Leu Ile Glu Ser Leu  Pro Ser Glu
    1460                1465                1470

Phe Asn  Ile Ile Gly Ile Glu  Ser Thr Lys Ser Ile  Glu Glu Ile
    1475                1480                1485

Lys Glu  His Val Gly Val Ala  Val Ser Cys Val Pro  Ala Asp Lys
    1490                1495                1500

Pro Leu  Asp Asp Glu Leu Leu  Ser Lys Leu Glu Arg  Phe Leu Val
    1505                1510                1515

Lys Gly  Ala His Ala Ala Phe  Val Pro Thr Leu Leu  Glu Ala Ala
    1520                1525                1530

Tyr Lys  Pro Ser Val Thr Pro  Val Met Thr Ile Ser  Gln Asp Lys
    1535                1540                1545

Tyr Gln  Trp His Val Val Pro  Gly Ser Gln Met Leu  Val His Gln
    1550                1555                1560

Gly Val  Ala Gln Phe Glu Lys  Trp Thr Gly Phe Lys  Gly Pro Phe
    1565                1570                1575

Lys Ala  Ile Phe Asp Ala Val  Thr Lys Glu
    1580                1585


<210> SEQ ID NO 15
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 15

atggtgcagt tagccaaagt cccaattcta ggaaatgata ttatccacgt tgggtataac      60

attcatgacc atttggttga aaccataatt aaacattgtc cttcttcgac atacgttatt     120

tgcaatgata cgaacttgag taaagttcca tactaccagc aattagtcct ggaattcaag     180

gcttctttgc cagaaggctc tcgtttactt acttatgttg ttaaaccagg tgagacaagt     240

aaaagtagag aaaccaaagc gcagctagaa gattatcttt tagtggaagg atgtactcgt     300

gatacggtta tggtagcgat cggtggtggt gttattggtg acatgattgg gttcgttgca     360

tctacattta tgagaggtgt tcgtgttgtc caagtaccaa catccttatt ggcaatggtc     420

gattcctcca ttggtggtaa aactgctatt gacactcctc taggtaaaaa ctttattggt     480

gcattttggc aaccaaaatt tgtccttgta gatattaaat ggctagaaac gttagccaag     540

agagagttta tcaatgggat ggcagaagtt atcaagactg cttgtatttg gaacgctgac     600

gaatttacta gattagaatc aaacgcttcg ttgttcttaa atgttgttaa tggggcaaaa     660
```

-continued aatgtcaagg ttaccaatca attgacaaac gagattgacg agatatcgaa tacagatatt 720
gaagctatgt tggatcatac atataagtta gttcttgaga gtattaaggt caaagcggaa 780
gttgtctctt cggatgaacg tgaatccagt ctaagaaacc ttttgaactt cggacattct 840
attggtcatg cttatgaagc tatactaacc ccacaagcat tacatggtga atgtgtgtcc 900
attggtatgg ttaaagaggc ggaattatcc cgttatttcg gtattctctc ccctacccaa 960
gttgcacgtc tatccaagat tttggttgcc tacgggttgc ctgtttcgcc tgatgagaaa 1020
tggtttaaag agctaacctt acataagaaa acaccattgg atatcttatt gaagaaaatg 1080
agtattgaca agaaaaacga gggttccaaa aagaaggtgg tcattttaga aagtattggt 1140
aagtgctatg gtgactccgc tcaatttgtt agcgatgaag acctgagatt tattctaaca 1200
gatgaaaccc tcgtttaccc cttcaaggac atccctgctg atcaacagaa agttgttatc 1260
ccccctggtt ctaagtccat ctccaatcgt gctttaattc ttgctgccct cggtgaaggt 1320
caatgtaaaa tcaagaactt attacattct gatgatacta aacatatgtt aaccgctgtt 1380
catgaattga aaggtgctac gatatcatgg gaagataatg gtgagacggt agtggtggaa 1440
ggacatggtg gttccacatt gtcagcttgt gctgacccct tatatctagg taatgcaggt 1500
actgcatcta gatttttgac ttccttggct gccttggtca attctacttc aagccaaaag 1560
tatatcgttt taactggtaa cgcaagaatg caacaaagac caattgctcc tttggtcgat 1620
tctttgcgtg ctaatggtac taaaattgag tacttgaata atgaaggttc cctgccaatc 1680
aaagtttata ctgattcggt attcaaaggt ggtagaattg aattagctgc tacagtttct 1740
tctcagtacg tatcctctat cttgatgtgt gccccatacg ctgaagaacc tgtaactttg 1800
gctcttgttg gtggtaagcc aatctctaaa ttgtacgtcg atatgacaat aaaaatgatg 1860
gaaaaattcg gtatcaatgt tgaaacttct actacagaac cttacactta ttatattcca 1920
aagggacatt atattaaccc atcagaatac gtcattgaaa gtgatgcctc aagtgctaca 1980
tacccattgg ccttcgccgc aatgactggt actaccgtaa cggttccaaa cattggtttt 2040
gagtcgttac aaggtgatgc cagatttgca agagatgtct tgaaacctat gggttgtaaa 2100
ataactcaaa cggcaacttc aactactgtt tcgggtcctc ctgtaggtac tttaaagcca 2160
ttaaaacatg ttgatatgga gccaatgact gatgcgttct taactgcatg tgttgttgcc 2220
gctatttcgc acgacagtga tccaaattct gcaaatacaa ccaccattga aggtattgca 2280
aaccagcgtg tcaaagagtg taacagaatt ttggccatgg ctacagagct cgccaaattt 2340
ggcgtcaaaa ctacagaatt accagatggt attcaagtcc atggtttaaa ctcgataaaa 2400
gatttgaagg ttccttccga ctcttctgga cctgtcggtg tatgcacata tgatgatcat 2460
cgtgtggcca tgagtttctc gcttcttgca ggaatggtaa attctcaaaa tgaacgtgac 2520
gaagttgcta atcctgtaag aatacttgaa agacattgta ctggtaaaac ctggcctggc 2580
tggtgggatg tgttacattc cgaactaggt gccaaattag atggtgcaga acctttagag 2640
tgcacatcca aaaagaactc aaagaaaagc gttgtcatta ttggcatgag agcagctggc 2700
aaaactacta taagtaaatg gtgcgcatcc gctctgggtt acaaattagt tgacctagac 2760
gagctgtttg agcaacagca taacaatcaa agtgttaaac aatttgttgt ggagaacggt 2820
tgggagaagt tccgtgagga agaaacaaga attttcaagg aagttattca aaattacggc 2880
gatgatggat atgttttctc aacaggtggc ggtattgttg aaagcgctga gtctagaaaa 2940
gccttaaaag attttgcctc atcaggtgga tacgttttac acttacatag ggatattgag 3000
gagacaattg tctttttaca aagtgatcct tcaagacctg cctatgtgga agaaattcgt 3060

-continued

```
gaagtttgga acagaaggga ggggtggtat aaagaatgct caaatttctc tttctttgct   3120

cctcattgct ccgcagaagc tgagttccaa gctctaagaa gatcgtttag taagtacatt   3180

gcaaccatta caggtgtcag agaaatagaa attccaagcg gaagatctgc ctttgtgtgt   3240

ttaacctttg atgacttaac tgaacaaact gagaatttga ctccaatctg ttatggttgt   3300

gaggctgtag aggtcagagt agaccatttg gctaattact ctgctgattt cgtgagtaaa   3360

cagttatcta tattgcgtaa agccactgac agtattccta tcatttttac tgtgcgaacc   3420

atgaagcaag gtggcaactt tcctgatgaa gagttcaaaa ccttgagaga gctatacgat   3480

attgccttga agaatggtgt tgaattcctt gacttagaac taactttacc tactgatatc   3540

caatatgagg ttattaacaa aaggggcaac accaagatca ttggttccca tcatgacttc   3600

caaggattat actcctggga cgacgctgaa tgggaaaaca gattcaatca agcgttaact   3660

cttgatgtgg atgttgtaaa atttgtgggt acggctgtta atttcgaaga taatttgaga   3720

ctggaacact ttagggatac acacaagaat aagcctttaa ttgcagttaa tatgacttct   3780

aaaggtagca tttctcgtgt tttgaataat gttttaacac ctgtgacatc agatttattg   3840

cctaactccg ctgcccctgg ccaattgaca gtagcacaaa ttaacaagat gtatacatct   3900

atgggaggta tcgagcctaa ggaactgttt gttgttggaa agccaattgg ccactctaga   3960

tcgccaattt tacataacac tggctatgaa attttaggtt tacctcacaa gttcgataaa   4020

tttgaaactg aatccgcaca attggtgaaa gaaaaacttt tggacggaaa caagaacttt   4080

ggcggtgctg cagtcacaat tcctctgaaa ttagatataa tgcagtacat ggatgaattg   4140

actgatgctg ctaaagttca tggtgctgta aacacagtta taccattggg taacaagaag   4200

tttaagggtg ataataccga ctggttaggt atccgtaatg ccttaattaa caatggcgtt   4260

cccgaatatg ttggtcatac cgctggtttg gttatcggtg caggtggcac ttctagagcc   4320

gccctttacg ccttgcacag tttaggttgc aaaaagatct tcataatcaa caggacaact   4380

tcgaaattga agccattaat agagtcactt ccatctgaat tcaacattat tggaatagag   4440

tccactaaat ctatagaaga gattaaggaa cacgttggcg ttgctgtcag ctgtgtacca   4500

gccgacaaac cattagatga cgaactttta agtaagctgg agagattcct tgtgaaaggt   4560

gcccatgctg cttttgtacc aaccttattg gaagccgcat acaaaccaag cgttactccc   4620

gttatgacaa tttcacaaga caaatatcaa tggcacgttg tccctggatc acaaatgtta   4680

gtacaccaag gtgtagctca gtttgaaaag tggacaggat tcaagggccc tttcaaggcc   4740

atttttgatg ccgttacgaa agagtag                                       4767
```

<210> SEQ ID NO 16
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 16

```
Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
```

-continued

```
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480
```

-continued

```
Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895
```

-continued

```
Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                1005

Asp Pro  Ser Arg Pro Ala Tyr  Val Glu Glu Ile Arg  Glu Val Trp
    1010                1015                1020

Asn Arg  Arg Glu Gly Trp Tyr  Lys Glu Cys Ser Asn  Phe Ser Phe
    1025                1030                1035

Phe Ala  Pro His Cys Ser Ala  Glu Ala Glu Phe Gln  Ala Leu Arg
    1040                1045                1050

Arg Ser  Phe Ser Lys Tyr Ile  Ala Thr Ile Thr Gly  Val Arg Glu
    1055                1060                1065

Ile Glu  Ile Pro Ser Gly Arg  Ser Ala Phe Val Cys  Leu Thr Phe
    1070                1075                1080

Asp Asp  Leu Thr Glu Gln Thr  Glu Asn Leu Thr Pro  Ile Cys Tyr
    1085                1090                1095

Gly Cys  Glu Ala Val Glu Val  Arg Val Asp His Leu  Ala Asn Tyr
    1100                1105                1110

Ser Ala  Asp Phe Val Ser Lys  Gln Leu Ser Ile Leu  Arg Lys Ala
    1115                1120                1125

Thr Asp  Ser Ile Pro Ile Ile  Phe Thr Val Arg Thr  Met Lys Gln
    1130                1135                1140

Gly Gly  Asn Phe Pro Asp Glu  Glu Phe Lys Thr Leu  Arg Glu Leu
    1145                1150                1155

Tyr Asp  Ile Ala Leu Lys Asn  Gly Val Glu Phe Leu  Asp Leu Glu
    1160                1165                1170

Leu Thr  Leu Pro Thr Asp Ile  Gln Tyr Glu Val Ile  Asn Lys Arg
    1175                1180                1185

Gly Asn  Thr Lys Ile Ile Gly  Ser His His Asp Phe  Gln Gly Leu
    1190                1195                1200

Tyr Ser  Trp Asp Asp Ala Glu  Trp Glu Asn Arg Phe  Asn Gln Ala
    1205                1210                1215

Leu Thr  Leu Asp Val Asp Val  Val Lys Phe Val Gly  Thr Ala Val
    1220                1225                1230

Asn Phe  Glu Asp Asn Leu Arg  Leu Glu His Phe Arg  Asp Thr His
    1235                1240                1245

Lys Asn  Lys Pro Leu Ile Ala  Val Asn Met Thr Ser  Lys Gly Ser
    1250                1255                1260

Ile Ser  Arg Val Leu Asn Asn  Val Leu Thr Pro Val  Thr Ser Asp
    1265                1270                1275

Leu Leu  Pro Asn Ser Ala Ala  Pro Gly Gln Leu Thr  Val Ala Gln
    1280                1285                1290

Ile Asn  Lys Met Tyr Thr Ser  Met Gly Gly Ile Glu  Pro Lys Glu
```

```
    1295                1300                1305

Leu Phe  Val Val Gly Lys Pro  Ile Gly His Ser Arg  Ser Pro Ile
    1310                1315                1320

Leu His  Asn Thr Gly Tyr Glu  Ile Leu Gly Leu Pro  His Lys Phe
    1325                1330                1335

Asp Lys  Phe Glu Thr Glu Ser  Ala Gln Leu Val Lys  Glu Lys Leu
    1340                1345                1350

Leu Asp  Gly Asn Lys Asn Phe  Gly Gly Ala Ala Val  Thr Ile Pro
    1355                1360                1365

Leu Lys  Leu Asp Ile Met Gln  Tyr Met Asp Glu Leu  Thr Asp Ala
    1370                1375                1380

Ala Lys  Val His Gly Ala Val  Asn Thr Val Ile Pro  Leu Gly Asn
    1385                1390                1395

Lys Lys  Phe Lys Gly Asp Asn  Thr Asp Trp Leu Gly  Ile Arg Asn
    1400                1405                1410

Ala Leu  Ile Asn Asn Gly Val  Pro Glu Tyr Val Gly  His Thr Ala
    1415                1420                1425

Gly Leu  Val Ile Gly Ala Gly  Gly Thr Ser Arg Ala  Ala Leu Tyr
    1430                1435                1440

Ala Leu  His Ser Leu Gly Cys  Lys Lys Ile Phe Ile  Ile Asn Arg
    1445                1450                1455

Thr Thr  Ser Lys Leu Lys Pro  Leu Ile Glu Ser Leu  Pro Ser Glu
    1460                1465                1470

Phe Asn  Ile Ile Gly Ile Glu  Ser Thr Lys Ser Ile  Glu Glu Ile
    1475                1480                1485

Lys Glu  His Val Gly Val Ala  Val Ser Cys Val Pro  Ala Asp Lys
    1490                1495                1500

Pro Leu  Asp Asp Glu Leu Leu  Ser Lys Leu Glu Arg  Phe Leu Val
    1505                1510                1515

Lys Gly  Ala His Ala Ala Phe  Val Pro Thr Leu Leu  Glu Ala Ala
    1520                1525                1530

Tyr Lys  Pro Ser Val Thr Pro  Val Met Thr Ile Ser  Gln Asp Lys
    1535                1540                1545

Tyr Gln  Trp His Val Val Pro  Gly Ser Gln Met Leu  Val His Gln
    1550                1555                1560

Gly Val  Ala Gln Phe Glu Lys  Trp Thr Gly Phe Lys  Gly Pro Phe
    1565                1570                1575

Lys Ala  Ile Phe Asp Ala Val  Thr Lys Glu
    1580                1585
```

<210> SEQ ID NO 17
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 17

```
atggtgcagt tagccaaagt cccaattcta ggaaatgata ttatccacgt tgggtataac      60

attcatgacc atttggttga aaccataatt aaacattgtc cttcttcgac atacgttatt     120

tgcaatgata cgaacttgag taaagttcca tactaccagc aattagtcct ggaattcaag     180

gcttctttgc cagaaggctc tcgtttactt acttatgttg ttaaaccagg tgagacaagt     240

aaaagtagag aaaccaaagc gcagctagaa gattatcttt tagtggaagg atgtactcgt     300
```

-continued

```
gatacggtta tggtagcgat cggtggtggt gttattggtg acatgattgg gttcgttgca    360
tctacattta tgagaggtgt tcgtgttgtc caagtaccaa catccttatt ggcaatggtc    420
gattcctcca ttggtggtaa aactgctatt gacactcctc taggtaaaaa ctttattggt    480
gcattttggc aaccaaaatt tgtccttgta gatattaaat ggctagaaac gttagccaag    540
agagagttta tcaatgggat ggcagaagtt atcaagactg cttgtatttg gaacgctgac    600
gaatttacta gattagaatc aaacgcttcg ttgttcttaa atgttgttaa tggggcaaaa    660
aatgtcaagg ttaccaatca attgacaaac gagattgacg agatatcgaa tacagatatt    720
gaagctatgt tggatcatac atataagtta gttcttgaga gtattaaggt caaagcggaa    780
gttgtctctt cggatgaacg tgaatccagt ctaagaaacc ttttgaactt cggacattct    840
attggtcatg cttatgaagc tatactaacc ccacaagcat tacatggtga atgtgtgtcc    900
attggtatgg ttaaagaggc ggaattatcc cgttatttcg gtattctctc ccctacccaa    960
gttgcacgtc tatccaagat tttggttgcc tacgggttgc ctgtttcgcc tgatgagaaa   1020
tggtttaaag agctaacctt acataagaaa acaccattgg atatcttatt gaagaaaatg   1080
agtattgaca agaaaaacga gggttccaaa aagaaggtgg tcattttaga aagtattggt   1140
aagtgctatg gtgactccgc tcaatttgtt agcgatgaag acctgagatt tattctaaca   1200
gatgaaaccc tcgtttaccc cttcaaggac atccctgctg atcaacagaa agttgttatc   1260
ccccctggtt ctaagtccat ctccaatcgt gctttaattc ttgctgccct cggtgaaggt   1320
caatgtaaaa tcaagaactt attacattct gatgatacta aacatatgtt aaccgctgtt   1380
catgaattga aggtgctac gatatcatgg gaagataatg gtgagacggt agtggtggaa   1440
ggacatggtg gttccacatt gtcagcttgt gctgacccct tatatctagg taatgcaggt   1500
actgcatcta gatttttgac ttccttggct gccttggtca attctacttc aagccaaaag   1560
tatatcgttt taactggtaa cgcaagaatg caacaaagac caattgctcc tttggtcgat   1620
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
```

aaaactacta taagtaaatg gtgcgcatcc gctctgggtt acaaattagt tgacctagac 2760
gagctgtttg agcaacagca taacaatcaa agtgttaaac aatttgttgt ggagaacggt 2820
tgggagaagt tccgtgagga agaaacaaga attttcaagg aagttattca aaattacggc 2880
gatgatggat atgttttctc aacaggtggc ggtattgttg aaagcgctga gtctagaaaa 2940
gccttaaaag attttgcctc atcaggtgga tacgttttac acttacatag ggatattgag 3000
gagacaattg tctttttaca aagtgatcct tcaagacctg cctatgtgga agaaattcgt 3060
gaagtttgga acagaaggga ggggtggtat aaagaatgct caaatttctc tttctttgct 3120
cctcattgct ccgcagaagc tgagttccaa gctctaagaa gatcgtttag taagtacatt 3180
gcaaccatta caggtgtcag agaaatagaa attccaagcg gaagatctgc ctttgtgtgt 3240
ttaacctttg atgacttaac tgaacaaact gagaatttga ctccaatctg ttatggttgt 3300
gaggctgtag aggtcagagt agaccatttg gctaattact ctgctgattt cgtgagtaaa 3360
cagttatcta tattgcgtaa agccactgac agtattccta tcatttttac tgtgcgaacc 3420
atgaagcaag gtggcaactt tcctgatgaa gagttcaaaa ccttgagaga gctatacgat 3480
attgccttga agaatggtgt tgaattcctt gacttagaac taactttacc tactgatatc 3540
caatatgagg ttattaacaa aaggggcaac accaagatca ttggttccca tcatgacttc 3600
caaggattat actcctggga cgacgctgaa tgggaaaaca gattcaatca agcgttaact 3660
cttgatgtgg atgttgtaaa atttgtgggt acggctgtta atttcgaaga taatttgaga 3720
ctggaacact ttagggatac acacaagaat aagcctttaa ttgcagttaa tatgacttct 3780
aaaggtagca tttctcgtgt tttgaataat gttttaacac ctgtgacatc agatttattg 3840
cctaactccg ctgcccctgg ccaattgaca gtagcacaaa ttaacaagat gtatacatct 3900
atgggaggta tcgagcctaa ggaactgttt gttgttggaa agccaattgg ccactctaga 3960
tcgccaattt tacataacac tggctatgaa attttaggtt tacctcacaa gttcgataaa 4020
tttgaaactg aatccgcaca attggtgaaa gaaaaacttt tggacggaaa caagaacttt 4080
ggcggtgctg cagtcacaat tcctctgaaa ttagatataa tgcagtacat ggatgaattg 4140
actgatgctg ctaaagttat tggtgctgta aacacagtta taccattggg taacaagaag 4200
tttaagggtg ataataccga ctggttaggt atccgtaatg ccttaattaa caatggcgtt 4260
cccgaatatg ttggtcatac cgctggtttg gttatcggtg caggtggcac ttctagagcc 4320
gccctttacg ccttgcacag tttaggttgc aaaaagatct tcataatcaa caggacaact 4380
tcgaaattga agccattaat agagtcactt ccatctgaat tcaacattat tggaatagag 4440
tccactaaat ctatagaaga gattaaggaa cacgttggcg ttgctgtcag ctgtgtacca 4500
gccgacaaac cattagatga cgaacttttta agtaagctgg agagattcct tgtgaaaggt 4560
gcccatgctg cttttgtacc aaccttattg gaagccgcat acaaaccaag cgttactccc 4620
gttatgacaa tttcacaaga caaatatcaa tggcacgttg tccctggatc acaaatgtta 4680
gtacaccaag gtgtagctca gtttgaaaag gttacaggat tcaagggccc tttcaaggcc 4740
atttttgatg ccgttacgaa agagtag 4767

<210> SEQ ID NO 18
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 18

```
Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415
```

```
Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830
```

```
Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                1005

Asp Pro  Ser Arg Pro Ala Tyr  Val Glu Glu Ile Arg  Glu Val Trp
    1010                1015                1020

Asn Arg  Arg Glu Gly Trp Tyr  Lys Glu Cys Ser Asn  Phe Ser Phe
    1025                1030                1035

Phe Ala  Pro His Cys Ser Ala  Glu Ala Glu Phe Gln  Ala Leu Arg
    1040                1045                1050

Arg Ser  Phe Ser Lys Tyr Ile  Ala Thr Ile Thr Gly  Val Arg Glu
    1055                1060                1065

Ile Glu  Ile Pro Ser Gly Arg  Ser Ala Phe Val Cys  Leu Thr Phe
    1070                1075                1080

Asp Asp  Leu Thr Glu Gln Thr  Glu Asn Leu Thr Pro  Ile Cys Tyr
    1085                1090                1095

Gly Cys  Glu Ala Val Glu Val  Arg Val Asp His Leu  Ala Asn Tyr
    1100                1105                1110

Ser Ala  Asp Phe Val Ser Lys  Gln Leu Ser Ile Leu  Arg Lys Ala
    1115                1120                1125

Thr Asp  Ser Ile Pro Ile Ile  Phe Thr Val Arg Thr  Met Lys Gln
    1130                1135                1140

Gly Gly  Asn Phe Pro Asp Glu  Glu Phe Lys Thr Leu  Arg Glu Leu
    1145                1150                1155

Tyr Asp  Ile Ala Leu Lys Asn  Gly Val Glu Phe Leu  Asp Leu Glu
    1160                1165                1170

Leu Thr  Leu Pro Thr Asp Ile  Gln Tyr Glu Val Ile  Asn Lys Arg
    1175                1180                1185

Gly Asn  Thr Lys Ile Ile Gly  Ser His His Asp Phe  Gln Gly Leu
    1190                1195                1200

Tyr Ser  Trp Asp Asp Ala Glu  Trp Glu Asn Arg Phe  Asn Gln Ala
    1205                1210                1215

Leu Thr  Leu Asp Val Asp Val  Val Lys Phe Val Gly  Thr Ala Val
    1220                1225                1230

Asn Phe  Glu Asp Asn Leu Arg  Leu Glu His Phe Arg  Asp Thr His
```

```
    1235                1240                1245

Lys Asn  Lys Pro Leu Ile Ala  Val Asn Met Thr Ser  Lys Gly Ser
    1250                1255                1260

Ile Ser  Arg Val Leu Asn Asn  Val Leu Thr Pro Val  Thr Ser Asp
    1265                1270                1275

Leu Leu  Pro Asn Ser Ala Ala  Pro Gly Gln Leu Thr  Val Ala Gln
    1280                1285                1290

Ile Asn  Lys Met Tyr Thr Ser  Met Gly Gly Ile Glu  Pro Lys Glu
    1295                1300                1305

Leu Phe  Val Val Gly Lys Pro  Ile Gly His Ser Arg  Ser Pro Ile
    1310                1315                1320

Leu His  Asn Thr Gly Tyr Glu  Ile Leu Gly Leu Pro  His Lys Phe
    1325                1330                1335

Asp Lys  Phe Glu Thr Glu Ser  Ala Gln Leu Val Lys  Glu Lys Leu
    1340                1345                1350

Leu Asp  Gly Asn Lys Asn Phe  Gly Gly Ala Ala Val  Thr Ile Pro
    1355                1360                1365

Leu Lys  Leu Asp Ile Met Gln  Tyr Met Asp Glu Leu  Thr Asp Ala
    1370                1375                1380

Ala Lys  Val Ile Gly Ala Val  Asn Thr Val Ile Pro  Leu Gly Asn
    1385                1390                1395

Lys Lys  Phe Lys Gly Asp Asn  Thr Asp Trp Leu Gly  Ile Arg Asn
    1400                1405                1410

Ala Leu  Ile Asn Asn Gly Val  Pro Glu Tyr Val Gly  His Thr Ala
    1415                1420                1425

Gly Leu  Val Ile Gly Ala Gly  Gly Thr Ser Arg Ala  Ala Leu Tyr
    1430                1435                1440

Ala Leu  His Ser Leu Gly Cys  Lys Lys Ile Phe Ile  Ile Asn Arg
    1445                1450                1455

Thr Thr  Ser Lys Leu Lys Pro  Leu Ile Glu Ser Leu  Pro Ser Glu
    1460                1465                1470

Phe Asn  Ile Ile Gly Ile Glu  Ser Thr Lys Ser Ile  Glu Glu Ile
    1475                1480                1485

Lys Glu  His Val Gly Val Ala  Val Ser Cys Val Pro  Ala Asp Lys
    1490                1495                1500

Pro Leu  Asp Asp Glu Leu Leu  Ser Lys Leu Glu Arg  Phe Leu Val
    1505                1510                1515

Lys Gly  Ala His Ala Ala Phe  Val Pro Thr Leu Leu  Glu Ala Ala
    1520                1525                1530

Tyr Lys  Pro Ser Val Thr Pro  Val Met Thr Ile Ser  Gln Asp Lys
    1535                1540                1545

Tyr Gln  Trp His Val Val Pro  Gly Ser Gln Met Leu  Val His Gln
    1550                1555                1560

Gly Val  Ala Gln Phe Glu Lys  Val Thr Gly Phe Lys  Gly Pro Phe
    1565                1570                1575

Lys Ala  Ile Phe Asp Ala Val  Thr Lys Glu
    1580                1585
```

<210> SEQ ID NO 19
<211> LENGTH: 4767
<212> TYPE: DNA
<213> ORGANISM: Artificial sequence
<220> FEATURE:
<223> OTHER INFORMATION: Synthetic nucleic acid -continued

<400> SEQUENCE: 19

```
atggtgcagt tagccaaagt cccaattcta ggaaatgata ttatccacgt tgggtataac     60
attcatgacc atttggttga aaccataatt aaacattgtc cttcttcgac atacgttatt    120
tgcaatgata cgaacttgag taaagttcca tactaccagc aattagtcct ggaattcaag    180
gcttctttgc cagaaggctc tcgtttactt acttatgttg ttaaaccagg tgagacaagt    240
aaaagtagag aaaccaaagc gcagctagaa gattatcttt tagtggaagg atgtactcgt    300
gatacggtta tggtagcgat cggtggtggt gttattggtg acatgattgg gttcgttgca    360
tctacattta tgagaggtgt tcgtgttgtc caagtaccaa catccttatt ggcaatggtc    420
gattcctcca ttggtggtaa aactgctatt gacactcctc taggtaaaaa ctttattggt    480
gcattttggc aaccaaaatt tgtccttgta gatattaaat ggctagaaac gttagccaag    540
agagagttta tcaatgggat ggcagaagtt atcaagactg cttgtatttg gaacgctgac    600
gaatttacta gattagaatc aaacgcttcg ttgttcttaa atgttgttaa tggggcaaaa    660
aatgtcaagg ttaccaatca attgacaaac gagattgacg agatatcgaa tacagatatt    720
gaagctatgt tggatcatac atataagtta gttcttgaga gtattaaggt caaagcggaa    780
gttgtctctt cggatgaacg tgaatccagt ctaagaaacc ttttgaactt cggacattct    840
attggtcatg cttatgaagc tatactaacc ccacaagcat tacatggtga atgtgtgtcc    900
attggtatgg ttaaagaggc ggaattatcc cgttatttcg gtattctctc ccctacccaa    960
gttgcacgtc tatccaagat tttggttgcc tacgggttgc ctgtttcgcc tgatgagaaa   1020
tggtttaaag agctaacctt acataagaaa acaccattgg atatcttatt gaagaaaatg   1080
agtattgaca agaaaaacga gggttccaaa aagaaggtgg tcattttaga aagtattggt   1140
aagtgctatg gtgactccgc tcaatttgtt agcgatgaag acctgagatt tattctaaca   1200
gatgaaaccc tcgtttaccc cttcaaggac atccctgctg atcaacagaa agttgttatc   1260
ccccctggtt ctaagtccat ctccaatcgt gctttaattc ttgctgccct cggtgaaggt   1320
caatgtaaaa tcaagaactt attacattct gatgatacta aacatatgtt aaccgctgtt   1380
catgaattga aaggtgctac gatatcatgg gaagataatg gtgagacggt agtggtggaa   1440
ggacatggtg gttccacatt gtcagcttgt gctgacccct tatatctagg taatgcaggt   1500
actgcatcta gatttttgac ttccttggct gccttggtca attctacttc aagccaaaag   1560
tatatcgttt taactggtaa cgcaagaatg caacaaagac caattgctcc tttggtcgat   1620
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
```

-continued

```
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
gagctgtttg agcaacagca taacaatcaa agtgttaaac aatttgttgt ggagaacggt   2820
tgggagaagt tccgtgagga agaaacaaga attttcaagg aagttattca aaattacggc   2880
gatgatggat atgttttctc aacaggtggc ggtattgttg aaagcgctga gtctagaaaa   2940
gccttaaaag attttgcctc atcaggtgga tacgttttac acttacatag ggatattgag   3000
gagacaattg tctttttaca aagtgatcct tcaagacctg cctatgtgga agaaattcgt   3060
gaagtttgga acagaaggga ggggtggtat aaagaatgct caaatttctc tttctttgct   3120
cctcattgct ccgcagaagc tgagttccaa gctctaagaa gatcgtttag taagtacatt   3180
gcaaccatta caggtgtcag agaaatagaa attccaagcg gaagatctgc ctttgtgtgt   3240
ttaacctttg atgacttaac tgaacaaact gagaatttga ctccaatctg ttatggttgt   3300
gaggctgtag aggtcagagt agaccatttg gctaattact ctgctgattt cgtgagtaaa   3360
cagttatcta tattgcgtaa agccactgac agtattccta tcatttttac tgtgcgaacc   3420
atgaagcaag gtggcaactt tcctgatgaa gagttcaaaa ccttgagaga gctatacgat   3480
attgccttga agaatggtgt tgaattcctt gacttagaac taactttacc tactgatatc   3540
caatatgagg ttattaacaa aaggggcaac accaagatca ttggttccca tcatgacttc   3600
caaggattat actcctggga cgacgctgaa tgggaaaaca gattcaatca agcgttaact   3660
cttgatgtgg atgttgtaaa atttgtgggt acggctgtta atttcgaaga taatttgaga   3720
ctggaacact ttagggatac acacaagaat aagcctttaa ttgcagttaa tatgacttct   3780
aaaggtagca tttctcgtgt tttgaataat gttttaacac ctgtgacatc agatttattg   3840
cctaactccg ctgcccctgg ccaattgaca gtagcacaaa ttaacaagat gtatacatct   3900
atgggaggta tcgagcctaa ggaactgttt gttgttggaa agccaattgg ccactctaga   3960
tcgccaattt tacataacac tggctatgaa attttaggtt tacctcacaa gttcgataaa   4020
tttgaaactg aatccgcaca attggtgaaa gaaaaacttt tggacggaaa caagaacttt   4080
ggcggtgctg cagtcacaat tcctctgaaa ttagatataa tgcagtacat ggatgaattg   4140
actgatgctg ctaaagttat tggtgctgta aacaaagtta taccattggg taacaagaag   4200
tttaagggtg ataataccga ctggttaggt atccgtaatg ccttaattaa caatggcgtt   4260
cccgaatatg ttggtcatac cgctggtttg gttatcggtg caggtggcac ttctagagcc   4320
gccctttacg ccttgcacag tttaggttgc aaaaagatct tcataatcaa caggacaact   4380
tcgaaattga agccattaat agagtcactt ccatctgaat tcaacattat tggaatagag   4440
tccactaaat ctatagaaga gattaaggaa cacgttggcg ttgctgtcag ctgtgtacca   4500
gccgacaaac cattagatga cgaactttta agtaagctgg agagattcct tgtgaaaggt   4560
gcccatgctg cttttgtacc aaccttattg gaagccgcat acaaaccaag cgttactccc   4620
gttatgacaa tttcacaaga caaatatcaa tggcacgttg tccctggatc acaaatgtta   4680
```

gtacaccaag gtgtagctca gtttgaaaag tggacaggat tcaagggccc tttcaaggcc 4740
atttttgatg ccgttacgaa agagtag 4767

<210> SEQ ID NO 20
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 20

Met Val Gln Leu Ala Lys Val Pro Ile Leu Gly Asn Asp Ile Ile His
1 5 10 15

Val Gly Tyr Asn Ile His Asp His Leu Val Glu Thr Ile Ile Lys His
20 25 30

Cys Pro Ser Ser Thr Tyr Val Ile Cys Asn Asp Thr Asn Leu Ser Lys
35 40 45

Val Pro Tyr Tyr Gln Gln Leu Val Leu Glu Phe Lys Ala Ser Leu Pro
50 55 60

Glu Gly Ser Arg Leu Leu Thr Tyr Val Val Lys Pro Gly Glu Thr Ser
65 70 75 80

Lys Ser Arg Glu Thr Lys Ala Gln Leu Glu Asp Tyr Leu Leu Val Glu
85 90 95

Gly Cys Thr Arg Asp Thr Val Met Val Ala Ile Gly Gly Gly Val Ile
100 105 110

Gly Asp Met Ile Gly Phe Val Ala Ser Thr Phe Met Arg Gly Val Arg
115 120 125

Val Val Gln Val Pro Thr Ser Leu Leu Ala Met Val Asp Ser Ser Ile
130 135 140

Gly Gly Lys Thr Ala Ile Asp Thr Pro Leu Gly Lys Asn Phe Ile Gly
145 150 155 160

Ala Phe Trp Gln Pro Lys Phe Val Leu Val Asp Ile Lys Trp Leu Glu
165 170 175

Thr Leu Ala Lys Arg Glu Phe Ile Asn Gly Met Ala Glu Val Ile Lys
180 185 190

Thr Ala Cys Ile Trp Asn Ala Asp Glu Phe Thr Arg Leu Glu Ser Asn
195 200 205

Ala Ser Leu Phe Leu Asn Val Val Asn Gly Ala Lys Asn Val Lys Val
210 215 220

Thr Asn Gln Leu Thr Asn Glu Ile Asp Glu Ile Ser Asn Thr Asp Ile
225 230 235 240

Glu Ala Met Leu Asp His Thr Tyr Lys Leu Val Leu Glu Ser Ile Lys
245 250 255

Val Lys Ala Glu Val Val Ser Ser Asp Glu Arg Glu Ser Ser Leu Arg
260 265 270

Asn Leu Leu Asn Phe Gly His Ser Ile Gly His Ala Tyr Glu Ala Ile
275 280 285

Leu Thr Pro Gln Ala Leu His Gly Glu Cys Val Ser Ile Gly Met Val
290 295 300

Lys Glu Ala Glu Leu Ser Arg Tyr Phe Gly Ile Leu Ser Pro Thr Gln
305 310 315 320

Val Ala Arg Leu Ser Lys Ile Leu Val Ala Tyr Gly Leu Pro Val Ser
325 330 335

Pro Asp Glu Lys Trp Phe Lys Glu Leu Thr Leu His Lys Lys Thr Pro
340 345 350

-continued

```
Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765
```

-continued

```
Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                1005

Asp Pro  Ser Arg Pro Ala Tyr  Val Glu Glu Ile Arg  Glu Val Trp
    1010                 1015                 1020

Asn Arg  Arg Glu Gly Trp Tyr  Lys Glu Cys Ser Asn  Phe Ser Phe
    1025                 1030                 1035

Phe Ala  Pro His Cys Ser Ala  Glu Ala Glu Phe Gln  Ala Leu Arg
    1040                 1045                 1050

Arg Ser  Phe Ser Lys Tyr Ile  Ala Thr Ile Thr Gly  Val Arg Glu
    1055                 1060                 1065

Ile Glu  Ile Pro Ser Gly Arg  Ser Ala Phe Val Cys  Leu Thr Phe
    1070                 1075                 1080

Asp Asp  Leu Thr Glu Gln Thr  Glu Asn Leu Thr Pro  Ile Cys Tyr
    1085                 1090                 1095

Gly Cys  Glu Ala Val Glu Val  Arg Val Asp His Leu  Ala Asn Tyr
    1100                 1105                 1110

Ser Ala  Asp Phe Val Ser Lys  Gln Leu Ser Ile Leu  Arg Lys Ala
    1115                 1120                 1125

Thr Asp  Ser Ile Pro Ile Ile  Phe Thr Val Arg Thr  Met Lys Gln
    1130                 1135                 1140

Gly Gly  Asn Phe Pro Asp Glu  Glu Phe Lys Thr Leu  Arg Glu Leu
    1145                 1150                 1155

Tyr Asp  Ile Ala Leu Lys Asn  Gly Val Glu Phe Leu  Asp Leu Glu
    1160                 1165                 1170

Leu Thr  Leu Pro Thr Asp Ile  Gln Tyr Glu Val Ile  Asn Lys Arg
```

```
    1175                1180                1185

Gly Asn  Thr Lys Ile Ile Gly  Ser His His Asp Phe  Gln Gly Leu
    1190                1195                1200

Tyr Ser  Trp Asp Asp Ala Glu  Trp Glu Asn Arg Phe  Asn Gln Ala
    1205                1210                1215

Leu Thr  Leu Asp Val Asp Val  Val Lys Phe Val Gly  Thr Ala Val
    1220                1225                1230

Asn Phe  Glu Asp Asn Leu Arg  Leu Glu His Phe Arg  Asp Thr His
    1235                1240                1245

Lys Asn  Lys Pro Leu Ile Ala  Val Asn Met Thr Ser  Lys Gly Ser
    1250                1255                1260

Ile Ser  Arg Val Leu Asn Asn  Val Leu Thr Pro Val  Thr Ser Asp
    1265                1270                1275

Leu Leu  Pro Asn Ser Ala Ala  Pro Gly Gln Leu Thr  Val Ala Gln
    1280                1285                1290

Ile Asn  Lys Met Tyr Thr Ser  Met Gly Gly Ile Glu  Pro Lys Glu
    1295                1300                1305

Leu Phe  Val Val Gly Lys Pro  Ile Gly His Ser Arg  Ser Pro Ile
    1310                1315                1320

Leu His  Asn Thr Gly Tyr Glu  Ile Leu Gly Leu Pro  His Lys Phe
    1325                1330                1335

Asp Lys  Phe Glu Thr Glu Ser  Ala Gln Leu Val Lys  Glu Lys Leu
    1340                1345                1350

Leu Asp  Gly Asn Lys Asn Phe  Gly Gly Ala Ala Val  Thr Ile Pro
    1355                1360                1365

Leu Lys  Leu Asp Ile Met Gln  Tyr Met Asp Glu Leu  Thr Asp Ala
    1370                1375                1380

Ala Lys  Val Ile Gly Ala Val  Asn Lys Val Ile Pro  Leu Gly Asn
    1385                1390                1395

Lys Lys  Phe Lys Gly Asp Asn  Thr Asp Trp Leu Gly  Ile Arg Asn
    1400                1405                1410

Ala Leu  Ile Asn Asn Gly Val  Pro Glu Tyr Val Gly  His Thr Ala
    1415                1420                1425

Gly Leu  Val Ile Gly Ala Gly  Gly Thr Ser Arg Ala  Ala Leu Tyr
    1430                1435                1440

Ala Leu  His Ser Leu Gly Cys  Lys Lys Ile Phe Ile  Ile Asn Arg
    1445                1450                1455

Thr Thr  Ser Lys Leu Lys Pro  Leu Ile Glu Ser Leu  Pro Ser Glu
    1460                1465                1470

Phe Asn  Ile Ile Gly Ile Glu  Ser Thr Lys Ser Ile  Glu Glu Ile
    1475                1480                1485

Lys Glu  His Val Gly Val Ala  Val Ser Cys Val Pro  Ala Asp Lys
    1490                1495                1500

Pro Leu  Asp Asp Glu Leu Leu  Ser Lys Leu Glu Arg  Phe Leu Val
    1505                1510                1515

Lys Gly  Ala His Ala Ala Phe  Val Pro Thr Leu Leu  Glu Ala Ala
    1520                1525                1530

Tyr Lys  Pro Ser Val Thr Pro  Val Met Thr Ile Ser  Gln Asp Lys
    1535                1540                1545

Tyr Gln  Trp His Val Val Pro  Gly Ser Gln Met Leu  Val His Gln
    1550                1555                1560

Gly Val  Ala Gln Phe Glu Lys  Trp Thr Gly Phe Lys  Gly Pro Phe
    1565                1570                1575
```

```
Lys Ala Ile Phe Asp Ala Val Thr Lys Glu
    1580                1585


<210> SEQ ID NO 21
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 21

atggtgcagt tagccaaagt cccaattcta ggaaatgata ttatccacgt tgggtataac     60
attcatgacc atttggttga aaccataatt aaacattgtc cttcttcgac atacgttatt    120
tgcaatgata cgaacttgag taaagttcca tactaccagc aattagtcct ggaattcaag    180
gcttctttgc cagaaggctc tcgtttactt acttatgttg ttaaaccagg tgagacaagt    240
aaaagtagag aaaccaaagc gcagctagaa gattatcttt tagtggaagg atgtactcgt    300
gatacggtta tggtagcgat cggtggtggt gttattggtg acatgattgg gttcgttgca    360
tctacattta tgagaggtgt tcgtgttgtc caagtaccaa catccttatt ggcaatggtc    420
gattcctcca ttggtggtaa aactgctatt gacactcctc taggtaaaaa ctttattggt    480
gcattttggc aaccaaaatt tgtccttgta gatattaaat ggctagaaac gttagccaag    540
agagagttta tcaatgggat ggcagaagtt atcaagactg cttgtatttg gaacgctgac    600
gaatttacta gattagaatc aaacgcttcg ttgttcttaa atgttgttaa tggggcaaaa    660
aatgtcaagg ttaccaatca attgacaaac gagattgacg agatatcgaa tacagatatt    720
gaagctatgt tggatcatac atataagtta gttcttgaga gtattaaggt caaagcggaa    780
gttgtctctt cggatgaacg tgaatccagt ctaagaaacc ttttgaactt cggacattct    840
attggtcatg cttatgaagc tatactaacc ccacaagcat tacatggtga atgtgtgtcc    900
attggtatgg ttaaagaggc ggaattatcc cgttatttcg gtattctctc ccctacccaa    960
gttgcacgtc tatccaagat tttggttgcc tacgggttgc ctgtttcgcc tgatgagaaa   1020
tggtttaaag agctaacctt acataagaaa acaccattgg atatcttatt gaagaaaatg   1080
agtattgaca agaaaaacga gggttccaaa aagaaggtgg tcattttaga aagtattggt   1140
aagtgctatg gtgactccgc tcaatttgtt agcgatgaag acctgagatt tattctaaca   1200
gatgaaaccc tcgtttaccc cttcaaggac atccctgctg atcaacagaa agttgttatc   1260
ccccctggtt ctaagtccat ctccaatcgt gctttaattc ttgctgccct cggtgaaggt   1320
caatgtaaaa tcaagaactt attacattct gatgatacta aacatatgtt aaccgctgtt   1380
catgaattga aaggtgctac gatatcatgg gaagataatg gtgagacggt agtggtggaa   1440
ggacatggtg gttccacatt gtcagcttgt gctgacccct tatatctagg taatgcaggt   1500
actgcatcta gatttttgac ttccttggct gccttggtca attctacttc aagccaaaag   1560
tatatcgttt taactggtaa cgcaagaatg caacaaagac caattgctcc tttggtcgat   1620
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
```

-continued

```
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
gagctgtttg agcaacagca taacaatcaa agtgttaaac aatttgttgt ggagaacggt   2820
tgggagaagt tccgtgagga agaaacaaga attttcaagg aagttattca aaattacggc   2880
gatgatggat atgttttctc aacaggtggc ggtattgttg aaagcgctga gtctagaaaa   2940
gccttaaaag attttgcctc atcaggtgga tacgttttac acttacatag ggatattgag   3000
gagacaattg tctttttaca aagtgatcct tcaagacctg cctatgtgga agaaattcgt   3060
gaagtttgga acagaaggga ggggtggtat aaagaatgct caaatttctc tttctttgct   3120
cctcattgct ccgcagaagc tgagttccaa gctctaagaa gatcgtttag taagtacatt   3180
gcaaccatta caggtgtcag agaaatagaa attccaagcg gaagatctgc ctttgtgtgt   3240
ttaacctttg atgacttaac tgaacaaact gagaatttga ctccaatctg ttatggttgt   3300
gaggctgtag aggtcagagt agaccatttg gctaattact ctgctgattt cgtgagtaaa   3360
cagttatcta tattgcgtaa agccactgac agtattccta tcatttttac tgtgcgaacc   3420
atgaagcaag gtggcaactt tcctgatgaa gagttcaaaa ccttgagaga gctatacgat   3480
attgccttga agaatggtgt tgaattcctt gacttagaac taactttacc tactgatatc   3540
caatatgagg ttattaacaa aaggggcaac accaagatca ttggttccca tcatgacttc   3600
caaggattat actcctggga cgacgctgaa tgggaaaaca gattcaatca agcgttaact   3660
cttgatgtgg atgttgtaaa atttgtgggt acggctgtta atttcgaaga taatttgaga   3720
ctggaacact ttagggatac acacaagaat aagcctttaa ttgcagttaa tatgacttct   3780
aaaggtagca tttctcgtgt tttgaataat gttttaacac ctgtgacatc agatttattg   3840
cctaactccg ctgcccctgg ccaattgaca gtagcacaaa ttaacaagat gtatacatct   3900
atgggaggta tcgagcctaa ggaactgttt gttgttggaa agccaattgg ccactctaga   3960
tcgccaattt tacataacac tggctatgaa attttaggtt tacctcacaa gttcgataaa   4020
tttgaaactg aatccgcaca attggtgaaa gaaaaacttt tggacggaaa caagaacttt   4080
ggcggtgctg cagtcacaat tcctctgtta ttagatataa tgcagtacat ggatgaattg   4140
actgatgctg ctaaagttat tggtgctgta aacacagtta taccattggg taacaagaag   4200
tttaagggtg ataataccga ctggttaggt atccgtaatg ccttaattaa caatggcgtt   4260
cccgaatatg ttggtcatac cgctggtttg gttatcggtg caggtggcac ttctagagcc   4320
```

```
gcccttttacg ccttgcacag tttaggttgc aaaaagatct tcataatcaa caggacaact   4380

tcgaaattga agccattaat agagtcactt ccatctgaat tcaacattat tggaatagag   4440

tccactaaat ctatagaaga gattaaggaa cacgttggcg ttgctgtcag ctgtgtacca   4500

gccgacaaac cattagatga cgaacttttta agtaagctgg agagattcct tgtgaaaggt   4560

gcccatgctg cttttgtacc aaccttattg gaagccgcat acaaaccaag cgttactccc   4620

gttatgacaa tttcacaaga caaatatcaa tggcacgttg tccctggatc acaaatgtta   4680

gtacaccaag gtgtagctca gtttgaaaag tggacaggat tcaagggccc tttcaaggcc   4740

atttttgatg ccgttacgaa agagtag                                        4767


<210> SEQ ID NO 22
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 22

Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285
```

```
Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700
```

```
Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                1005

Asp Pro  Ser Arg Pro Ala Tyr  Val Glu Glu Ile Arg  Glu Val Trp
    1010                 1015                 1020

Asn Arg  Arg Glu Gly Trp Tyr  Lys Glu Cys Ser Asn  Phe Ser Phe
    1025                 1030                 1035

Phe Ala  Pro His Cys Ser Ala  Glu Ala Glu Phe Gln  Ala Leu Arg
    1040                 1045                 1050

Arg Ser  Phe Ser Lys Tyr Ile  Ala Thr Ile Thr Gly  Val Arg Glu
    1055                 1060                 1065

Ile Glu  Ile Pro Ser Gly Arg  Ser Ala Phe Val Cys  Leu Thr Phe
    1070                 1075                 1080

Asp Asp  Leu Thr Glu Gln Thr  Glu Asn Leu Thr Pro  Ile Cys Tyr
    1085                 1090                 1095

Gly Cys  Glu Ala Val Glu Val  Arg Val Asp His Leu  Ala Asn Tyr
    1100                 1105                 1110

Ser Ala  Asp Phe Val Ser Lys  Gln Leu Ser Ile Leu  Arg Lys Ala
```

```
    1115                1120                1125

Thr Asp  Ser Ile Pro Ile Ile  Phe Thr Val Arg Thr  Met Lys Gln
    1130                1135                1140

Gly Gly  Asn Phe Pro Asp Glu  Glu Phe Lys Thr Leu  Arg Glu Leu
    1145                1150                1155

Tyr Asp  Ile Ala Leu Lys Asn  Gly Val Glu Phe Leu  Asp Leu Glu
    1160                1165                1170

Leu Thr  Leu Pro Thr Asp Ile  Gln Tyr Glu Val Ile  Asn Lys Arg
    1175                1180                1185

Gly Asn  Thr Lys Ile Ile Gly  Ser His His Asp Phe  Gln Gly Leu
    1190                1195                1200

Tyr Ser  Trp Asp Asp Ala Glu  Trp Glu Asn Arg Phe  Asn Gln Ala
    1205                1210                1215

Leu Thr  Leu Asp Val Asp Val  Val Lys Phe Val Gly  Thr Ala Val
    1220                1225                1230

Asn Phe  Glu Asp Asn Leu Arg  Leu Glu His Phe Arg  Asp Thr His
    1235                1240                1245

Lys Asn  Lys Pro Leu Ile Ala  Val Asn Met Thr Ser  Lys Gly Ser
    1250                1255                1260

Ile Ser  Arg Val Leu Asn Asn  Val Leu Thr Pro Val  Thr Ser Asp
    1265                1270                1275

Leu Leu  Pro Asn Ser Ala Ala  Pro Gly Gln Leu Thr  Val Ala Gln
    1280                1285                1290

Ile Asn  Lys Met Tyr Thr Ser  Met Gly Gly Ile Glu  Pro Lys Glu
    1295                1300                1305

Leu Phe  Val Val Gly Lys Pro  Ile Gly His Ser Arg  Ser Pro Ile
    1310                1315                1320

Leu His  Asn Thr Gly Tyr Glu  Ile Leu Gly Leu Pro  His Lys Phe
    1325                1330                1335

Asp Lys  Phe Glu Thr Glu Ser  Ala Gln Leu Val Lys  Glu Lys Leu
    1340                1345                1350

Leu Asp  Gly Asn Lys Asn Phe  Gly Gly Ala Ala Val  Thr Ile Pro
    1355                1360                1365

Leu Leu  Leu Asp Ile Met Gln  Tyr Met Asp Glu Leu  Thr Asp Ala
    1370                1375                1380

Ala Lys  Val Ile Gly Ala Val  Asn Thr Val Ile Pro  Leu Gly Asn
    1385                1390                1395

Lys Lys  Phe Lys Gly Asp Asn  Thr Asp Trp Leu Gly  Ile Arg Asn
    1400                1405                1410

Ala Leu  Ile Asn Asn Gly Val  Pro Glu Tyr Val Gly  His Thr Ala
    1415                1420                1425

Gly Leu  Val Ile Gly Ala Gly  Gly Thr Ser Arg Ala  Ala Leu Tyr
    1430                1435                1440

Ala Leu  His Ser Leu Gly Cys  Lys Lys Ile Phe Ile  Ile Asn Arg
    1445                1450                1455

Thr Thr  Ser Lys Leu Lys Pro  Leu Ile Glu Ser Leu  Pro Ser Glu
    1460                1465                1470

Phe Asn  Ile Ile Gly Ile Glu  Ser Thr Lys Ser Ile  Glu Glu Ile
    1475                1480                1485

Lys Glu  His Val Gly Val Ala  Val Ser Cys Val Pro  Ala Asp Lys
    1490                1495                1500

Pro Leu  Asp Asp Glu Leu Leu  Ser Lys Leu Glu Arg  Phe Leu Val
    1505                1510                1515
```

```
Lys Gly  Ala His Ala Ala Phe  Val Pro Thr Leu Leu  Glu Ala Ala
    1520                 1525                 1530

Tyr Lys  Pro Ser Val Thr Pro  Val Met Thr Ile Ser  Gln Asp Lys
    1535                 1540                 1545

Tyr Gln  Trp His Val Val Pro  Gly Ser Gln Met Leu  Val His Gln
    1550                 1555                 1560

Gly Val  Ala Gln Phe Glu Lys  Trp Thr Gly Phe Lys  Gly Pro Phe
    1565                 1570                 1575

Lys Ala  Ile Phe Asp Ala Val  Thr Lys Glu
    1580                 1585
```

<210> SEQ ID NO 23
<211> LENGTH: 4767
<212> TYPE: DNA
<213> ORGANISM: Artificial sequence
<220> FEATURE:
<223> OTHER INFORMATION: Synthetic nucleic acid

<400> SEQUENCE: 23

```
atggtgcagt tagccaaagt cccaattcta ggaaatgata ttatccacgt tgggtataac     60

attcatgacc atttggttga aaccataatt aaacattgtc cttcttcgac atacgttatt    120

tgcaatgata cgaacttgag taaagttcca tactaccagc aattagtcct ggaattcaag    180

gcttctttgc cagaaggctc tcgtttactt acttatgttg ttaaaccagg tgagacaagt    240

aaaagtagag aaaccaaagc gcagctagaa gattatcttt tagtggaagg atgtactcgt    300

gatacggtta tggtagcgat cggtggtggt gttattggtg acatgattgg gttcgttgca    360

tctacattta tgagaggtgt tcgtgttgtc caagtaccaa catccttatt ggcaatggtc    420

gattcctcca ttggtggtaa aactgctatt gacactcctc taggtaaaaa ctttattggt    480

gcattttggc aaccaaaatt tgtccttgta gatattaaat ggctagaaac gttagccaag    540

agagagttta tcaatgggat ggcagaagtt atcaagactg cttgtatttg gaacgctgac    600

gaatttacta gattagaatc aaacgcttcg ttgttcttaa atgttgttaa tggggcaaaa    660

aatgtcaagg ttaccaatca attgacaaac gagattgacg agatatcgaa tacagatatt    720

gaagctatgt tggatcatac atataagtta gttcttgaga gtattaaggt caaagcggaa    780

gttgtctctt cggatgaacg tgaatccagt ctaagaaacc ttttgaactt cggacattct    840

attggtcatg cttatgaagc tatactaacc ccacaagcat tacatggtga atgtgtgtcc    900

attggtatgg ttaaagaggc ggaattatcc cgttatttcg gtattctctc ccctacccaa    960

gttgcacgtc tatccaagat tttggttgcc tacgggttgc ctgtttcgcc tgatgagaaa   1020

tggtttaaag agctaacctt acataagaaa acaccattgg atatcttatt gaagaaaatg   1080

agtattgaca agaaaaacga gggttccaaa aagaaggtgg tcattttaga aagtattggt   1140

aagtgctatg gtgactccgc tcaatttgtt agcgatgaag acctgagatt tattctaaca   1200

gatgaaaccc tcgtttaccc cttcaaggac atccctgctg atcaacagaa agttgttatc   1260

ccccctggtt ctaagtccat ctccaatcgt gctttaattc ttgctgccct cggtgaaggt   1320

caatgtaaaa tcaagaactt attacattct gatgatacta aacatatgtt aaccgctgtt   1380

catgaattga aaggtgctac gatatcatgg gaagataatg gtgagacggt agtggtggaa   1440

ggacatggtg gttccacatt gtcagcttgt gctgacccct tatatctagg taatgcaggt   1500

actgcatcta gatttttgac ttccttggct gccttggtca attctacttc aagccaaaag   1560

tatatcgttt taactggtaa cgcaagaatg caacaaagac caattgctcc tttggtcgat   1620
```

-continued

```
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
gagctgtttg agcaacagca taacaatcaa agtgttaaac aatttgttgt ggagaacggt   2820
tgggagaagt tccgtgagga agaaacaaga attttcaagg aagttattca aaattacggc   2880
gatgatggat atgttttctc aacaggtggc ggtattgttg aaagcgctga gtctagaaaa   2940
gccttaaaag attttgcctc atcaggtgga tacgttttac acttacatag ggatattgag   3000
gagacaattg tctttttaca aagtgatcct tcaagacctg cctatgtgga agaaattcgt   3060
gaagtttgga acagaaggga ggggtggtat aaagaatgct caaatttctc tttctttgct   3120
cctcattgct ccgcagaagc tgagttccaa gctctaagaa gatcgtttag taagtacatt   3180
gcaaccatta caggtgtcag agaaatagaa attccaagcg gaagatctgc ctttgtgtgt   3240
ttaacctttg atgacttaac tgaacaaact gagaatttga ctccaatctg ttatggttgt   3300
gaggctgtag aggtcagagt agaccatttg gctaattact ctgctgattt cgtgagtaaa   3360
cagttatcta tattgcgtaa agccactgac agtattccta tcatttttac tgtgcgaacc   3420
atgaagcaag gtggcaactt tcctgatgaa gagttcaaaa ccttgagaga gctatacgat   3480
attgccttga agaatggtgt tgaattcctt gacttagaac taactttacc tactgatatc   3540
caatatgagg ttattaacaa aaggggcaac accaagatca ttggttccca tcatgacttc   3600
caaggattat actcctggga cgacgctgaa tgggaaaaca gattcaatca agcgttaact   3660
cttgatgtgg atgttgtaaa atttgtgggt acggctgtta atttcgaaga taatttgaga   3720
ctggaacact ttagggatac acacaagaat aagcctttaa ttgcagttaa tatgacttct   3780
aaaggtagca tttctcgtgt tttgaataat gttttaacac ctgtgacatc agatttattg   3840
cctaactccg ctgcccctgg ccaattgaca gtagcacaaa ttaacaagat gtatacatct   3900
atgggaggta tcgagcctaa ggaactgttt gttgttggaa agccaattgg ccactctaga   3960
```

```
tcgccaattt tacataacac tggctatgaa attttaggtt tacctcacaa gttcgataaa    4020

tttgaaactg aatccgcaca attggtgaaa gaaaaacttt tggacggaaa caagaacttt    4080

ggcggtgctg cagtcacaat tcctctgaaa ttagatataa tgcagtacat ggatgaattg    4140

actgatgctg ctaaagttat tggtgctgta aacacagtta taccattggg taacaagaag    4200

tttaagggtg ataataccga ctggttaggt atccgtaatg ccttaattaa caatggcgtt    4260

cccgaatatg ttggtcatac cgctggtttg gttatcggtg caggtggcac ttctagagcc    4320

ccactttacg ccttgcacag tttaggttgc aaaaagatct tcataatcaa caggacaact    4380

tcgaaattga agccattaat agagtcactt ccatctgaat tcaacattat tggaatagag    4440

tccactaaat ctatagaaga gattaaggaa cacgttggcg ttgctgtcag ctgtgtacca    4500

gccgacaaac cattagatga cgaactttta agtaagctgg agagattcct tgtgaaaggt    4560

gcccatgctg cttttgtacc aaccttattg gaagccgcat acaaaccaag cgttactccc    4620

gttatgacaa tttcacaaga caaatatcaa tggcacgttg tccctggatc acaaatgtta    4680

gtacaccaag gtgtagctca gtttgaaaag tggacaggat tcaagggccc tttcaaggcc    4740

atttttgatg ccgttacgaa agagtag                                        4767

<210> SEQ ID NO 24
<211> LENGTH: 1588
<212> TYPE: PRT
<213> ORGANISM: Artificial sequence
<220> FEATURE:
<223> OTHER INFORMATION: Synthetic polypeptide

<400> SEQUENCE: 24

Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220
```

-continued

```
Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640
```

-continued

```
Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                 1005

Asp Pro  Ser Arg Pro Ala Tyr  Val Glu Glu Ile Arg  Glu Val Trp
    1010                 1015                 1020

Asn Arg  Arg Glu Gly Trp Tyr  Lys Glu Cys Ser Asn  Phe Ser Phe
    1025                 1030                 1035

Phe Ala  Pro His Cys Ser Ala  Glu Ala Glu Phe Gln  Ala Leu Arg
    1040                 1045                 1050

Arg Ser  Phe Ser Lys Tyr Ile  Ala Thr Ile Thr Gly  Val Arg Glu
```

```
    1055                1060                1065

Ile Glu  Ile Pro Ser Gly Arg  Ser Ala Phe Val Cys  Leu Thr Phe
    1070                1075                1080

Asp Asp  Leu Thr Glu Gln Thr  Glu Asn Leu Thr Pro  Ile Cys Tyr
    1085                1090                1095

Gly Cys  Glu Ala Val Glu Val  Arg Val Asp His Leu  Ala Asn Tyr
    1100                1105                1110

Ser Ala  Asp Phe Val Ser Lys  Gln Leu Ser Ile Leu  Arg Lys Ala
    1115                1120                1125

Thr Asp  Ser Ile Pro Ile Ile  Phe Thr Val Arg Thr  Met Lys Gln
    1130                1135                1140

Gly Gly  Asn Phe Pro Asp Glu  Glu Phe Lys Thr Leu  Arg Glu Leu
    1145                1150                1155

Tyr Asp  Ile Ala Leu Lys Asn  Gly Val Glu Phe Leu  Asp Leu Glu
    1160                1165                1170

Leu Thr  Leu Pro Thr Asp Ile  Gln Tyr Glu Val Ile  Asn Lys Arg
    1175                1180                1185

Gly Asn  Thr Lys Ile Ile Gly  Ser His His Asp Phe  Gln Gly Leu
    1190                1195                1200

Tyr Ser  Trp Asp Asp Ala Glu  Trp Glu Asn Arg Phe  Asn Gln Ala
    1205                1210                1215

Leu Thr  Leu Asp Val Asp Val  Val Lys Phe Val Gly  Thr Ala Val
    1220                1225                1230

Asn Phe  Glu Asp Asn Leu Arg  Leu Glu His Phe Arg  Asp Thr His
    1235                1240                1245

Lys Asn  Lys Pro Leu Ile Ala  Val Asn Met Thr Ser  Lys Gly Ser
    1250                1255                1260

Ile Ser  Arg Val Leu Asn Asn  Val Leu Thr Pro Val  Thr Ser Asp
    1265                1270                1275

Leu Leu  Pro Asn Ser Ala Ala  Pro Gly Gln Leu Thr  Val Ala Gln
    1280                1285                1290

Ile Asn  Lys Met Tyr Thr Ser  Met Gly Gly Ile Glu  Pro Lys Glu
    1295                1300                1305

Leu Phe  Val Val Gly Lys Pro  Ile Gly His Ser Arg  Ser Pro Ile
    1310                1315                1320

Leu His  Asn Thr Gly Tyr Glu  Ile Leu Gly Leu Pro  His Lys Phe
    1325                1330                1335

Asp Lys  Phe Glu Thr Glu Ser  Ala Gln Leu Val Lys  Glu Lys Leu
    1340                1345                1350

Leu Asp  Gly Asn Lys Asn Phe  Gly Gly Ala Ala Val  Thr Ile Pro
    1355                1360                1365

Leu Lys  Leu Asp Ile Met Gln  Tyr Met Asp Glu Leu  Thr Asp Ala
    1370                1375                1380

Ala Lys  Val Ile Gly Ala Val  Asn Thr Val Ile Pro  Leu Gly Asn
    1385                1390                1395

Lys Lys  Phe Lys Gly Asp Asn  Thr Asp Trp Leu Gly  Ile Arg Asn
    1400                1405                1410

Ala Leu  Ile Asn Asn Gly Val  Pro Glu Tyr Val Gly  His Thr Ala
    1415                1420                1425

Gly Leu  Val Ile Gly Ala Gly  Gly Thr Ser Arg Ala  Pro Leu Tyr
    1430                1435                1440

Ala Leu  His Ser Leu Gly Cys  Lys Lys Ile Phe Ile  Ile Asn Arg
    1445                1450                1455
```

```
Thr Thr  Ser Lys Leu Lys Pro  Leu Ile Glu Ser Leu  Pro Ser Glu
    1460                 1465                 1470

Phe Asn  Ile Ile Gly Ile Glu  Ser Thr Lys Ser Ile  Glu Glu Ile
    1475                 1480                 1485

Lys Glu  His Val Gly Val Ala  Val Ser Cys Val Pro  Ala Asp Lys
    1490                 1495                 1500

Pro Leu  Asp Asp Glu Leu Leu  Ser Lys Leu Glu Arg  Phe Leu Val
    1505                 1510                 1515

Lys Gly  Ala His Ala Ala Phe  Val Pro Thr Leu Leu  Glu Ala Ala
    1520                 1525                 1530

Tyr Lys  Pro Ser Val Thr Pro  Val Met Thr Ile Ser  Gln Asp Lys
    1535                 1540                 1545

Tyr Gln  Trp His Val Val Pro  Gly Ser Gln Met Leu  Val His Gln
    1550                 1555                 1560

Gly Val  Ala Gln Phe Glu Lys  Trp Thr Gly Phe Lys  Gly Pro Phe
    1565                 1570                 1575

Lys Ala  Ile Phe Asp Ala Val  Thr Lys Glu
    1580                 1585
```

<210> SEQ ID NO 25
<211> LENGTH: 5064
<212> TYPE: DNA
<213> ORGANISM: Artificial sequence
<220> FEATURE:
<223> OTHER INFORMATION: Synthetic nucleic acid

<400> SEQUENCE: 25

```
atggtgcagt tagccaaagt cccaattcta ggaaatgata ttatccacgt tgggtataac      60

attcatgacc atttggttga aaccataatt aaacattgtc cttcttcgac atacgttatt     120

tgcaatgata cgaacttgag taaagttcca tactaccagc aattagtcct ggaattcaag     180

gcttctttgc cagaaggctc tcgtttactt acttatgttg ttaaaccagg tgagacaagt     240

aaaagtagag aaaccaaagc gcagctagaa gattatcttt tagtggaagg atgtactcgt     300

gatacggtta tggtagcgat cggtggtggt gttattggtg acatgattgg gttcgttgca     360

tctacattta tgagaggtgt tcgtgttgtc caagtaccaa catccttatt ggcaatggtc     420

gattcctcca ttggtggtaa aactgctatt gacactcctc taggtaaaaa ctttattggt     480

gcattttggc aaccaaaatt tgtccttgta gatattaaat ggctagaaac gttagccaag     540

agagagttta tcaatgggat ggcagaagtt atcaagactg cttgtatttg gaacgctgac     600

gaatttacta gattagaatc aaacgcttcg ttgttcttaa atgttgttaa tggggcaaaa     660

aatgtcaagg ttaccaatca attgacaaac gagattgacg agatatcgaa tacagatatt     720

gaagctatgt tggatcatac atataagtta gttcttgaga gtattaaggt caaagcggaa     780

gttgtctctt cggatgaacg tgaatccagt ctaagaaacc ttttgaactt cggacattct     840

attggtcatg cttatgaagc tatactaacc ccacaagcat tacatggtga atgtgtgtcc     900

attggtatgg ttaaagaggc ggaattatcc cgttatttcg gtattctctc ccctacccaa     960

gttgcacgtc tatccaagat tttggttgcc tacgggttgc ctgtttcgcc tgatgagaaa    1020

tggtttaaag agctaacctt acataagaaa acaccattgg atatcttatt gaagaaaatg    1080

agtattgaca agaaaaacga gggttccaaa aagaaggtgg tcattttaga aagtattggt    1140

aagtgctatg gtgactccgc tcaatttgtt agcgatgaag acctgagatt tattctaaca    1200

gatgaaaccc tcgtttaccc cttcaaggac atccctgctg atcaacagaa agttgttatc    1260
```

-continued

```
ccccctggtt ctaagtccat ctccaatcgt gctttaattc ttgctgccct cggtgaaggt   1320
caatgtaaaa tcaagaactt attacattct gatgatacta aacatatgtt aaccgctgtt   1380
catgaattga aaggtgctac gatatcatgg gaagataatg gtgagacggt agtggtggaa   1440
ggacatggtg gttccacatt gtcagcttgt gctgacccct tatatctagg taatgcaggt   1500
actgcatcta gatttttgac ttccttggct gccttggtca attctacttc aagccaaaag   1560
tatatcgttt taactggtaa cgcaagaatg caacaaagac caattgctcc tttggtcgat   1620
tctttgcgtg ctaatggtac taaaattgag tacttgaata atgaaggttc cctgccaatc   1680
aaagtttata ctgattcggt attcaaaggt ggtagaattg aattagctgc tacagtttct   1740
tctcagtacg tatcctctat cttgatgtgt gccccatacg ctgaagaacc tgtaactttg   1800
gctcttgttg gtggtaagcc aatctctaaa ttgtacgtcg atatgacaat aaaaatgatg   1860
gaaaaattcg gtatcaatgt tgaaacttct actacagaac cttacactta ttatattcca   1920
aagggacatt atattaaccc atcagaatac gtcattgaaa gtgatgcctc aagtgctaca   1980
tacccattgg ccttcgccgc aatgactggt actaccgtaa cggttccaaa cattggtttt   2040
gagtcgttac aaggtgatgc cagatttgca agagatgtct tgaaacctat gggttgtaaa   2100
ataactcaaa cggcaacttc aactactgtt tcgggtcctc ctgtaggtac tttaaagcca   2160
ttaaaacatg ttgatatgga gccaatgact gatgcgttct taactgcatg tgttgttgcc   2220
gctatttcgc acgacagtga tccaaattct gcaaatacaa ccaccattga aggtattgca   2280
aaccagcgtg tcaaagagtg taacagaatt ttggccatgg ctacagagct cgccaaattt   2340
ggcgtcaaaa ctacagaatt accagatggt attcaagtcc atggtttaaa ctcgataaaa   2400
gatttgaagg ttccttccga ctcttctgga cctgtcggtg tatgcacata tgatgatcat   2460
cgtgtggcca tgagtttctc gcttcttgca ggaatggtaa attctcaaaa tgaacgtgac   2520
gaagttgcta atcctgtaag aatacttgaa agacattgta ctggtaaaac ctggcctggc   2580
tggtgggatg tgttacattc cgaactaggt gccaaattag atggtgcaga acctttagag   2640
tgcacatcca aaaagaactc aaagaaaagc gttgtcatta ttggcatgag agcagctggc   2700
aaaactacta taagtaaatg gtgcgcatcc gctctgggtt acaaattagt tgacctagac   2760
gagctgtttg agcaacagca taacaatcaa agtgttaaac aatttgttgt ggagaacggt   2820
tgggagaagt tccgtgagga agaaacaaga attttcaagg aagttattca aaattacggc   2880
gatgatggat atgttttctc aacaggtggc ggtattgttg aaagcgctga gtctagaaaa   2940
gccttaaaag attttgcctc atcaggtgga tacgttttac acttacatag ggatattgag   3000
gagacaattg tctttttaca aagtgatcct tcaagacctg cctatgtgga agaaattcgt   3060
gaagtttgga acagaaggga ggggtggtat aaagaatgct caaatttctc tttctttgct   3120
cctcattgct ccgcagaagc tgagttccaa gctctaagaa gatcgtttag taagtacatt   3180
gcaaccatta caggtgtcag agaaatagaa attccaagcg gaagatctgc ctttgtgtgt   3240
ttaacctttg atgacttaac tgaacaaact gagaatttga ctccaatctg ttatggttgt   3300
gaggctgtag aggtcagagt agaccatttg gctaattact ctgctgattt cgtgagtaaa   3360
cagttatcta tattgcgtaa agccactgac agtattccta tcatttttac tgtgcgaacc   3420
atgaagcaag gtggcaactt tcctgatgaa gagttcaaaa ccttgagaga gctatacgat   3480
attgccttga agaatggtgt tgaattcctt gacttagaac taactttacc tactgatatc   3540
caatatgagg ttattaacaa aaggggcaac accaagatca ttggttccca tcatgacttc   3600
```

```
caaggattat actcctggga cgacgctgaa tgggaaaaca gattcaatca agcgttaact   3660

cttgatgtgg atgttgtaaa atttgtgggt acggctgtta atttcgaaga taatttgaga   3720

ctggaacact ttagggatac acacaagaat aagcctttaa ttgcagttaa tatgacttct   3780

aaaggtagca tttctcgtgt tttgaataat gttttaacac ctgtgacatc agatttattg   3840

cctaactccg ctgcccctgg ccaattgaca gtagcacaaa ttaacaagat gtatacatct   3900

atgggaggta tcgagcctaa ggaactgttt gttgttggaa agccaattgg ccccgggaaa   3960

atgccttcca aactcgccat cacttccatg tcacttggcc ggtgttatgc cggccactcc   4020

ttcaccacta agctcgatat ggcccggaaa tatggctatc aaggcctaga gctcttccac   4080

gaggacttgg ctgatgtagc ctatcgtctc tccggagaga ccccttcccc atgtggcccg   4140

tccccagcag cccagctctc ggctgcccgt caaatcctcc gcatgtgcca agtcagaaac   4200

attgaaatcg tctgcctcca gcccttcagc cagtacgacg gcctactcga ccgcgaggag   4260

cacgagcgcc gtctggagca gctcgagttc tggatcgagc tcgcccacga gcttgacaca   4320

gacattatcc aaatccccgc caactttctc cccgccgagg aagtaactga ggacatttcg   4380

ctcatcgtct cggaccttca agaagtggcc gacatgggcc tgcaggccaa cccacccatc   4440

cgctttgtct acgaggctct gtgctggagc actcgtgtcg acacttggga gcgtagctgg   4500

gaggtggtgc agagggtgaa caggcccaac tttggcgtgt gcctggacac tttcaacatt   4560

gcggggcggg tatatgctga tccgacggtt gcctctggcc gcacccccaa cgcggaggaa   4620

gcgatacgga agtcgattgc gcgtctcgtt gaaagggtcg atgtcagcaa ggtcttttat   4680

gtgcaggttg tggacgctga gaagttgaag aagccgctgg tgccgggtca tcggttttat   4740

gacccggagc agccggcgag gatgagctgg tcaaggaact gcaggttatt ctacggggag   4800

aaggacagag ggcgtattt gcccgtcaag gagattgcct gggccttctt caacgggctc   4860

ggattcgagg gttgggtcag tctggagctc ttcaacagaa gaatgtcgga cacaggcttt   4920

ggggtgcccg aggagctggc caggagaggg gccgtgtcgt gggcaaagct ggtgagggac   4980

atgaagatca ctgttgattc accaacacaa caacaagcca cacagcagcc catcaggatg   5040

ctgtcgctgt cagcggcttt gtaa                                          5064
```

<210> SEQ ID NO 26
<211> LENGTH: 1687
<212> TYPE: PRT
<213> ORGANISM: Artificial sequence
<220> FEATURE:
<223> OTHER INFORMATION: Synthetic polypeptide

<400> SEQUENCE: 26

```
Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45

Val Pro Tyr Tyr Gln Gln Leu Val Leu Glu Phe Lys Ala Ser Leu Pro
    50                  55                  60

Glu Gly Ser Arg Leu Leu Thr Tyr Val Val Lys Pro Gly Glu Thr Ser
65                  70                  75                  80

Lys Ser Arg Glu Thr Lys Ala Gln Leu Glu Asp Tyr Leu Leu Val Glu
                85                  90                  95

Gly Cys Thr Arg Asp Thr Val Met Val Ala Ile Gly Gly Gly Val Ile
```

-continued

```
            100                 105                 110

Gly Asp Met Ile Gly Phe Val Ala Ser Thr Phe Met Arg Gly Val Arg
        115                 120                 125

Val Val Gln Val Pro Thr Ser Leu Leu Ala Met Val Asp Ser Ser Ile
    130                 135                 140

Gly Gly Lys Thr Ala Ile Asp Thr Pro Leu Gly Lys Asn Phe Ile Gly
145                 150                 155                 160

Ala Phe Trp Gln Pro Lys Phe Val Leu Val Asp Ile Lys Trp Leu Glu
                165                 170                 175

Thr Leu Ala Lys Arg Glu Phe Ile Asn Gly Met Ala Glu Val Ile Lys
            180                 185                 190

Thr Ala Cys Ile Trp Asn Ala Asp Glu Phe Thr Arg Leu Glu Ser Asn
        195                 200                 205

Ala Ser Leu Phe Leu Asn Val Val Asn Gly Ala Lys Asn Val Lys Val
    210                 215                 220

Thr Asn Gln Leu Thr Asn Glu Ile Asp Glu Ile Ser Asn Thr Asp Ile
225                 230                 235                 240

Glu Ala Met Leu Asp His Thr Tyr Lys Leu Val Leu Glu Ser Ile Lys
                245                 250                 255

Val Lys Ala Glu Val Val Ser Ser Asp Glu Arg Glu Ser Ser Leu Arg
            260                 265                 270

Asn Leu Leu Asn Phe Gly His Ser Ile Gly His Ala Tyr Glu Ala Ile
        275                 280                 285

Leu Thr Pro Gln Ala Leu His Gly Glu Cys Val Ser Ile Gly Met Val
    290                 295                 300

Lys Glu Ala Glu Leu Ser Arg Tyr Phe Gly Ile Leu Ser Pro Thr Gln
305                 310                 315                 320

Val Ala Arg Leu Ser Lys Ile Leu Val Ala Tyr Gly Leu Pro Val Ser
                325                 330                 335

Pro Asp Glu Lys Trp Phe Lys Glu Leu Thr Leu His Lys Lys Thr Pro
            340                 345                 350

Leu Asp Ile Leu Leu Lys Lys Met Ser Ile Asp Lys Lys Asn Glu Gly
        355                 360                 365

Ser Lys Lys Lys Val Val Ile Leu Glu Ser Ile Gly Lys Cys Tyr Gly
    370                 375                 380

Asp Ser Ala Gln Phe Val Ser Asp Glu Asp Leu Arg Phe Ile Leu Thr
385                 390                 395                 400

Asp Glu Thr Leu Val Tyr Pro Phe Lys Asp Ile Pro Ala Asp Gln Gln
                405                 410                 415

Lys Val Val Ile Pro Pro Gly Ser Lys Ser Ile Ser Asn Arg Ala Leu
            420                 425                 430

Ile Leu Ala Ala Leu Gly Glu Gly Gln Cys Lys Ile Lys Asn Leu Leu
        435                 440                 445

His Ser Asp Asp Thr Lys His Met Leu Thr Ala Val His Glu Leu Lys
    450                 455                 460

Gly Ala Thr Ile Ser Trp Glu Asp Asn Gly Glu Thr Val Val Val Glu
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525
```

```
Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895

Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940
```

-continued

```
Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                 1005

Asp Pro  Ser Arg Pro Ala Tyr  Val Glu Glu Ile Arg  Glu Val Trp
    1010                 1015                 1020

Asn Arg  Arg Glu Gly Trp Tyr  Lys Glu Cys Ser Asn  Phe Ser Phe
    1025                 1030                 1035

Phe Ala  Pro His Cys Ser Ala  Glu Ala Glu Phe Gln  Ala Leu Arg
    1040                 1045                 1050

Arg Ser  Phe Ser Lys Tyr Ile  Ala Thr Ile Thr Gly  Val Arg Glu
    1055                 1060                 1065

Ile Glu  Ile Pro Ser Gly Arg  Ser Ala Phe Val Cys  Leu Thr Phe
    1070                 1075                 1080

Asp Asp  Leu Thr Glu Gln Thr  Glu Asn Leu Thr Pro  Ile Cys Tyr
    1085                 1090                 1095

Gly Cys  Glu Ala Val Glu Val  Arg Val Asp His Leu  Ala Asn Tyr
    1100                 1105                 1110

Ser Ala  Asp Phe Val Ser Lys  Gln Leu Ser Ile Leu  Arg Lys Ala
    1115                 1120                 1125

Thr Asp  Ser Ile Pro Ile Ile  Phe Thr Val Arg Thr  Met Lys Gln
    1130                 1135                 1140

Gly Gly  Asn Phe Pro Asp Glu  Glu Phe Lys Thr Leu  Arg Glu Leu
    1145                 1150                 1155

Tyr Asp  Ile Ala Leu Lys Asn  Gly Val Glu Phe Leu  Asp Leu Glu
    1160                 1165                 1170

Leu Thr  Leu Pro Thr Asp Ile  Gln Tyr Glu Val Ile  Asn Lys Arg
    1175                 1180                 1185

Gly Asn  Thr Lys Ile Ile Gly  Ser His His Asp Phe  Gln Gly Leu
    1190                 1195                 1200

Tyr Ser  Trp Asp Asp Ala Glu  Trp Glu Asn Arg Phe  Asn Gln Ala
    1205                 1210                 1215

Leu Thr  Leu Asp Val Asp Val  Val Lys Phe Val Gly  Thr Ala Val
    1220                 1225                 1230

Asn Phe  Glu Asp Asn Leu Arg  Leu Glu His Phe Arg  Asp Thr His
    1235                 1240                 1245

Lys Asn  Lys Pro Leu Ile Ala  Val Asn Met Thr Ser  Lys Gly Ser
    1250                 1255                 1260

Ile Ser  Arg Val Leu Asn Asn  Val Leu Thr Pro Val  Thr Ser Asp
    1265                 1270                 1275

Leu Leu  Pro Asn Ser Ala Ala  Pro Gly Gln Leu Thr  Val Ala Gln
    1280                 1285                 1290

Ile Asn  Lys Met Tyr Thr Ser  Met Gly Gly Ile Glu  Pro Lys Glu
    1295                 1300                 1305

Leu Phe  Val Val Gly Lys Pro  Ile Gly Pro Gly Lys  Met Pro Ser
    1310                 1315                 1320

Lys Leu  Ala Ile Thr Ser Met  Ser Leu Gly Arg Cys  Tyr Ala Gly
    1325                 1330                 1335

His Ser  Phe Thr Thr Lys Leu  Asp Met Ala Arg Lys  Tyr Gly Tyr
```

```
    1340                1345                1350

Gln Gly  Leu Glu Leu Phe His  Glu Asp Leu Ala Asp  Val Ala Tyr
    1355                1360                1365

Arg Leu  Ser Gly Glu Thr Pro  Ser Pro Cys Gly Pro  Ser Pro Ala
    1370                1375                1380

Ala Gln  Leu Ser Ala Ala Arg  Gln Ile Leu Arg Met  Cys Gln Val
    1385                1390                1395

Arg Asn  Ile Glu Ile Val Cys  Leu Gln Pro Phe Ser  Gln Tyr Asp
    1400                1405                1410

Gly Leu  Leu Asp Arg Glu Glu  His Glu Arg Arg Leu  Glu Gln Leu
    1415                1420                1425

Glu Phe  Trp Ile Glu Leu Ala  His Glu Leu Asp Thr  Asp Ile Ile
    1430                1435                1440

Gln Ile  Pro Ala Asn Phe Leu  Pro Ala Glu Glu Val  Thr Glu Asp
    1445                1450                1455

Ile Ser  Leu Ile Val Ser Asp  Leu Gln Glu Val Ala  Asp Met Gly
    1460                1465                1470

Leu Gln  Ala Asn Pro Pro Ile  Arg Phe Val Tyr Glu  Ala Leu Cys
    1475                1480                1485

Trp Ser  Thr Arg Val Asp Thr  Trp Glu Arg Ser Trp  Glu Val Val
    1490                1495                1500

Gln Arg  Val Asn Arg Pro Asn  Phe Gly Val Cys Leu  Asp Thr Phe
    1505                1510                1515

Asn Ile  Ala Gly Arg Val Tyr  Ala Asp Pro Thr Val  Ala Ser Gly
    1520                1525                1530

Arg Thr  Pro Asn Ala Glu Glu  Ala Ile Arg Lys Ser  Ile Ala Arg
    1535                1540                1545

Leu Val  Glu Arg Val Asp Val  Ser Lys Val Phe Tyr  Val Gln Val
    1550                1555                1560

Val Asp  Ala Glu Lys Leu Lys  Lys Pro Leu Val Pro  Gly His Arg
    1565                1570                1575

Phe Tyr  Asp Pro Glu Gln Pro  Ala Arg Met Ser Trp  Ser Arg Asn
    1580                1585                1590

Cys Arg  Leu Phe Tyr Gly Glu  Lys Asp Arg Gly Ala  Tyr Leu Pro
    1595                1600                1605

Val Lys  Glu Ile Ala Trp Ala  Phe Phe Asn Gly Leu  Gly Phe Glu
    1610                1615                1620

Gly Trp  Val Ser Leu Glu Leu  Phe Asn Arg Arg Met  Ser Asp Thr
    1625                1630                1635

Gly Phe  Gly Val Pro Glu Glu  Leu Ala Arg Arg Gly  Ala Val Ser
    1640                1645                1650

Trp Ala  Lys Leu Val Arg Asp  Met Lys Ile Thr Val  Asp Ser Pro
    1655                1660                1665

Thr Gln  Gln Gln Ala Thr Gln  Gln Pro Ile Arg Met  Leu Ser Leu
    1670                1675                1680

Ser Ala  Ala Leu
    1685
```

<210> SEQ ID NO 27
<211> LENGTH: 221
<212> TYPE: PRT
<213> ORGANISM: Homo sapiens

<400> SEQUENCE: 27

-continued

```
Met Gly Asp Thr Lys Glu Gln Arg Ile Leu Asn His Val Leu Gln His
1               5                   10                  15

Ala Glu Pro Gly Asn Ala Gln Ser Val Leu Glu Ala Ile Asp Thr Tyr
            20                  25                  30

Cys Glu Gln Lys Glu Trp Ala Met Asn Val Gly Asp Lys Lys Gly Lys
        35                  40                  45

Ile Val Asp Ala Val Ile Gln Glu His Gln Pro Ser Val Leu Leu Glu
    50                  55                  60

Leu Gly Ala Tyr Cys Gly Tyr Ser Ala Val Arg Met Ala Arg Leu Leu
65                  70                  75                  80

Ser Pro Gly Ala Arg Leu Ile Thr Ile Glu Ile Asn Pro Asp Cys Ala
                85                  90                  95

Ala Ile Thr Gln Arg Met Val Asp Phe Ala Gly Val Lys Asp Lys Val
            100                 105                 110

Thr Leu Val Val Gly Ala Ser Gln Asp Ile Ile Pro Gln Leu Lys Lys
        115                 120                 125

Lys Tyr Asp Val Asp Thr Leu Asp Met Val Phe Leu Asp His Trp Lys
    130                 135                 140

Asp Arg Tyr Leu Pro Asp Thr Leu Leu Leu Glu Glu Cys Gly Leu Leu
145                 150                 155                 160

Arg Lys Gly Thr Val Leu Leu Ala Asp Asn Val Ile Cys Pro Gly Ala
                165                 170                 175

Pro Asp Phe Leu Ala His Val Arg Gly Ser Ser Cys Phe Glu Cys Thr
            180                 185                 190

His Tyr Gln Ser Phe Leu Glu Tyr Arg Glu Val Val Asp Gly Leu Glu
        195                 200                 205

Lys Ala Ile Tyr Lys Gly Pro Gly Ser Glu Ala Gly Pro
    210                 215                 220
```

<210> SEQ ID NO 28
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 28
cgtagcatgc agtctagaaa aatgggtgac actaaggagc 40

<210> SEQ ID NO 29
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 29
gacgacgtta gtgacagaat tcttatggac cagcttcaga acctg 45

<210> SEQ ID NO 30
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 30
cgtagcatgc agtctagaaa aatgg 25

-continued

<210> SEQ ID NO 31
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 31
gacgacgtta gtgacagaat tc 22

<210> SEQ ID NO 32
<211> LENGTH: 45
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (30)..(30)
<223> OTHER INFORMATION: n is a, c, g, or t

<400> SEQUENCE: 32
ctattgacac ttattgtgag caaaaggagn rkgctatgaa cgttg 45

<210> SEQ ID NO 33
<211> LENGTH: 45
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (30)..(30)
<223> OTHER INFORMATION: n is a, c, g, or t

<400> SEQUENCE: 33
ctattgacac ttattgtgag caaaaggagn ykgctatgaa cgttg 45

<210> SEQ ID NO 34
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 34
ctccttttgc tcacaataag tgtcaatag 29

<210> SEQ ID NO 35
<211> LENGTH: 45
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: n is a, c, g, or t

<400> SEQUENCE: 35
gacacttatt gtgagcaaaa ggagtgggct nrkaacgttg gtgac 45

<210> SEQ ID NO 36
<211> LENGTH: 43
<212> TYPE: DNA
<213> ORGANISM: Artificial sequence
<220> FEATURE:
<223> OTHER INFORMATION: Synthetic oligonucleotide
<220> FEATURE:

<221> NAME/KEY: misc_feature
<222> LOCATION: (29)..(29)
<223> OTHER INFORMATION: n is a, c, g, or t

<400> SEQUENCE: 36
cacttattgt gagcaaaagg agtgggctny kaacgttggt gac 43

<210> SEQ ID NO 37
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 37
ctccttttgc tcacaataag tgtc 24

<210> SEQ ID NO 38
<211> LENGTH: 46
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (27)..(27)
<223> OTHER INFORMATION: n is a, c, g, or t

<400> SEQUENCE: 38
ctttggacat ggttttcttg gaccatnrka aggacagata tttgcc 46

<210> SEQ ID NO 39
<211> LENGTH: 46
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (27)..(27)
<223> OTHER INFORMATION: n is a, c, g, or t

<400> SEQUENCE: 39
ctttggacat ggttttcttg gaccatnyka aggacagata tttgcc 46

<210> SEQ ID NO 40
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 40
atggtccaag aaaaccatgt ccaaag 26

<210> SEQ ID NO 41
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (30)..(30)
<223> OTHER INFORMATION: n is a, c, g, or t

<400> SEQUENCE: 41
gtactgtttt gttagctgac aacgttattn rkccaggtgc tccagacttc ttg 53

<210> SEQ ID NO 42
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (30)..(30)
<223> OTHER INFORMATION: n is a, c, g, or t

<400> SEQUENCE: 42
gtactgtttt gttagctgac aacgttattn ykccaggtgc tccagacttc ttg 53

<210> SEQ ID NO 43
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 43
aataacgttg tcagctaaca aaacagtac 29

<210> SEQ ID NO 44
<211> LENGTH: 47
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (30)..(30)
<223> OTHER INFORMATION: n is a, c, g, or t

<400> SEQUENCE: 44
ctgttttgtt agctgacaac gttatttgtn rkggtgctcc agacttc 47

<210> SEQ ID NO 45
<211> LENGTH: 47
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (30)..(30)
<223> OTHER INFORMATION: n is a, c, g, or t

<400> SEQUENCE: 45
ctgttttgtt agctgacaac gttatttgtn ykggtgctcc agacttc 47

<210> SEQ ID NO 46
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 46
acaaataacg ttgtcagcta acaaaacag 29

<210> SEQ ID NO 47
<211> LENGTH: 103
<212> TYPE: DNA
<213> ORGANISM: Artificial sequence
<220> FEATURE:

<223> OTHER INFORMATION: Synthetic oligonucleotide
<220> FEATURE:
<221> NAME/KEY: misc_feature
<222> LOCATION: (86)..(86)
<223> OTHER INFORMATION: n is a, c, g, or t

<400> SEQUENCE: 47
atttagaatt cttatggacc agcttcagaa cctggaccct tatatatagc cttctccaaa 60
ccgtcaacaa cctctctata ttcmyngaaa gattgataat gag 103

<210> SEQ ID NO 48
<211> LENGTH: 102
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (85)..(85)
<223> OTHER INFORMATION: n is a, c, g, or t

<400> SEQUENCE: 48
atttagaatt ctatggacca gcttcagaac ctggaccctt atatatagcc ttctccaaac 60
cgtcaacaac ctctctatat tcmrngaaag attgataatg ag 102

<210> SEQ ID NO 49
<211> LENGTH: 101
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (83)..(83)
<223> OTHER INFORMATION: n is a, c, g, or t

<400> SEQUENCE: 49
atttagaatt cttatggacc agcttcagaa cctggaccct tatatatagc cttctccaaa 60
ccgtcaacaa cctctctata myncaagaaa gattgataat g 101

<210> SEQ ID NO 50
<211> LENGTH: 101
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (83)..(83)
<223> OTHER INFORMATION: n is a, c, g, or t

<400> SEQUENCE: 50
atttagaatt cttatggacc agcttcagaa cctggaccct tatatatagc cttctccaaa 60
ccgtcaacaa cctctctata mrncaagaaa gattgataat g 101

<210> SEQ ID NO 51
<211> LENGTH: 95
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (77)..(77)
<223> OTHER INFORMATION: n is a, c, g, or t

<400> SEQUENCE: 51

```
atttagaatt cttatggacc agcttcagaa cctggaccct tatatatagc cttctccaaa     60

ccgtcaacaa cctcmynata ttccaagaaa gattg                                95


<210> SEQ ID NO 52
<211> LENGTH: 95
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (77)..(77)
<223> OTHER INFORMATION: n is a, c, g, or t

<400> SEQUENCE: 52

atttagaatt cttatggacc agcttcagaa cctggaccct tatatatagc cttctccaaa     60

ccgtcaacaa cctcmrnata ttccaagaaa gattg                                95


<210> SEQ ID NO 53
<211> LENGTH: 363
<212> TYPE: PRT
<213> ORGANISM: Arabidopsis thaliana

<400> SEQUENCE: 53

Met Gly Ser Thr Ala Glu Thr Gln Leu Thr Pro Val Gln Val Thr Asp
1               5                   10                  15

Asp Glu Ala Ala Leu Phe Ala Met Gln Leu Ala Ser Ala Ser Val Leu
            20                  25                  30

Pro Met Ala Leu Lys Ser Ala Leu Glu Leu Asp Leu Leu Glu Ile Met
        35                  40                  45

Ala Lys Asn Gly Ser Pro Met Ser Pro Thr Glu Ile Ala Ser Lys Leu
    50                  55                  60

Pro Thr Lys Asn Pro Glu Ala Pro Val Met Leu Asp Arg Ile Leu Arg
65                  70                  75                  80

Leu Leu Thr Ser Tyr Ser Val Leu Thr Cys Ser Asn Arg Lys Leu Ser
                85                  90                  95

Gly Asp Gly Val Glu Arg Ile Tyr Gly Leu Gly Pro Val Cys Lys Tyr
            100                 105                 110

Leu Thr Lys Asn Glu Asp Gly Val Ser Ile Ala Ala Leu Cys Leu Met
        115                 120                 125

Asn Gln Asp Lys Val Leu Met Glu Ser Trp Tyr His Leu Lys Asp Ala
    130                 135                 140

Ile Leu Asp Gly Gly Ile Pro Phe Asn Lys Ala Tyr Gly Met Ser Ala
145                 150                 155                 160

Phe Glu Tyr His Gly Thr Asp Pro Arg Phe Asn Lys Val Phe Asn Asn
                165                 170                 175

Gly Met Ser Asn His Ser Thr Ile Thr Met Lys Lys Ile Leu Glu Thr
            180                 185                 190

Tyr Lys Gly Phe Glu Gly Leu Thr Ser Leu Val Asp Val Gly Gly Gly
        195                 200                 205

Ile Gly Ala Thr Leu Lys Met Ile Val Ser Lys Tyr Pro Asn Leu Lys
    210                 215                 220

Gly Ile Asn Phe Asp Leu Pro His Val Ile Glu Asp Ala Pro Ser His
225                 230                 235                 240

Pro Gly Ile Glu His Val Gly Gly Asp Met Phe Val Ser Val Pro Lys
                245                 250                 255
```

```
Gly Asp Ala Ile Phe Met Lys Trp Ile Cys His Asp Trp Ser Asp Glu
            260                 265                 270

His Cys Val Lys Phe Leu Lys Asn Cys Tyr Glu Ser Leu Pro Glu Asp
        275                 280                 285

Gly Lys Val Ile Leu Ala Glu Cys Ile Leu Pro Glu Thr Pro Asp Ser
    290                 295                 300

Ser Leu Ser Thr Lys Gln Val Val His Val Asp Cys Ile Met Leu Ala
305                 310                 315                 320

His Asn Pro Gly Gly Lys Glu Arg Thr Glu Lys Glu Phe Glu Ala Leu
                325                 330                 335

Ala Lys Ala Ser Gly Phe Lys Gly Ile Lys Val Val Cys Asp Ala Phe
            340                 345                 350

Gly Val Asn Leu Ile Glu Leu Leu Lys Lys Leu
        355                 360


<210> SEQ ID NO 54
<211> LENGTH: 365
<212> TYPE: PRT
<213> ORGANISM: Fragaria x ananassa

<400> SEQUENCE: 54

Met Gly Ser Thr Gly Glu Thr Gln Met Thr Pro Thr His Val Ser Asp
1               5                   10                  15

Glu Glu Ala Asn Leu Phe Ala Met Gln Leu Ala Ser Ala Ser Val Leu
            20                  25                  30

Pro Met Val Leu Lys Ala Ala Ile Glu Leu Asp Leu Leu Glu Ile Met
        35                  40                  45

Ala Lys Ala Gly Pro Gly Ser Phe Leu Ser Pro Ser Asp Leu Ala Ser
    50                  55                  60

Gln Leu Pro Thr Lys Asn Pro Glu Ala Pro Val Met Leu Asp Arg Met
65                  70                  75                  80

Leu Arg Leu Leu Ala Ser Tyr Ser Ile Leu Thr Cys Ser Leu Arg Thr
                85                  90                  95

Leu Pro Asp Gly Lys Val Glu Arg Leu Tyr Cys Leu Gly Pro Val Cys
            100                 105                 110

Lys Phe Leu Thr Lys Asn Glu Asp Gly Val Ser Ile Ala Ala Leu Cys
        115                 120                 125

Leu Met Asn Gln Asp Lys Val Leu Val Glu Ser Trp Tyr His Leu Lys
    130                 135                 140

Asp Ala Val Leu Asp Gly Gly Ile Pro Phe Asn Lys Ala Tyr Gly Met
145                 150                 155                 160

Thr Ala Phe Asp Tyr His Gly Thr Asp Pro Arg Phe Asn Lys Val Phe
                165                 170                 175

Asn Lys Gly Met Ala Asp His Ser Thr Ile Thr Met Lys Lys Ile Leu
            180                 185                 190

Glu Thr Tyr Lys Gly Phe Glu Gly Leu Lys Ser Ile Val Asp Val Gly
        195                 200                 205

Gly Gly Thr Gly Ala Val Val Asn Met Ile Val Ser Lys Tyr Pro Ser
    210                 215                 220

Ile Lys Gly Ile Asn Phe Asp Leu Pro His Val Ile Glu Asp Ala Pro
225                 230                 235                 240

Gln Tyr Pro Gly Val Gln His Val Gly Gly Asp Met Phe Val Ser Val
                245                 250                 255

Pro Lys Gly Asn Ala Ile Phe Met Lys Trp Ile Cys His Asp Trp Ser
            260                 265                 270
```

Asp Glu His Cys Ile Lys Phe Leu Lys Asn Cys Tyr Ala Ala Leu Pro
        275                 280                 285

Asp Asp Gly Lys Val Ile Leu Ala Glu Cys Ile Leu Pro Val Ala Pro
    290                 295                 300

Asp Thr Ser Leu Ala Thr Lys Gly Val Val His Met Asp Val Ile Met
305                 310                 315                 320

Leu Ala His Asn Pro Gly Gly Lys Glu Arg Thr Glu Gln Glu Phe Glu
                325                 330                 335

Ala Leu Ala Lys Gly Ser Gly Phe Gln Gly Ile Arg Val Cys Cys Asp
            340                 345                 350

Ala Phe Asn Thr Tyr Val Ile Glu Phe Leu Lys Lys Ile
        355                 360                 365

<210> SEQ ID NO 55
<211> LENGTH: 271
<212> TYPE: PRT
<213> ORGANISM: Homo sapiens

<400> SEQUENCE: 55

Met Pro Glu Ala Pro Pro Leu Leu Leu Ala Ala Val Leu Leu Gly Leu
1               5                   10                  15

Val Leu Leu Val Val Leu Leu Leu Leu Leu Arg His Trp Gly Trp Gly
            20                  25                  30

Leu Cys Leu Ile Gly Trp Asn Glu Phe Ile Leu Gln Pro Ile His Asn
        35                  40                  45

Leu Leu Met Gly Asp Thr Lys Glu Gln Arg Ile Leu Asn His Val Leu
    50                  55                  60

Gln His Ala Glu Pro Gly Asn Ala Gln Ser Val Leu Glu Ala Ile Asp
65                  70                  75                  80

Thr Tyr Cys Glu Gln Lys Glu Trp Ala Met Asn Val Gly Asp Lys Lys
                85                  90                  95

Gly Lys Ile Val Asp Ala Val Ile Gln Glu His Gln Pro Ser Val Leu
            100                 105                 110

Leu Glu Leu Gly Ala Tyr Cys Gly Tyr Ser Ala Val Arg Met Ala Arg
        115                 120                 125

Leu Leu Ser Pro Gly Ala Arg Leu Ile Thr Ile Glu Ile Asn Pro Asp
    130                 135                 140

Cys Ala Ala Ile Thr Gln Arg Met Val Asp Phe Ala Gly Val Lys Asp
145                 150                 155                 160

Lys Val Thr Leu Val Val Gly Ala Ser Gln Asp Ile Ile Pro Gln Leu
                165                 170                 175

Lys Lys Lys Tyr Asp Val Asp Thr Leu Asp Met Val Phe Leu Asp His
            180                 185                 190

Trp Lys Asp Arg Tyr Leu Pro Asp Thr Leu Leu Leu Glu Glu Cys Gly
        195                 200                 205

Leu Leu Arg Lys Gly Thr Val Leu Leu Ala Asp Asn Val Ile Cys Pro
    210                 215                 220

Gly Ala Pro Asp Phe Leu Ala His Val Arg Gly Ser Ser Cys Phe Glu
225                 230                 235                 240

Cys Thr His Tyr Gln Ser Phe Leu Glu Tyr Arg Glu Val Val Asp Gly
                245                 250                 255

Leu Glu Lys Ala Ile Tyr Lys Gly Pro Gly Ser Glu Ala Gly Pro
            260                 265                 270

```
<210> SEQ ID NO 56
<211> LENGTH: 263
<212> TYPE: PRT
<213> ORGANISM: Vanilla planifolia

<400> SEQUENCE: 56

Met Ala Thr Thr Val Ala Thr Ala Thr Arg Ala Thr Glu Asn Lys Thr
1               5                   10                  15

Gln Thr Glu Glu Asn Ser Gln Asn Gly Gly Gln Gln Thr Gly His Gln
            20                  25                  30

Glu Ile Gly His Lys Ser Leu Leu Lys Ser Asp Ala Leu Tyr Gln Tyr
        35                  40                  45

Ile Leu Glu Thr Ser Val Tyr Pro Arg Glu Pro Glu Cys Leu Lys Glu
    50                  55                  60

Leu Arg Glu Ile Thr Ala Lys His Pro Trp Asn Leu Met Thr Thr Ser
65                  70                  75                  80

Ala Asp Glu Gly Gln Phe Leu Gly Met Leu Leu Lys Leu Ile Asn Ala
                85                  90                  95

Lys Asn Thr Met Glu Ile Gly Val Phe Thr Gly Tyr Ser Leu Leu Ala
            100                 105                 110

Thr Ala Leu Ala Leu Pro Asp Asp Gly Lys Ile Leu Ala Met Asp Ile
        115                 120                 125

Asn Arg Glu Asn Tyr Glu Leu Gly Leu Pro Leu Ile Gln Lys Ala Gly
    130                 135                 140

Val Ala His Lys Ile Asp Phe Arg Glu Gly Pro Ala Leu Pro Val Leu
145                 150                 155                 160

Asp Glu Leu Met Lys Asp Glu Ser Lys His Gly Ser Phe Asp Phe Ile
                165                 170                 175

Phe Val Asp Ala Asp Lys Asp Asn Tyr Leu Asn Tyr His Gln Arg Ile
            180                 185                 190

Ile Asp Leu Val Lys Val Gly Gly Val Ile Gly Tyr Asp Asn Thr Leu
        195                 200                 205

Trp Asn Gly Ala Val Val Leu Pro Pro Asp Ala Pro Met Arg Lys Tyr
    210                 215                 220

Ile Arg Tyr Tyr Arg Asp Phe Val Ile Glu Leu Asn Lys Glu Leu Ala
225                 230                 235                 240

Ala Asp Pro Arg Ile Glu Ile Cys Gln Leu Pro Val Gly Asp Gly Ile
                245                 250                 255

Thr Leu Cys Arg Arg Val Lys
            260
```